United States Patent
Ito et al.

(10) Patent No.: US 12,384,770 B2
(45) Date of Patent: *Aug. 12, 2025

(54) HETEROCYCLIC COMPOUND

(71) Applicant: Takeda Pharmaceutical Company Limited, Osaka (JP)

(72) Inventors: Masahiro Ito, Kanagawa (JP); Hideyuki Sugiyama, Kanagawa (JP); Takeshi Yamamoto, Kanagawa (JP); Keiko Kakegawa, Kanagawa (JP); Jinxing Li, Kanagawa (JP); Junsi Wang, Kanagawa (JP); Takahito Kasahara, Kanagawa (JP); Masato Yoshikawa, Kanagawa (JP)

(73) Assignee: Takeda Pharmaceutical Company Limited, Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 18/635,839

(22) Filed: Apr. 15, 2024

(65) Prior Publication Data

US 2024/0343721 A1  Oct. 17, 2024

Related U.S. Application Data

(62) Division of application No. 17/952,546, filed on Sep. 26, 2022, now Pat. No. 11,958,845, which is a division of application No. 17/030,504, filed on Sep. 24, 2020, now Pat. No. 11,453,661.

(30) Foreign Application Priority Data

Sep. 27, 2019 (JP) .................. 2019-177815

(51) Int. Cl.
*C07D 413/14* (2006.01)
*A61P 25/28* (2006.01)
*C07D 413/10* (2006.01)

(52) U.S. Cl.
CPC ............ *C07D 413/14* (2013.01); *A61P 25/28* (2018.01); *C07D 413/10* (2013.01)

(58) Field of Classification Search
CPC ...... C07D 413/14; C07D 413/10; A61P 25/28
USPC ...................................................... 514/364
See application file for complete search history.

(56) References Cited

U.S. PATENT DOCUMENTS

| | | |
|---|---|---|
| 7,250,504 B2 | 7/2007 | Grozinger et al. |
| 7,879,865 B2 | 2/2011 | Richon et al. |
| 8,026,260 B2 | 9/2011 | Close et al. |
| 8,067,472 B2 | 11/2011 | Richon et al. |
| 8,076,116 B2 | 12/2011 | Grozinger et al. |
| 8,088,951 B2 | 1/2012 | Tsai et al. |
| 8,389,553 B2 | 3/2013 | Harrington et al. |
| 8,435,780 B2 | 5/2013 | Grozinger et al. |
| 8,895,284 B2 | 11/2014 | Grozinger et al. |
| 8,901,156 B2 | 12/2014 | Baloglu et al. |
| 8,981,084 B2 | 3/2015 | Baloglu et al. |
| 8,999,289 B2 | 4/2015 | Anderson et al. |
| 9,056,843 B2 | 6/2015 | Hebach et al. |
| 9,096,559 B2 | 8/2015 | Harrington et al. |
| 9,238,028 B2 | 1/2016 | Van Den Bosch et al. |
| 9,365,498 B2 | 6/2016 | Holson et al. |
| 9,447,030 B2 | 9/2016 | Holson et al. |
| 9,480,673 B2 | 11/2016 | Freed et al. |
| 9,512,083 B2 | 12/2016 | Raje et al. |
| 9,572,854 B2 | 2/2017 | Anderson et al. |
| 9,670,193 B2 | 6/2017 | Hebach et al. |
| 9,890,172 B2 | 2/2018 | Holson et al. |
| 10,130,604 B2 | 11/2018 | Freed et al. |
| 10,172,905 B1 | 1/2019 | Anderson et al. |
| 10,406,146 B2 | 9/2019 | Kaieda et al. |
| 10,584,117 B2 | 3/2020 | Lee et al. |
| 11,453,661 B2 * | 9/2022 | Ito ................... C07D 413/10 |
| 2003/0129724 A1 | 7/2003 | Grozinger et al. |

(Continued)

FOREIGN PATENT DOCUMENTS

| | | |
|---|---|---|
| AU | 2013203735 A1 | 5/2013 |
| AU | 2016338118 B2 | 4/2017 |

(Continued)

OTHER PUBLICATIONS

Azad et al. "The future of epigenetic therapy in solid tumours-lessons from the past," Nat. Rev. Clin. Oncol., Apr. 2, 2013, 10:256-266.

Chuang et al., "Multiple roles of HDAC inhibition in neurodegenerative conditions," Trends in Neurosciences, 2009, 32(11):591-601.

Chung et al., "A Therapeutic Strategy Uses Histone Deacetylase Inhibitors to Modulate the Expression of Genes Involved in the Pathogenesis of Rheumatoid Arthritis," Molecular Therapy, Nov. 2003, 8(5):707-717.

(Continued)

*Primary Examiner* — Kahsay Habte
(74) *Attorney, Agent, or Firm* — Foley & Lardner LLP

(57) ABSTRACT

The present invention provides a heterocyclic compound having a HDAC6 inhibitory action, which is useful for the treatment of central nervous system diseases including neurodegenerative diseases, and the like, and a medicament comprising the compound. The present invention relates to a compound represented by the formula (I):

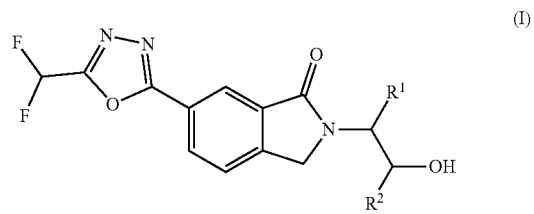

wherein each symbol is as defined in the description, or a salt thereof.

5 Claims, 5 Drawing Sheets

(56) References Cited

U.S. PATENT DOCUMENTS

| | | |
|---|---|---|
| 2004/0077591 A1 | 4/2004 | Dangond |
| 2004/0087657 A1 | 5/2004 | Richon et al. |
| 2004/0142859 A1 | 7/2004 | Steffan et al. |
| 2005/0009030 A1 | 1/2005 | Schweighoffer et al. |
| 2005/0227915 A1 | 10/2005 | Steffan et al. |
| 2006/0018921 A1 | 1/2006 | Levenson et al. |
| 2006/0135612 A1 | 6/2006 | Ferrante |
| 2007/0078083 A1 | 4/2007 | Barlow et al. |
| 2007/0207950 A1 | 9/2007 | Yao et al. |
| 2008/0114069 A1 | 5/2008 | Richon et al. |
| 2008/0221192 A1 | 9/2008 | Wan et al. |
| 2009/0036318 A1 | 2/2009 | Grozinger et al. |
| 2009/0136461 A1 | 5/2009 | Kim et al. |
| 2010/0004156 A1 | 1/2010 | Kaushal et al. |
| 2010/0022514 A1 | 1/2010 | Cho et al. |
| 2010/0247543 A1 | 9/2010 | Maes et al. |
| 2010/0292169 A1 | 11/2010 | Yao et al. |
| 2011/0124731 A1 | 5/2011 | Richon et al. |
| 2012/0039909 A1 | 2/2012 | Tsai et al. |
| 2012/0041067 A1 | 2/2012 | Richon et al. |
| 2012/0289495 A1 | 11/2012 | Baloglu et al. |
| 2013/0059883 A1 | 3/2013 | Baloglu et al. |
| 2013/0116204 A1 | 5/2013 | Schafer et al. |
| 2013/0203735 A1 | 8/2013 | Sisko et al. |
| 2013/0225543 A1 | 8/2013 | Jones et al. |
| 2013/0227717 A1 | 8/2013 | Van Den Bosch et al. |
| 2013/0317003 A1 | 11/2013 | Jacques et al. |
| 2014/0051680 A1 | 2/2014 | Jacques et al. |
| 2014/0080800 A1 | 3/2014 | Holson et al. |
| 2014/0080802 A1 | 3/2014 | Holson et al. |
| 2014/0235649 A1 | 8/2014 | Kovach et al. |
| 2014/0329825 A1 | 11/2014 | Hebach et al. |
| 2014/0378385 A1 | 12/2014 | Raje et al. |
| 2015/0038534 A1 | 2/2015 | Baloglu et al. |
| 2015/0119327 A1 | 4/2015 | Muotri et al. |
| 2015/0158884 A1 | 6/2015 | Jacques et al. |
| 2015/0184154 A1 | 7/2015 | Matthias et al. |
| 2016/0000766 A1 | 1/2016 | Van Den Bosch et al. |
| 2016/0221972 A1 | 8/2016 | Zheng et al. |
| 2016/0221973 A1 | 8/2016 | Zheng et al. |
| 2016/0222022 A1 | 8/2016 | Zheng et al. |
| 2016/0222028 A1 | 8/2016 | Zheng et al. |
| 2016/0251351 A1 | 9/2016 | Holson et al. |
| 2016/0347761 A1 | 12/2016 | Holson et al. |
| 2017/0015655 A1 | 1/2017 | Kaieda et al. |
| 2017/0044186 A1 | 2/2017 | Jacques et al. |
| 2017/0050984 A1 | 2/2017 | Jacques et al. |
| 2017/0096405 A1 | 4/2017 | Song et al. |
| 2017/0217955 A9 | 8/2017 | Holson et al. |
| 2017/0305866 A1 | 10/2017 | Raje et al. |
| 2018/0016282 A9 | 1/2018 | Holson et al. |
| 2018/0016314 A1 | 1/2018 | Harley et al. |
| 2018/0099977 A1 | 4/2018 | Holson et al. |
| 2018/0208606 A1 | 7/2018 | Jacques et al. |
| 2018/0230113 A1 | 8/2018 | Lee et al. |
| 2018/0256572 A1 | 9/2018 | Yates |
| 2018/0273495 A1 | 9/2018 | Kim et al. |
| 2018/0327423 A1 | 11/2018 | Jacques et al. |
| 2018/0370987 A1 | 12/2018 | Jacques et al. |
| 2019/0016692 A1 | 1/2019 | Zheng et al. |
| 2019/0016693 A1 | 1/2019 | Zheng et al. |
| 2019/0038589 A1 | 2/2019 | Freed et al. |
| 2019/0062288 A1 | 2/2019 | Zheng et al. |
| 2019/0112279 A1 | 4/2019 | Zheng et al. |
| 2019/0112280 A1 | 4/2019 | Zheng et al. |
| 2019/0112281 A1 | 4/2019 | Zheng et al. |
| 2019/0112282 A1 | 4/2019 | Zheng et al. |
| 2019/0112283 A1 | 4/2019 | Zheng et al. |
| 2019/0112284 A1 | 4/2019 | Zheng et al. |
| 2019/0119227 A1 | 4/2019 | Zheng et al. |
| 2019/0119228 A1 | 4/2019 | Zheng et al. |
| 2019/0119229 A1 | 4/2019 | Zheng et al. |
| 2019/0119230 A1 | 4/2019 | Zheng et al. |
| 2019/0119231 A1 | 4/2019 | Zheng et al. |
| 2019/0119232 A1 | 4/2019 | Zheng et al. |
| 2019/0119233 A1 | 4/2019 | Zheng et al. |
| 2019/0119234 A1 | 4/2019 | Zheng et al. |
| 2019/0119235 A1 | 4/2019 | Zheng et al. |
| 2019/0127339 A1 | 5/2019 | Zheng et al. |
| 2019/0135799 A1 | 5/2019 | Ito et al. |
| 2019/0233439 A1 | 8/2019 | Jacques et al. |
| 2020/0002298 A1 | 1/2020 | Zheng et al. |
| 2020/0048211 A1 | 2/2020 | Zheng et al. |
| 2020/0048212 A1 | 2/2020 | Zheng et al. |
| 2020/0055830 A1 | 2/2020 | Zheng et al. |
| 2020/0148704 A1 | 5/2020 | Jacques et al. |
| 2020/0354338 A1 | 11/2020 | Jin et al. |
| 2021/0009538 A1 | 1/2021 | Zheng et al. |
| 2021/0009539 A1 | 1/2021 | Zheng et al. |
| 2021/0009540 A1 | 1/2021 | Zheng et al. |
| 2022/0204461 A1 | 6/2022 | Zheng et al. |
| 2022/0235035 A1 | 7/2022 | Jin et al. |
| 2022/0363651 A1 | 11/2022 | Zheng et al. |
| 2023/0021554 A1 | 1/2023 | Jin et al. |
| 2023/0023761 A1 | 1/2023 | Jin et al. |

FOREIGN PATENT DOCUMENTS

| | | |
|---|---|---|
| CN | 101056632 A | 10/2007 |
| CN | 102770412 A | 11/2012 |
| CN | 105120860 A | 12/2015 |
| CN | 106232584 A | 12/2016 |
| CN | 107873023 A | 4/2018 |
| CN | 107980040 A | 5/2018 |
| CN | 108026088 A | 5/2018 |
| EP | 1 390 491 B1 | 2/2004 |
| EP | 1 746 982 | 1/2007 |
| EP | 2 624 832 | 8/2013 |
| EP | 3 187 497 A1 | 7/2017 |
| EP | 3 327 019 | 5/2018 |
| WO | WO-2005/105066 A2 | 11/2005 |
| WO | WO-2007/049262 | 5/2007 |
| WO | WO-2007/147868 | 12/2007 |
| WO | WO-2008/073733 | 6/2008 |
| WO | WO-2008/126932 | 10/2008 |
| WO | WO-2013/006408 A1 | 1/2013 |
| WO | WO-2013/009810 A1 | 1/2013 |
| WO | WO-2013/009827 A1 | 1/2013 |
| WO | WO-2013/009830 | 1/2013 |
| WO | WO-2013/066831 A1 | 5/2013 |
| WO | WO-2013/066833 A1 | 5/2013 |
| WO | WO-2013/066835 A1 | 5/2013 |
| WO | WO-2013/066838 A1 | 5/2013 |
| WO | WO-2013/066839 A2 | 5/2013 |
| WO | WO-2015/131788 | 9/2015 |
| WO | WO-2016/039398 | 3/2016 |
| WO | WO-2017/018803 A1 | 2/2017 |
| WO | WO-2017/018804 A1 | 2/2017 |
| WO | WO-2017/018805 A1 | 2/2017 |
| WO | WO-2017/023133 A2 | 2/2017 |
| WO | WO-2017/033946 A1 | 3/2017 |
| WO | WO-2017/222952 A1 | 12/2017 |
| WO | WO-2018/165520 A1 | 9/2018 |
| WO | WO-2018/215597 | 11/2018 |
| WO | WO-2019/027054 A1 | 2/2019 |
| WO | WO-2019/030692 | 2/2019 |
| WO | WO-2019/032652 | 2/2019 |
| WO | WO-2020/022794 | 1/2020 |
| WO | WO-2020/158762 | 8/2020 |

OTHER PUBLICATIONS

De Zoeten et al., "Histone Deacetylase 6 and Heat Shock Protein 90 Control the Functions of Foxp3 T-Regulatory Cells," Molecular and Cellular Biology, May 2011, 31(10):2066-2078.

Dubey et al., "Neurodegeneration and microtubule dynamics: death by a thousand cuts," Frontiers in Cellular Neuroscience, Sep. 9, 2015, 9(343):1-15.

Glauben et al., "Histone Hyperacetylation is Associated with Amelioration of Experimental Colitis in Mice," The Journal of Immunology, 2006, 176:5015-5022.

Goedert et al., "Frontotemporal Dementia: Implications for Understanding Alzheimer Disease," Cold Spring Harbor Perspectives in Medicine, 2012 (online Nov. 22, 2011), 4:a006254, 1-21.

(56) References Cited

OTHER PUBLICATIONS

Gouindarajan et al., "Reducing HDAC6 ameliorates cognitive deficits in a mouse model for Alzheimer's disease," EMBO Mol. Med., 2013, 5:52-63.
Haberland et al., "The many roles of histone deacetylases in development and physiology: implications for disease and therapy," Nature Reviews Genetics, Jan. 2009, 10:32-42.
Hancock et al., "HDAC inhibitor therapy in autoimmunity and transplantation," Ann. Rheum. Dis., 2012, 71(Supp.II):i46-i54.
Hubbert et al., "HDAC6 is a microtube-associated deacetylase," Nature, May 23, 2002, 417:455-458.
Jin et al., "Design, synthesis and preliminary biological evaluation of indoline-2,3-dione derivatives as novel HDAC inhibitors," Bioorganic & Medicinal Chemistry, 2015, 23:4728-4736.
Jochems et al., "Antidepressant-Like Properties of Novel HDAC6-Selective Inhibitors with Improved Brain Bioavailability," Neuropsychopharmacology, 2014, 39:389-400.
Kalin et al., "Development and Therapeutic Implications of Selective Histone Deacetylase 6 Inhibitors," Journal of Medicinal Chemistry, Apr. 29, 2013, 56:6297-6313.
Leroux, Michel R., "Tubulin acetyltransferase discovered: Ciliary role in the ancestral eukaryote expanded to neurons in metazoans," PNAS, Dec. 14, 2020, 107(50):21238-21239.
Li et al., "HDAC inhibitor reduces cytokine storm and facilitates induction of chimerism that reverses lupus in anti-CD3 conditioning regimen," PNAS, Mar. 25, 2008, 105(12):4796-4801.
Ligand-Protein Interactions and Molecular Similarity, H. Kubinyi, Ed., Springer, 1998, vol. 2-3, 243-244.
Lin et al., "Anti-rheumatic activities of histone deacetylase (HDAC) inhibitors in vivo in collagen-induced arthritis in rodents," British Journal of Pharmacology, 2007, 150:862-872.
Liu et al., "Histone deacetylase 6: structure, functions and development of selective inhibitors," Acta Pharmaceutica Sinica, 2015, 50(1):7-14.
Lu et al., Journal of International Neurology and Neurosurgery, Dec. 31, 2011, 348-352, with English abstract.
Ma et al., "Selective histone deacetylase 6 inhibitors: research advances," J. Int. Pharm. Res., Nov. 2018, 45(11):824-833, with English abstract.
Morfini et al., "Fast Axonal Transport Misregulation and Alzheimer's Disease," NeuroMolecular Medicine, 2002, 2:89-99.
Santo et al., "Preclinical activity, pharmacodynamic, and pharmacokinetic properties of a selective HDAC6 inhibitor, ACY-1215, in combination with bortezomib in multiple myeloma," Blood, 2012, 119(11):2579-2589.
Selenica et al., "Histone deacetylase 6 inhibition improves memory and reduces total tau levels in a mouse model of tau deposition," Alzheimer's Research & Therapy, 2014, 6:12.
Shakespear et al., "Histone deacetylases as regulators of inflammation and immunity," Trends in Immunology, Jul. 2011, 32(7):335-343.
The Practice of Medicinal Chemistry, 2nd. Ed., Wermuth, Ed., 2003, Chapters 9 and 10:131-157.
West et al., "New and emerging HDAC inhibitors for cancer treatment," The Journal of Clinical Investigation, Jan. 2014, 124(1):30-39.

* cited by examiner

HETEROCYCLIC COMPOUND

CROSS-REFERENCE TO RELATED APPLICATIONS

This application is a Divisional of U.S. application Ser. No. 17/952,546, filed Sep. 26, 2022, now U.S. Pat. No. 11,958,845, which is a Divisional of U.S. application Ser. No. 17/030,504, filed Sep. 24, 2020, now U.S. Pat. No. 11,453,661, which claims priority to JP 2019-177815, filed Sep. 27, 2019.

TECHNICAL FIELD

The present invention relates to a heterocyclic compound having a histone deacetylase (hereinafter sometimes to be referred to as "HDAC") inhibitory activity, preferably a class II HDAC inhibitory activity, more preferably a HDAC6 inhibitory activity, which may be useful for the treatment of central nervous system diseases including neurodegenerative diseases (Alzheimer's disease, progressive supranuclear palsy, etc.) and the like, a medicament comprising the compound, and the like.

BACKGROUND OF THE INVENTION

Nerve axon is known to play an important role in transport of nutritional factor, neurotransmitter, organelle and the like in nerve cell, and axon function disorder, axonal degeneration and intracellular accumulation of axon binding protein tau are observed in various neurodegenerative diseases (Non-Patent Document 1 and Non-Patent Document 2). Diseases characterized by intracellular tau accumulation are collectively called pathologically as tauopathy, and they encompass Alzheimer's disease, progressive supranuclear palsy and the like (Non-Patent Document 3). HDAC6 is an enzyme which plays a role in deacetylation of axon component, tubulin (Non-Patent Document 4), and microtubule containing acetylated tubulin is known to contribute to stability (Non-Patent Document 5). In addition, it is reported that Tubastatin A having a HDAC6 inhibitory activity increases acetylation of tubulin in tauopathy mouse model, and shows therapeutic effectiveness (Non-Patent Document 6). Therefore, the above-mentioned reports suggest that HDAC6 inhibitor has the potential to be a therapeutic drug for Alzheimer's disease and progressive supranuclear palsy via stabilization of axon.

As heterocyclic compounds, for example, the following compounds are known.

(1) Patent Document 1 discloses a compound represented by the following formula:

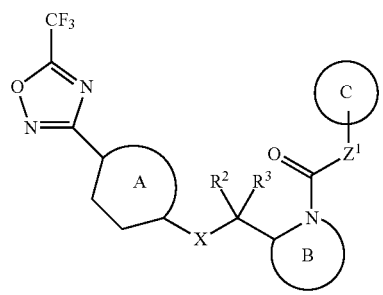

wherein each symbol is as defined in the document, which is a HDAC inhibitor, and is effective for the treatment of autoimmune diseases, inflammatory diseases, metabolic/osteoarticular degenerative diseases, neurodegenerative diseases/central diseases (e.g., schizophrenia, Alzheimer's disease (dementia of Alzheimer type), Parkinson's disease, Huntington's disease, Rubinstein-Taybi syndrome, muscular dystrophy, Rett syndrome, Charcot-Marie-Tooth disease, depression), neoplastic diseases and the like.

(2) Patent Document 2 discloses a compound represented by the following formula:

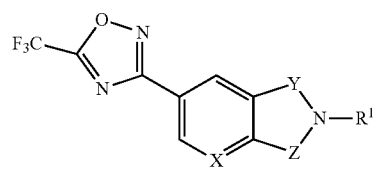

wherein each symbol is as defined in the document, which is a HDAC inhibitor, and is effective for the treatment of autoimmune diseases, inflammatory diseases, metabolic/osteoarticular degenerative diseases, neurodegenerative diseases/central diseases (e.g., schizophrenia, Alzheimer's disease (dementia of Alzheimer type), Parkinson's disease, Huntington's disease, Rubinstein-Taybi syndrome, muscular dystrophy, Rett syndrome, Charcot-Marie-Tooth disease, depression), neoplastic diseases and the like.

(3) Patent Document 3 discloses a compound represented by the following formula:

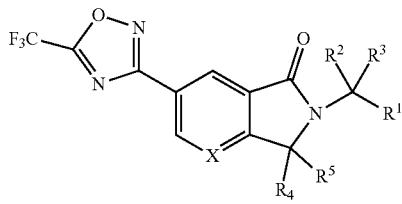

wherein each symbol is as defined in the document, which is a HDAC inhibitor, and is effective for the treatment of autoimmune diseases, inflammatory diseases, metabolic/osteoarticular degenerative diseases, neurodegenerative diseases/central diseases (e.g., schizophrenia, Alzheimer's disease (dementia of Alzheimer type), Parkinson's disease, Huntington's disease, Rubinstein-Taybi syndrome, muscular dystrophy, Rett syndrome, Charcot-Marie-Tooth disease, depression), neoplastic diseases and the like.

(4) Patent Document 4 discloses a compound represented by the following formula:

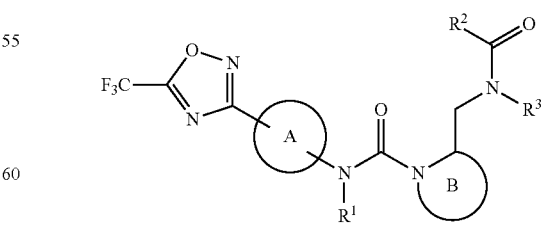

wherein each symbol is as defined in the document, which is a HDAC inhibitor, and is effective for the treatment of autoimmune diseases, inflammatory diseases, metabolic/osteoarticular degenerative diseases, neurodegenerative diseases/central diseases (e.g., schizophrenia, Alzheimer's disease (dementia of Alzheimer type), Parkinson's disease, Huntington's disease, Rubinstein-Taybi syndrome, muscular dystrophy, Rett syndrome, Charcot-Marie-Tooth disease, depression), neoplastic diseases and the like.

(5) Patent Document 5 discloses a compound represented by the following formula:

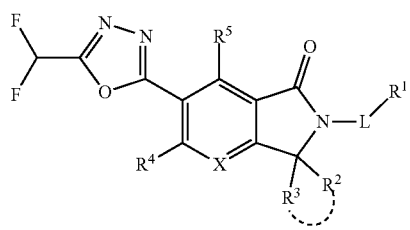
(I)

wherein each symbol is as defined in the document, which is a HDAC inhibitor, and is effective for the treatment of autoimmune diseases, inflammatory diseases, metabolic/osteoarticular degenerative diseases, neurodegenerative diseases/central diseases (e.g., schizophrenia, Alzheimer's disease (dementia of Alzheimer type), Parkinson's disease, Huntington's disease, Rubinstein-Taybi syndrome, muscular dystrophy, Rett syndrome, Charcot-Marie-Tooth disease, depression), neoplastic diseases and the like.

(6) Patent Document 6 discloses a compound represented by the following formula:

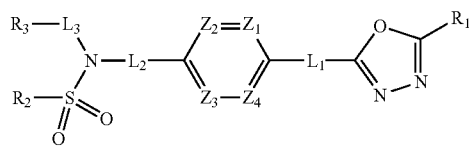
(I)

wherein each symbol is as defined in the document, which is a HDAC6 inhibitor, and is effective for the treatment of HDAC6-mediated diseases (e.g., infections, tumor, endocrine/nutritional/metabolic diseases, mental and behavioral disorders, neurological diseases, diseases of the eye and adnexa, cardiovascular diseases, respiratory diseases, digestive diseases, diseases of the skin and subcutaneous tissue, diseases of the musculoskeletal system and connective tissue, or congenital malformations, deformations and chromosomal abnormalities).

(7) Patent Document 7 discloses a compound represented by the following formula:

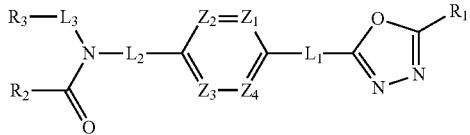

wherein each symbol is as defined in the document, which is a HDAC6 inhibitor, and is effective for the treatment of HDAC6-mediated diseases (e.g., infections, tumor, endocrine/nutritional/metabolic diseases, mental and behavioral disorders, neurological diseases, diseases of the eye and adnexa, cardiovascular diseases, respiratory diseases, digestive diseases, diseases of the skin and subcutaneous tissue, diseases of the musculoskeletal system and connective tissue, or congenital malformations, deformations and chromosomal abnormalities).

(8) Patent Document 8 discloses a compound represented by the following formula:

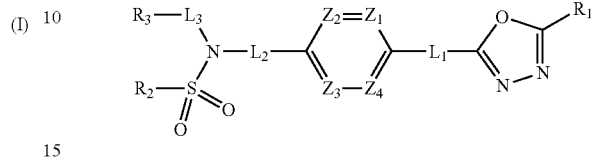

wherein each symbol is as defined in the document, which is a HDAC6 inhibitor, and is effective for the treatment of HDAC6-mediated diseases (e.g., infections, tumor, endocrine/nutritional/metabolic diseases, mental and behavioral disorders, neurological diseases, diseases of the eye and adnexa, cardiovascular diseases, respiratory diseases, digestive diseases, diseases of the skin and subcutaneous tissue, diseases of the musculoskeletal system and connective tissue, or congenital malformations, deformations and chromosomal abnormalities).

(9) Patent Document 9 discloses a compound represented by the following formula:

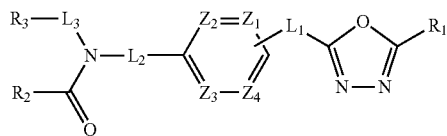

wherein each symbol is as defined in the document, which is a HDAC6 inhibitor, and is effective for the treatment of HDAC6-mediated diseases (e.g., infections, tumor, endocrine/nutritional/metabolic diseases, mental and behavioral disorders, neurological diseases, diseases of the eye and adnexa, cardiovascular diseases, respiratory diseases, digestive diseases, diseases of the skin and subcutaneous tissue, diseases of the musculoskeletal system and connective tissue, or congenital malformations, deformations and chromosomal abnormalities).

(10) Patent Document 10 discloses a compound represented by the following formula:

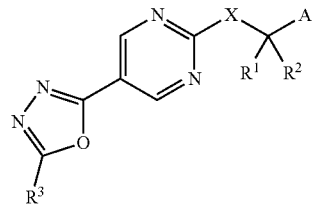

wherein each symbol is as defined in the document, which is a HDAC inhibitor, and is effective for the treatment of epilepsy, attentional deficit disorder, depression, anxiety, Alzheimer's disease, Parkinson's disease, Huntington's disease and the like.

(11) Patent Document 11 discloses a compound represented by the following formula:

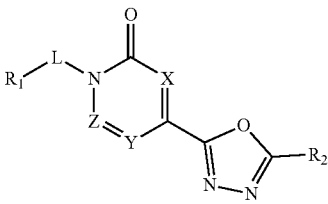

wherein each symbol is as defined in the document, which is a HDAC inhibitor, and is effective for the treatment of infectious diseases, tumors, endocrine diseases, nutritional and metabolic diseases and the like.

(12) Patent Document 12 discloses a compound represented by the following formula:

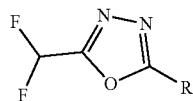

wherein each symbol is as defined in the document, which is a HDAC inhibitor, and is effective for the treatment of autoimmune diseases, inflammatory diseases, metabolic/osteoarticular degenerative diseases, neurodegenerative diseases/central diseases (e.g., schizophrenia, Alzheimer's disease (dementia of Alzheimer type), Parkinson's disease, Huntington's disease, Rubinstein-Taybi syndrome, muscular dystrophy, Rett syndrome, Charcot-Marie-Tooth disease, depression), neoplastic diseases and the like.

DOCUMENT LIST

Patent Document

Patent Document 1: WO 2016/031815
Patent Document 2: WO 2017/014321
Patent Document 3: WO 2017/014170
Patent Document 4: WO 2017/033946
Patent Document 5: WO 2019/027054
Patent Document 6: WO 2017/018803
Patent Document 7: WO 2017/018804
Patent Document 8: WO 2017/018805
Patent Document 9: WO 2017/023133
Patent Document 10: WO 2018/165520
Patent Document 11: WO 2020/022794
Patent Document 12: WO 2020/158762

Non-Patent Document

Non-Patent Document 1: Front Cell Neurosci. 9, 343, (2015).
Non-Patent Document 2: Neuromolecular Med. 2: 89-99, (2002).
Non-Patent Document 3: Cold Spring Harb Perspect Med. 2: a006254 (2012).
Non-Patent Document 4: Nature. 417: 455-458, (2002).
Non-Patent Document 5: Proc Natl Acad Sci USA. 107: 21238-21239, (2010).
Non-Patent Document 6: Alzheimers Res Ther. 6: 12, (2014).

SUMMARY OF THE INVENTION

Problems to be Solved by the Invention

The present invention aims to provide a heterocyclic compound having a HDAC inhibitory action, which is useful for the treatment of central nervous system diseases including neurodegenerative diseases (Alzheimer's disease, progressive supranuclear palsy, etc.) and the like, and a medicament comprising the compound.

Means of Solving the Problems

The present inventors have conducted intensive studies to solve the above-mentioned problems, and have found that a compound represented by the following formula (I) has a superior HDAC inhibitory action, and completed the present invention based on these findings.

Accordingly, the present invention provides the following.

[1] A compound represented by the formula (I):

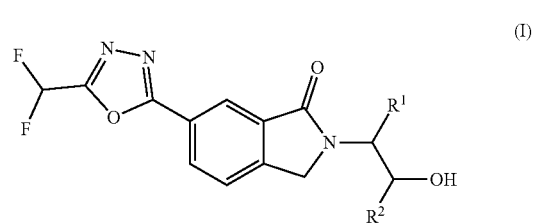

wherein
$R^1$ is an optionally substituted cyclic group, and
$R^2$ is an optionally substituted cyclic group,
or a salt thereof (hereinafter sometimes to be referred to as "compound (I)").

[2] The compound or salt according to the above-mentioned [1], which is represented by the formula (I'):

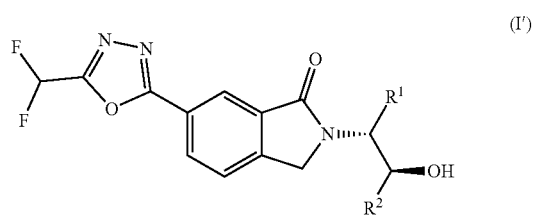

wherein each symbol is as defined in the above-mentioned [1].

[3] The compound or salt according to the above-mentioned [1],
wherein
$R^1$ is
(1) a $C_{3-10}$ cycloalkyl group optionally substituted by 1 to 3 halogen atoms,
(2) a $C_{6-14}$ aryl group optionally substituted by 1 to 3 substituents selected from (i) a halogen atom, (ii) a cyano group, and (iii) a $C_{1-6}$ alkyl group optionally substituted by 1 to 3 halogen atoms,
(3) a 5- or 6-membered monocyclic aromatic heterocyclic group optionally substituted by 1 to 3 substituents selected from (i) a halogen atom, (ii) a $C_{1-6}$ alkyl group optionally substituted by 1 to 3 halogen atoms, and (iii) a $C_{1-6}$ alkoxy group, or (4) a 3- to 8-membered monocyclic non-aromatic heterocyclic group, and $R^2$ is
(1) a $C_{3-10}$ cycloalkyl group optionally substituted by 1 to 3 halogen atoms,
(2) a $C_{6-14}$ aryl group optionally substituted by 1 to 3 substituents selected from (i) a halogen atom, and (ii) a $C_{1-6}$ alkyl group optionally substituted by 1 to 3 halogen atoms,
(3) a 5- or 6-membered monocyclic aromatic heterocyclic group optionally substituted by 1 to 3 substituents selected from (i) a halogen atom, (ii) a $C_{1-6}$ alkyl group optionally substituted by 1 to 3 halogen atoms, and (iii) a $C_{1-6}$ alkoxy group, or
(4) a 3- to 8-membered monocyclic non-aromatic heterocyclic group.

[4] The compound or salt according to the above-mentioned [1],
wherein
$R^1$ is
(1) a $C_{3-10}$ cycloalkyl group optionally substituted by 1 to 3 halogen atoms, or
(2) a 5- or 6-membered monocyclic aromatic heterocyclic group optionally substituted by 1 to 3 substituents selected from (i) a halogen atom, (ii) a $C_{1-6}$ alkyl group optionally substituted by 1 to 3 halogen atoms, and (iii) a $C_{1-6}$ alkoxy group, and $R^2$ is
(1) a $C_{6-14}$ aryl group optionally substituted by 1 to 3 substituents selected from (i) a halogen atom, and (ii) a $C_{1-6}$ alkyl group optionally substituted by 1 to 3 halogen atoms, or
(2) a 5- or 6-membered monocyclic aromatic heterocyclic group optionally substituted by 1 to 3 substituents selected from (i) a halogen atom, (ii) a $C_{1-6}$ alkyl group optionally substituted by 1 to 3 halogen atoms, and (iii) a $C_{1-6}$ alkoxy group.

[5] The compound or salt according to the above-mentioned [1],
wherein
$R^1$ is
(1) a $C_{3-10}$ cycloalkyl group, or
(2) a 6-membered monocyclic aromatic heterocyclic group optionally substituted by 1 to 3 halogen atoms, and $R^2$ is
(1) a $C_{6-14}$ aryl group optionally substituted by 1 to 3 halogen atoms, or
(2) a 6-membered monocyclic aromatic heterocyclic group optionally substituted by 1 to 3 halogen atoms.

[6] 6-[5-(Difluoromethyl)-1,3,4-oxadiazol-2-yl]-2-[(1R,2R)-2-hydroxy-1,2-di(pyridin-2-yl)ethyl]-2,3-dihydro-1H-isoindol-1-one or a salt thereof.

[7] 6-[5-(Difluoromethyl)-1,3,4-oxadiazol-2-yl]-2-[(1R,2R)-2-(5-fluoropyridin-2-yl)-2-hydroxy-1-(pyridin-2-yl)ethyl]-2,3-dihydro-1H-isoindol-1-one or a salt thereof.

[8] 2-[(1R,2R)-1,2-Bis(5-fluoropyridin-2-yl)-2-hydroxyethyl]-6-[5-(difluoromethyl)-1,3,4-oxadiazol-2-yl]-2,3-dihydro-1H-isoindol-1-one or a salt thereof.

[9] A medicament comprising the compound or salt according to the above-mentioned [1].

[10] The medicament according to the above-mentioned [9], which is a histone deacetylase 6 inhibitor.

[11] The medicament according to the above-mentioned [9], which is an agent for the prophylaxis or treatment of Alzheimer's disease or progressive supranuclear palsy.

[12] The compound or salt according to the above-mentioned [1] for use in the prophylaxis or treatment of Alzheimer's disease or progressive supranuclear palsy.

[13] A method of inhibiting histone deacetylase 6 in a mammal, which comprises administering an effective amount of the compound or salt according to the above-mentioned [1] to the mammal.

[14] A method for the prophylaxis or treatment of Alzheimer's disease or progressive supranuclear palsy in a mammal, which comprises administering an effective amount of the compound or salt according to the above-mentioned [1] to the mammal.

[15] Use of the compound or salt according to the above-mentioned [1] for the production of an agent for the prophylaxis or treatment of Alzheimer's disease or progressive supranuclear palsy.

Effect of the Invention

Compound (I) has a HDAC6 inhibitory activity, and may be useful for the treatment of central nervous system diseases including neurodegenerative diseases (Alzheimer's disease, progressive supranuclear palsy, etc.) and the like.

DETAILED DESCRIPTION OF THE INVENTION

Figure 1:
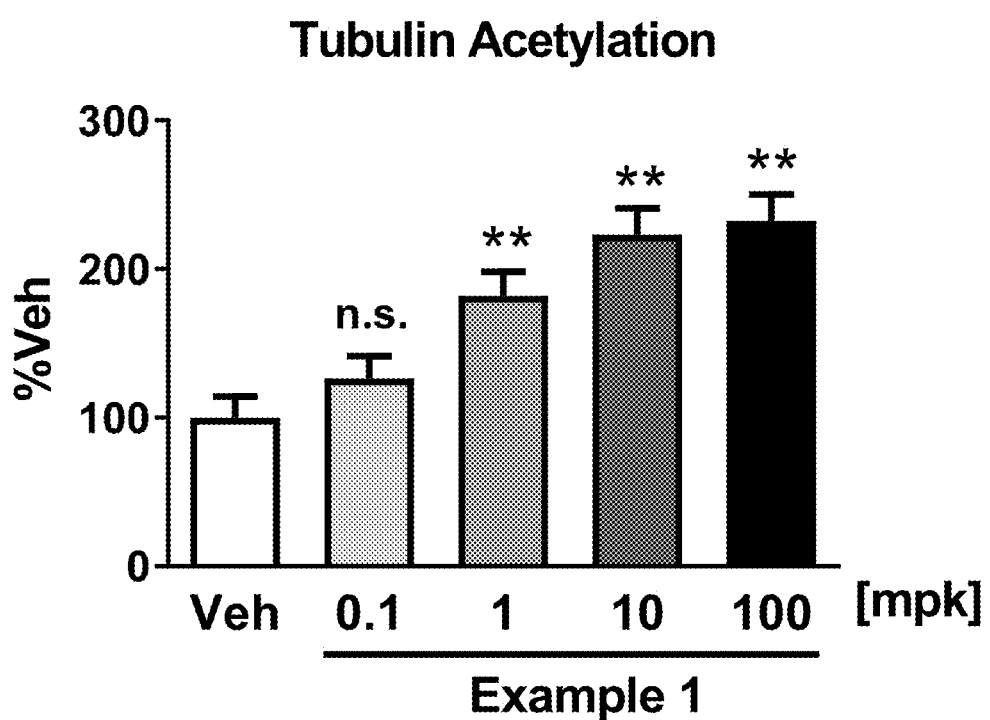
FIG. 1 is a graph showing increase in acetylated tubulin in mouse brain by the compound of Example 1. The vertical axis is relative tubulin acetylation level, and the horizontal axis is the dose (mg/kg).

The present invention is explained in detail in the following.

The definition of each symbol used in the formula (I) is explained.

$R^1$ and $R^2$ are the same or different and each is an optionally substituted cyclic group. Examples of the "cyclic group" of the "optionally substituted cyclic group" include a hydrocarbon ring group and a heterocyclic group.

Examples of the "hydrocarbon ring group" include a $C_{3-10}$ cycloalkyl group (e.g., cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, adamantyl, etc.), a $C_{3-10}$ cycloalkenyl group (e.g., cyclopropenyl, cyclobutenyl, cyclopentenyl, cyclohexenyl, cycloheptenyl, cyclooctenyl), a $C_{6-14}$ aryl group (e.g., phenyl, 1-naphthyl, 2-naphthyl, 1-anthryl, 2-anthryl, 9-anthryl) and the like.

Examples of the "heterocyclic group" include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

Examples of the "aromatic heterocyclic group" include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

Examples of the "non-aromatic heterocyclic group" include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

Preferable examples of the "7- to 10-membered bridged heterocyclic group" include quinuclidinyl and 7-azabicyclo[2.2.1]heptanyl.

Examples of the "optionally substituted cyclic group" represented by $R^1$ or $R^2$ include a cyclic group optionally having substituent(s) selected from the following Substituent group A.

The number of the substituents in the "optionally substituted cyclic group" is, for example, 1 to 3. When the number of the substituents is two or more, the respective substituents may be the same or different.

[Substituent Group A]
(1) a halogen atom (e.g., fluorine, chlorine, bromine, iodine),
(2) a nitro group,
(3) a cyano group,
(4) an oxo group,
(5) a hydroxy group,
(6) an optionally halogenated $C_{1-6}$ alkoxy group (e.g., methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy),
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by $C_{1-6}$ alkyl group(s) (e.g., phenylsulfonyloxy, toluenesulfonyloxy),
(20) an optionally halogenated $C_{1-6}$ alkylthio group (e.g., methylthio, difluoromethylthio, trifluoromethylthio, ethylthio, propylthio, isopropylthio, butylthio, 4,4,4-trifluorobutylthio, pentylthio, hexylthio),
(21) a 5- to 14-membered aromatic heterocyclic group (e.g., thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl, benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl),

(22) a 3- to 14-membered non-aromatic heterocyclic group (e.g., aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisoxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl, dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacridinyl, tetrahydrophenazinyl, tetrahydrothioxanthenyl, octahydroisoquinolyl),

(23) a formyl group,
(24) a carboxy group,
(25) an optionally halogenated $C_{1-6}$ alkyl-carbonyl group (e.g., acetyl, chloroacetyl, trifluoroacetyl, trichloroacetyl, propanoyl, butanoyl, pentanoyl, hexanoyl),
(26) a $C_{6-14}$ aryl-carbonyl group (e.g., benzoyl, 1-naphthoyl, 2-naphthoyl),
(27) a 5- to 14-membered aromatic heterocyclylcarbonyl group (e.g., nicotinoyl, isonicotinoyl, thenoyl, furoyl),
(28) a 3- to 14-membered non-aromatic heterocyclylcarbonyl group (e.g., morpholinylcarbonyl, piperidinylcarbonyl, pyrrolidinylcarbonyl),
(29) a $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl),
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group (e.g., methylcarbamoyl, ethylcarbamoyl, dimethylcarbamoyl, diethylcarbamoyl, N-ethyl-N-methylcarbamoyl),
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group (e.g., methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl, hexylsulfonyl),
(39) a $C_{6-14}$ arylsulfonyl group (e.g., phenylsulfonyl, 1-naphthylsulfonyl, 2-naphthylsulfonyl),
(40) a 5- to 14-membered aromatic heterocyclylsulfonyl group (e.g., pyridylsulfonyl, thienylsulfonyl),
(41) an optionally halogenated $C_{1-6}$ alkylsulfinyl group (e.g., methylsulfinyl, ethylsulfinyl),
(42) a $C_{6-14}$ aryl sulfinyl group (e.g., phenylsulfinyl, 1-naphthyl sulfinyl, 2-naphthyl sulfinyl),
(43) a 5- to 14-membered aromatic heterocyclylsulfinyl group (e.g., pyridyl sulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by $C_{1-6}$ alkyl group(s) (e.g., phenylsulfonylamino, toluenesulfonylamino),
(57) an optionally halogenated $C_{1-6}$ alkyl group (e.g., methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neo-pentyl, 5,5,5-trifluoropentyl, hexyl, 6,6,6-trifluorohexyl),
(58) a $C_{2-6}$ alkenyl group (e.g., ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl),
(59) a $C_{2-6}$ alkynyl group (e.g., ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 4-methyl-2-pentynyl),
(60) a $C_{3-10}$ cycloalkyl group (e.g., cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, adamantyl),
(61) a $C_{3-10}$ cycloalkenyl group (e.g., cyclopropenyl, cyclobutenyl, cyclopentenyl, cyclohexenyl, cycloheptenyl, cyclooctenyl), and

(62) a $C_{6-14}$ aryl group (e.g., phenyl, 1-naphthyl, 2-naphthyl, 1-anthryl, 2-anthryl, 9-anthryl).

$R^1$ is preferably
(1) a $C_{3-10}$ cycloalkyl group (e.g., cyclopropyl, cyclohexyl) optionally substituted by 1 to 3 halogen atoms (e.g., a fluorine atom),
(2) a $C_{6-14}$ aryl group (e.g., phenyl) optionally substituted by 1 to 3 substituents selected from
  (i) a halogen atom (e.g., a fluorine atom),
  (ii) a cyano group, and
  (iii) a $C_{1-6}$ alkyl group (e.g., methyl) optionally substituted by 1 to 3 halogen atoms (e.g., a fluorine atom),
(3) a 5- or 6-membered monocyclic aromatic heterocyclic group (e.g., pyrazolyl, pyridyl, pyrimidinyl, pyrazinyl, pyridazinyl) optionally substituted by 1 to 3 substituents selected from
  (i) a halogen atom (e.g., a fluorine atom),
  (ii) a $C_{1-6}$ alkyl group (e.g., methyl) optionally substituted by 1 to 3 halogen atoms (e.g., a fluorine atom), and
  (iii) a $C_{1-6}$ alkoxy group (e.g., ethoxy), or
(4) a 3- to 8-membered monocyclic non-aromatic heterocyclic group (e.g., tetrahydropyranyl).

$R^1$ is more preferably
(1) a $C_{3-10}$ cycloalkyl group (e.g., cyclopropyl, cyclohexyl) optionally substituted by 1 to 3 halogen atoms (e.g., a fluorine atom), or
(2) a 5- or 6-membered monocyclic aromatic heterocyclic group (e.g., pyrazolyl, pyridyl, pyrimidinyl, pyrazinyl, pyridazinyl) optionally substituted by 1 to 3 substituents selected from
  (i) a halogen atom (e.g., a fluorine atom),
  (ii) a $C_{1-6}$ alkyl group (e.g., methyl) optionally substituted by 1 to 3 halogen atoms (e.g., a fluorine atom), and
  (iii) a $C_{1-6}$ alkoxy group (e.g., ethoxy).

$R^1$ is particularly preferably
(1) a $C_{3-10}$ cycloalkyl group (e.g., cyclopropyl, cyclohexyl), or
(2) a 6-membered monocyclic aromatic heterocyclic group (e.g., pyridyl, pyrimidinyl, pyrazinyl, pyridazinyl) optionally substituted by 1 to 3 halogen atoms (e.g., a fluorine atom).

$R^2$ is preferably
(1) a $C_{3-10}$ cycloalkyl group (e.g., cyclopropyl, cyclohexyl) optionally substituted by 1 to 3 halogen atoms (e.g., a fluorine atom),
(2) a $C_{6-14}$ aryl group (e.g., phenyl) optionally substituted by 1 to 3 substituents selected from
  (i) a halogen atom (e.g., a fluorine atom, a chlorine atom), and
  (ii) a $C_{1-6}$ alkyl group (e.g., methyl) optionally substituted by 1 to 3 halogen atoms (e.g., a fluorine atom),
(3) a 5- or 6-membered monocyclic aromatic heterocyclic group (e.g., pyridyl, pyrimidinyl) optionally substituted by 1 to 3 substituents selected from
  (i) a halogen atom (e.g., a fluorine atom, a chlorine atom),
  (ii) a $C_{1-6}$ alkyl group (e.g., methyl) optionally substituted by 1 to 3 halogen atoms (e.g., a fluorine atom), and
  (iii) a $C_{1-6}$ alkoxy group (e.g., ethoxy), or
(4) a 3- to 8-membered monocyclic non-aromatic heterocyclic group (e.g., tetrahydropyranyl).

$R^2$ is more preferably
(1) a $C_{6-14}$ aryl group (e.g., phenyl) optionally substituted by 1 to 3 substituents selected from
  (i) a halogen atom (e.g., a fluorine atom, a chlorine atom), and
  (ii) a $C_{1-6}$ alkyl group (e.g., methyl) optionally substituted by 1 to 3 halogen atoms (e.g., a fluorine atom), or
(2) a 5- or 6-membered monocyclic aromatic heterocyclic group (e.g., pyridyl, pyrimidinyl) optionally substituted by 1 to 3 substituents selected from
  (i) a halogen atom (e.g., a fluorine atom, a chlorine atom),
  (ii) a $C_{1-6}$ alkyl group (e.g., methyl) optionally substituted by 1 to 3 halogen atoms (e.g., a fluorine atom), and
  (iii) a $C_{1-6}$ alkoxy group (e.g., ethoxy).

$R^2$ is particularly preferably
(1) a $C_{6-14}$ aryl group (e.g., phenyl) optionally substituted by 1 to 3 halogen atoms (e.g., a fluorine atom, a chlorine atom), or
(2) a 6-membered monocyclic aromatic heterocyclic group (e.g., pyridyl, pyrimidinyl) optionally substituted by 1 to 3 halogen atoms (e.g., a fluorine atom, a chlorine atom).

Preferred compound is compound (I) wherein
$R^1$ is
(1) a $C_{3-10}$ cycloalkyl group (e.g., cyclopropyl, cyclohexyl) optionally substituted by 1 to 3 halogen atoms (e.g., a fluorine atom),
(2) a $C_{6-14}$ aryl group (e.g., phenyl) optionally substituted by 1 to 3 substituents selected from
  (i) a halogen atom (e.g., a fluorine atom),
  (ii) a cyano group, and
  (iii) a $C_{1-6}$ alkyl group (e.g., methyl) optionally substituted by 1 to 3 halogen atoms (e.g., a fluorine atom),
(3) a 5- or 6-membered monocyclic aromatic heterocyclic group (e.g., pyrazolyl, pyridyl, pyrimidinyl, pyrazinyl, pyridazinyl) optionally substituted by 1 to 3 substituents selected from
  (i) a halogen atom (e.g., a fluorine atom),
  (ii) a $C_{1-6}$ alkyl group (e.g., methyl) optionally substituted by 1 to 3 halogen atoms (e.g., a fluorine atom), and
  (iii) a $C_{1-6}$ alkoxy group (e.g., ethoxy), or
(4) a 3- to 8-membered monocyclic non-aromatic heterocyclic group (e.g., tetrahydropyranyl), and $R^2$ is
(1) a $C_{3-10}$ cycloalkyl group (e.g., cyclopropyl, cyclohexyl) optionally substituted by 1 to 3 halogen atoms (e.g., a fluorine atom),
(2) a $C_{6-14}$ aryl group (e.g., phenyl) optionally substituted by 1 to 3 substituents selected from
  (i) a halogen atom (e.g., a fluorine atom, a chlorine atom), and
  (ii) a $C_{1-6}$ alkyl group (e.g., methyl) optionally substituted by 1 to 3 halogen atoms (e.g., a fluorine atom),
(3) a 5- or 6-membered monocyclic aromatic heterocyclic group (e.g., pyridyl, pyrimidinyl) optionally substituted by 1 to 3 substituents selected from
  (i) a halogen atom (e.g., a fluorine atom, a chlorine atom),
  (ii) a $C_{1-6}$ alkyl group (e.g., methyl) optionally substituted by 1 to 3 halogen atoms (e.g., a fluorine atom), and
  (iii) a $C_{1-6}$ alkoxy group (e.g., ethoxy), or
(4) a 3- to 8-membered monocyclic non-aromatic heterocyclic group (e.g., tetrahydropyranyl).

More preferred compound is compound (I) wherein
R¹ is
(1) a $C_{3-10}$ cycloalkyl group (e.g., cyclopropyl, cyclohexyl) optionally substituted by 1 to 3 halogen atoms (e.g., a fluorine atom), or
(2) a 5- or 6-membered monocyclic aromatic heterocyclic group (e.g., pyrazolyl, pyridyl, pyrimidinyl, pyrazinyl, pyridazinyl) optionally substituted by 1 to 3 substituents selected from
(i) a halogen atom (e.g., a fluorine atom),
(ii) a $C_{1-6}$ alkyl group (e.g., methyl) optionally substituted by 1 to 3 halogen atoms (e.g., a fluorine atom), and
(iii) a $C_{1-6}$ alkoxy group (e.g., ethoxy), and
R² is
(1) a $C_{6-14}$ aryl group (e.g., phenyl) optionally substituted by 1 to 3 substituents selected from
(i) a halogen atom (e.g., a fluorine atom, a chlorine atom), and
(ii) a $C_{1-6}$ alkyl group (e.g., methyl) optionally substituted by 1 to 3 halogen atoms (e.g., a fluorine atom), or
(2) a 5- or 6-membered monocyclic aromatic heterocyclic group (e.g., pyridyl, pyrimidinyl) optionally substituted by 1 to 3 substituents selected from
(i) a halogen atom (e.g., a fluorine atom, a chlorine atom),
(ii) a $C_{1-6}$ alkyl group (e.g., methyl) optionally substituted by 1 to 3 halogen atoms (e.g., a fluorine atom), and
(iii) a $C_{1-6}$ alkoxy group (e.g., ethoxy).

Particularly preferred compound is compound (I) wherein
R¹ is
(1) a $C_{3-10}$ cycloalkyl group (e.g., cyclopropyl, cyclohexyl), or
(2) a 6-membered monocyclic aromatic heterocyclic group (e.g., pyridyl, pyrimidinyl, pyrazinyl, pyridazinyl) optionally substituted by 1 to 3 halogen atoms (e.g., a fluorine atom), and
R² is
(1) a $C_{6-14}$ aryl group (e.g., phenyl) optionally substituted by 1 to 3 halogen atoms (e.g., a fluorine atom, a chlorine atom), or
(2) a 6-membered monocyclic aromatic heterocyclic group (e.g., pyridyl, pyrimidinyl) optionally substituted by 1 to 3 halogen atoms (e.g., a fluorine atom, a chlorine atom).

The configuration of compound (I) is preferably represented by the formula (I'):

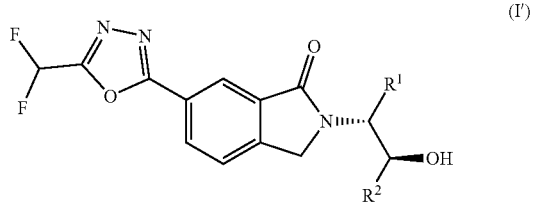

(I')

wherein each symbol is as defined above,
(hereinafter sometimes to be referred to as compound (I')).

As embodiments of compound (I), the following compounds (compound (I'-1) and compound (I'-2)) are exemplified.

Compound (I'-1)
Compound (I') wherein
R¹ is an optionally substituted hydrocarbon ring group, and
R² is an optionally substituted hydrocarbon ring group.

Compound (I'-1a)
Compound (I') wherein
R¹ is
(1) a $C_{3-10}$ cycloalkyl group (e.g., cyclopropyl, cyclohexyl) optionally substituted by 1 to 3 halogen atoms (e.g., a fluorine atom), or
(2) a $C_{6-14}$ aryl group (e.g., phenyl) optionally substituted by 1 to 3 substituents selected from
(i) a halogen atom (e.g., a fluorine atom),
(ii) a cyano group, and
(iii) a $C_{1-6}$ alkyl group (e.g., methyl) optionally substituted by 1 to 3 halogen atoms (e.g., a fluorine atom), and
R² is
(1) a $C_{3-10}$ cycloalkyl group (e.g., cyclopropyl, cyclohexyl) optionally substituted by 1 to 3 halogen atoms (e.g., a fluorine atom), or
(2) a $C_{6-14}$ aryl group (e.g., phenyl) optionally substituted by 1 to 3 substituents selected from
(i) a halogen atom (e.g., a fluorine atom, a chlorine atom), and
(ii) a $C_{1-6}$ alkyl group (e.g., methyl) optionally substituted by 1 to 3 halogen atoms (e.g., a fluorine atom).

Compound (I'-1b)
Compound (I') wherein
R¹ is a $C_{3-10}$ cycloalkyl group (e.g., cyclopropyl, cyclohexyl) optionally substituted by 1 to 3 halogen atoms (e.g., a fluorine atom), and
R² is a $C_{6-14}$ aryl group (e.g., phenyl) optionally substituted by 1 to 3 substituents selected from (i) a halogen atom (e.g., a fluorine atom, a chlorine atom), and (ii) a $C_{1-6}$ alkyl group (e.g., methyl) optionally substituted by 1 to 3 halogen atoms (e.g., a fluorine atom).

Compound (I'-1c)
Compound (I') wherein
R¹ is a $C_{3-10}$ cycloalkyl group (e.g., cyclopropyl, cyclohexyl), and
R² is a $C_{6-14}$ aryl group (e.g., phenyl) optionally substituted by 1 to 3 halogen atoms (e.g., a fluorine atom, a chlorine atom).

Compound (I'-2)
Compound (I') wherein
R¹ is an optionally substituted heterocyclic group, and
R² is an optionally substituted heterocyclic group.

Compound (I'-2a)
Compound (I') wherein
R¹ is
(1) a 5- or 6-membered monocyclic aromatic heterocyclic group (e.g., pyrazolyl, pyridyl, pyrimidinyl, pyrazinyl, pyridazinyl) optionally substituted by 1 to 3 substituents selected from
(i) a halogen atom (e.g., a fluorine atom),
(ii) a $C_{1-6}$ alkyl group (e.g., methyl) optionally substituted by 1 to 3 halogen atoms (e.g., a fluorine atom), and
(iii) a $C_{1-6}$ alkoxy group (e.g., ethoxy), or
(2) a 3- to 8-membered monocyclic non-aromatic heterocyclic group (e.g., tetrahydropyranyl), and
R² is
(1) a 5- or 6-membered monocyclic aromatic heterocyclic group (e.g., pyridyl, pyrimidinyl) optionally substituted by 1 to 3 substituents selected from (i) a halogen atom (e.g., a fluorine atom, a chlorine atom),
(ii) a $C_{1-6}$ alkyl group (e.g., methyl) optionally substituted by 1 to 3 halogen atoms (e.g., a fluorine atom), and
(iii) a $C_{1-6}$ alkoxy group (e.g., ethoxy), or
(2) a 3- to 8-membered monocyclic non-aromatic heterocyclic group (e.g., tetrahydropyranyl).

Compound (I'-2b)
Compound (I') wherein
$R^1$ is a 5- or 6-membered monocyclic aromatic heterocyclic group (e.g., pyrazolyl, pyridyl, pyrimidinyl, pyrazinyl, pyridazinyl) optionally substituted by 1 to 3 substituents selected from (i) a halogen atom (e.g., a fluorine atom), (ii) a $C_{1-6}$ alkyl group (e.g., methyl) optionally substituted by 1 to 3 halogen atoms (e.g., a fluorine atom), and (iii) a $C_{1-6}$ alkoxy group (e.g., ethoxy), and
$R^2$ is a 5- or 6-membered monocyclic aromatic heterocyclic group (e.g., pyridyl, pyrimidinyl) optionally substituted by 1 to 3 substituents selected from (i) a halogen atom (e.g., a fluorine atom, a chlorine atom), (ii) a $C_{1-6}$ alkyl group (e.g., methyl) optionally substituted by 1 to 3 halogen atoms (e.g., a fluorine atom), and (iii) a $C_{1-6}$ alkoxy group (e.g., ethoxy).

Compound (I'-2c)
Compound (I') wherein
$R^1$ is a 6-membered monocyclic aromatic heterocyclic group (e.g., pyridyl, pyrimidinyl, pyrazinyl, pyridazinyl) optionally substituted by 1 to 3 halogen atoms (e.g., a fluorine atom), and
$R^2$ is a 6-membered monocyclic aromatic heterocyclic group (e.g., pyridyl, pyrimidinyl) optionally substituted by 1 to 3 halogen atoms (e.g., a fluorine atom, a chlorine atom).

Specific examples of compound (I) include the compounds of Examples 1 to 150. Among them, compound (I) is preferably 6-[5-(difluoromethyl)-1,3,4-oxadiazol-2-yl]-2-[(1R,2R)-2-hydroxy-1,2-di(pyridin-2-yl)ethyl]-2,3-dihydro-1H-isoindol-1-one (Example 1) or a salt thereof, 6-[5-(difluoromethyl)-1,3,4-oxadiazol-2-yl]-2-[(1R,2R)-2-(5-fluoropyridin-2-yl)-2-hydroxy-1-(pyridin-2-yl)ethyl]-2,3-dihydro-1H-isoindol-1-one (Example 3) or a salt thereof, 2-[(1R,2R)-1,2-bis(5-fluoropyridin-2-yl)-2-hydroxyethyl]-6-[5-(difluoromethyl)-1,3,4-oxadiazol-2-yl]-2,3-dihydro-1H-isoindol-1-one (Example 5) or a salt thereof, 6-[5-(difluoromethyl)-1,3,4-oxadiazol-2-yl]-2-[(1R,2R)-2-(6-fluoropyridin-2-yl)-2-hydroxy-1-(pyridin-2-yl)ethyl]-2,3-dihydro-1H-isoindol-1-one (Example 7) or a salt thereof, or 2-[(1R,2S)-1-cyclopropyl-2-(4-fluorophenyl)-2-hydroxyethyl]-6-[5-(difluoromethyl)-1,3,4-oxadiazol-2-yl]-2,3-dihydro-1H-isoindol-1-one (Example 9) or a salt thereof, more preferably 6-[5-(difluoromethyl)-1,3,4-oxadiazol-2-yl]-2-[(1R,2R)-2-hydroxy-1,2-di(pyridin-2-yl)ethyl]-2,3-dihydro-1H-isoindol-1-one (Example 1) or a salt thereof, 6-[5-(difluoromethyl)-1,3,4-oxadiazol-2-yl]-2-[(1R,2R)-2-(5-fluoropyridin-2-yl)-2-hydroxy-1-(pyridin-2-yl)ethyl]-2,3-dihydro-1H-isoindol-1-one (Example 3) or a salt thereof, or 2-[(1R,2R)-1,2-bis(5-fluoropyridin-2-yl)-2-hydroxyethyl]-6-[5-(difluoromethyl)-1,3,4-oxadiazol-2-yl]-2,3-dihydro-1H-isoindol-1-one (Example 5) or a salt thereof.

When compound (I) is in a form of a salt, examples thereof include metal salts, an ammonium salt, salts with organic base, salts with inorganic acid, salts with organic acid, salts with basic or acidic amino acid, and the like. Preferable examples of the metal salt include alkali metal salts such as sodium salt, potassium salt and the like; alkaline earth metal salts such as calcium salt, magnesium salt, barium salt and the like; an aluminum salt, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salts with aspartic acid, glutamic acid and the like.

Among them, a pharmaceutically acceptable salt is preferable. For example, when a compound has an acidic functional group, examples thereof include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples thereof include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

[Production Method]

The production method of compound (I) is explained below.

The raw material compound and reagent used and the compound obtained in each step in the following production method may be each in a form of a salt, and examples of such salt include those similar to the salts of compound (I) and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature—300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.

alcohols: methanol, ethanol, tert-butyl alcohol, 2-methoxyethanol and the like;
  ethers: diethyl ether, diphenyl ether, tetrahydrofuran, 1,2-dimethoxyethane and the like;
  aromatic hydrocarbons: chlorobenzene, toluene, xylene and the like;
  saturated hydrocarbons: cyclohexane, hexane and the like; amides: N,N-dimethylformamide, N-methylpyrrolidone and the like;
  halogenated hydrocarbons: dichloromethane, carbon tetrachloride and the like;
  nitriles: acetonitrile and the like;
  sulfoxides: dimethyl sulfoxide and the like;
  aromatic organic bases: pyridine and the like;
  anhydrides: acetic anhydride and the like;
  organic acids: formic acid, acetic acid, trifluoroacetic acid and the like;
  inorganic acids: hydrochloric acid, sulfuric acid and the like; esters: ethyl acetate and the like;
  ketones: acetone, methyl ethyl ketone and the like; water.

The above-mentioned solvent can be used in a mixture of two or more kinds thereof in an appropriate ratio.

When a base is used for the reaction in each step, examples thereof include those described in Examples and the following bases.

inorganic bases: sodium hydroxide, magnesium hydroxide, sodium carbonate, calcium carbonate, sodium hydrogencarbonate, cesium carbonate, potassium acetate and the like;
  organic bases: triethylamine, diethylamine, N,N-diisopropylethylamine (DIPEA), pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
  metal alkoxides: sodium ethoxide, potassium tert-butoxide and the like;
  alkali metal hydrides: sodium hydride and the like; metal amides: sodium amide, lithium diisopropylamide, lithium hexamethyldisilazide and the like;
  organic lithiums: n-butyllithium and the like.

When an acid or an acid catalyst is used for the reaction in each step, examples thereof include those described in Examples and the following acids and acid catalysts.

inorganic acids: hydrochloric acid, sulfuric acid, nitric acid, hydrobromic acid, phosphoric acid and the like;
  organic acids: acetic acid, trifluoroacetic acid, citric acid, p-toluenesulfonic acid, 10-camphorsulfonic acid and the like; Lewis acid: boron trifluoride diethyl ether complex, zinc iodide, anhydrous aluminium chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like and a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; carbonate ester-type protecting groups such as tert-butylcarbonate and the like, and the like.

Examples of the protecting group for a carbonyl group of an aldehyde include acetal-type protecting groups such as dimethylacetal and the like; cyclic acetal-type protecting groups such as 1,3-dioxane and the like, and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; hydrazone-type protecting groups such as N,N-dimethylhydrazone and the like, and the like.

Examples of the protecting group for a carboxyl group include ester-type protecting groups such as methyl ester and the like; amide-type protecting groups such as N,N-dimethylamide and the like, and the like.

Examples of the protecting group for a thiol include ether-type protecting groups such as benzyl thioether and the like; ester-type protecting groups such as thioacetate ester, thiocarbonate, thiocarbamate and the like, and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; sulfonamide-type protecting groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminium hydride, sodium triacetoxyborohydride, sodium cyanoborohydride, diisobutylaluminium hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butylhydroperoxide and the like; perchlorates such as tetrabutylammonium perchlorate and the like; chlorates such as sodium chlorate and the like; chlorites such as sodium chlorite and the like; periodates such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, examples of the reagent to be used include a combination of a Lewis acid and an acid chloride or a combination of a Lewis acid and an alkylating agent (e.g., an alkyl halide, an alcohol, an olefin etc.). Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole etc.) and a base (e.g., an organic base etc.) are used as reagents.

When nucleophilic addition reaction by a carbo anion, nucleophilic 1,4-addition reaction (Michael addition reaction) by a carbo anion or nucleophilic substitution reaction by a carbo anion is carried out in each step, examples of the base to be used for generation of the carbo anion include organic lithiums, metal alkoxides, inorganic bases, organic bases and the like.

When Grignard reaction is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium or isopropylmagnesium chloride-lithium chloride complex in an ether, tetrahydrofuran and the like as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, a method using diphenylphosphorylazide, triphenylphosphine and azodicarboxylate, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

When esterification reaction, amidation reaction or ureation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (EDC HCl) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphorylazide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-disulfide (Lawesson reagent) etc.) can also be used instead of phosphorus pentasulfide.

When halogenation reaction is carried out in each step, examples of the halogenating agent to be used include N-iodosuccinimide, N-bromosuccinimide (NBS), N-chlorosuccinimide (NCS), bromine, sulfuryl chloride, trichloroisocyanuric acid and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two steps comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of tert-butyl ester, formic acid, triethylsilane and the like may be added to reductively-trap tert-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

When alkylation reaction is carried out in each step, an electrophile (e.g., an alkyl halide etc.) and a base (e.g., an organic base, an inorganic base, a metal alkoxide, a metal amide etc.) are used as reagents.

When cyanidation reaction is carried out in each step, examples of the reagent to be used include metal cyanides such as copper cyanide, potassium cyanide and the like.

Compound (I) can be produced according to the production methods shown in the following Scheme 1 or Scheme 2. Each symbol in the formulas of the schemes is as defined above, unless otherwise specified.

Moreover, compound (I) can be produced by carrying out protection reaction, deprotection reaction, amidation reaction, sulfonamidation reaction, ureation reaction, carbamoylation reaction, alkylation reaction, Mitsunobu reaction, hydrogenation reaction, oxidation reaction, reduction reaction, halogenation reaction, coupling reaction, nucleophilic addition reaction by a carbo anion, Grignard reaction, deoxofluorination reaction, dehydration reaction and the like singly or two or more thereof in combination.

The below-mentioned compound (Ia) (compound (I) wherein
R$^1$ is R$^{1a}$) can be produced according to the method shown in the following Scheme 1. R$^{1a}$ is an optionally substituted cyclopropyl group, an optionally substituted C$_{6-14}$ aryl group, or an optionally substituted 5- or 6-membered monocyclic aromatic heterocyclic group. The other symbols are as defined above.

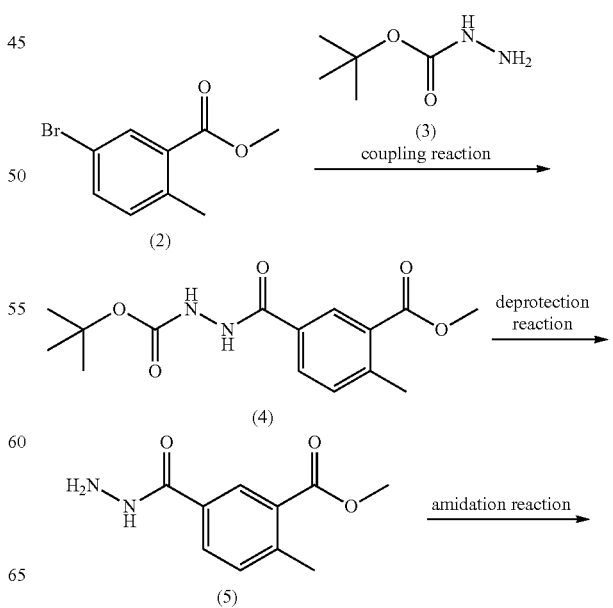

Scheme 1

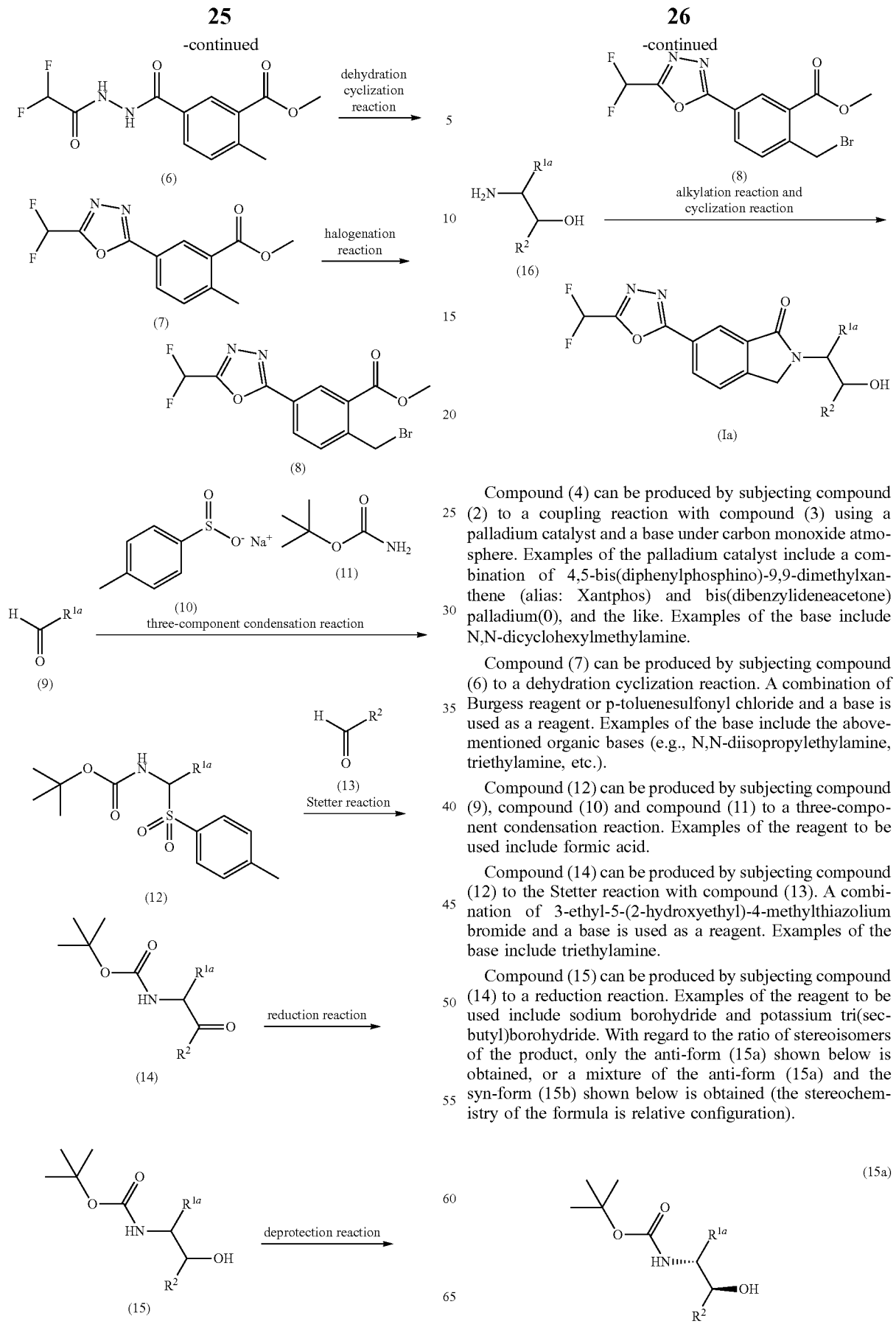

Compound (4) can be produced by subjecting compound (2) to a coupling reaction with compound (3) using a palladium catalyst and a base under carbon monoxide atmosphere. Examples of the palladium catalyst include a combination of 4,5-bis(diphenylphosphino)-9,9-dimethylxanthene (alias: Xantphos) and bis(dibenzylideneacetone)palladium(0), and the like. Examples of the base include N,N-dicyclohexylmethylamine.

Compound (7) can be produced by subjecting compound (6) to a dehydration cyclization reaction. A combination of Burgess reagent or p-toluenesulfonyl chloride and a base is used as a reagent. Examples of the base include the above-mentioned organic bases (e.g., N,N-diisopropylethylamine, triethylamine, etc.).

Compound (12) can be produced by subjecting compound (9), compound (10) and compound (11) to a three-component condensation reaction. Examples of the reagent to be used include formic acid.

Compound (14) can be produced by subjecting compound (12) to the Stetter reaction with compound (13). A combination of 3-ethyl-5-(2-hydroxyethyl)-4-methylthiazolium bromide and a base is used as a reagent. Examples of the base include triethylamine.

Compound (15) can be produced by subjecting compound (14) to a reduction reaction. Examples of the reagent to be used include sodium borohydride and potassium tri(sec-butyl)borohydride. With regard to the ratio of stereoisomers of the product, only the anti-form (15a) shown below is obtained, or a mixture of the anti-form (15a) and the syn-form (15b) shown below is obtained (the stereochemistry of the formula is relative configuration).

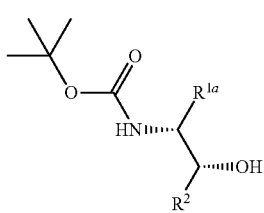

(15b)

Compound (Ia) can be produced by subjecting compound (16) to an alkylation reaction with compound (8), followed by a cyclization reaction. The cyclization reaction follows the alkylation reaction, but it may be carried out in stages. In this case, the cyclization reaction can be carried out under basic or acidic condition. Examples of the base include triethylamine, DIPEA, potassium acetate and the like. Examples of the acid to be used include acetic acid and the like.

The below-mentioned compound (Ib) (compound (I) wherein R$^1$ is R$^{1b}$) can be produced from compound (17) according to the method shown in the following Scheme 2. R$^{1b}$ is an optionally substituted cycloalkyl group, an optionally substituted C$_{6-14}$ aryl group, an optionally substituted 5- or 6-membered monocyclic aromatic heterocyclic group, or an optionally substituted 3- to 8-membered monocyclic non-aromatic heterocyclic group. X is a halogen atom. The other symbols are as defined above.

Scheme 2

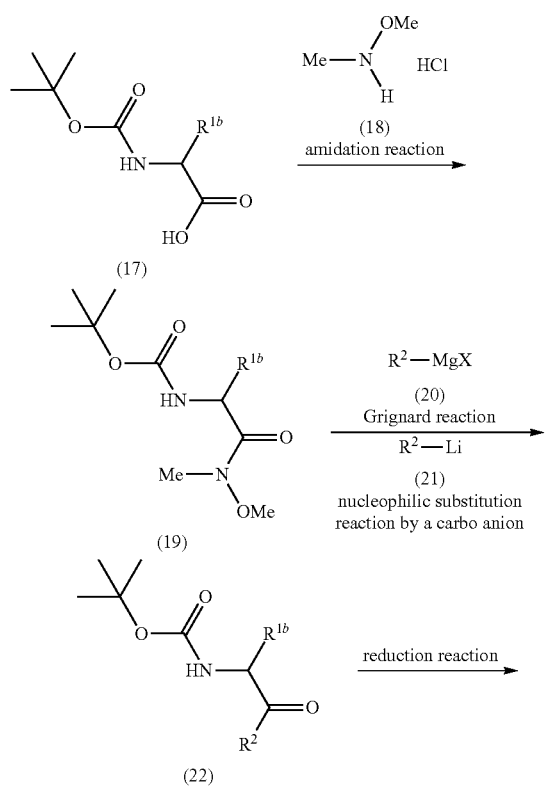

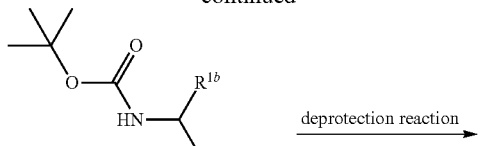

(23)

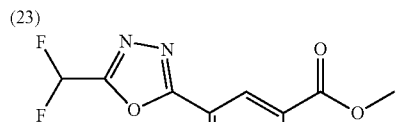

(24)  (8) alkylation reaction and cyclization reaction

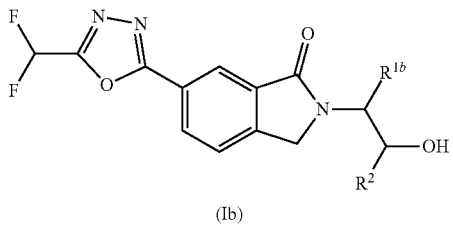

(Ib)

Compound (23) can be produced by subjecting compound (22) to a reduction reaction. Examples of the reagent to be used include sodium borohydride and potassium tri(sec-butyl)borohydride. Alternatively, a combination of aluminium triisopropoxide and 2-propanol may also be used. With regard to the ratio of stereoisomers of the product, only the anti-form (23a) shown below is obtained, or a mixture of the anti-form (23a) and the syn-form (23b) shown below is obtained (the stereochemistry of the formula is relative configuration).

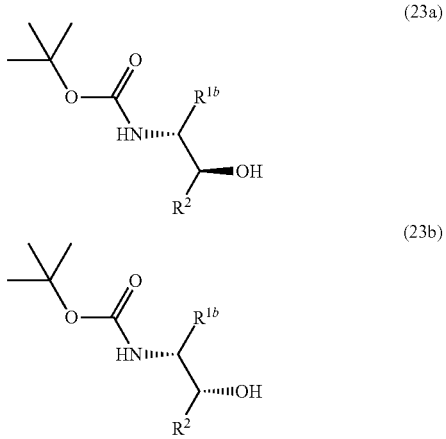

Compound (Ib) can be produced by subjecting compound (24) to an alkylation reaction with compound (8), followed by a cyclization reaction. The cyclization reaction follows the alkylation reaction, but it may be carried out in stages. In this case, the cyclization reaction can be carried out under basic or acidic condition. Examples of the base include triethylamine, DIPEA, potassium acetate and the like. Examples of the acid to be used include acetic acid and the like.

Compounds (2), (3), (9), (10), (11), (13), (17), (18), (20) and (21) which are used as raw materials in each production method may be commercially easily available or can be produced according to a method known per se.

As for the configurational isomers (E, Z forms) of compound (I), they can be isolated and purified when isomerization occurs, for example, according to a conventional separation means such as extraction, recrystallization, distillation, chromatography and the like to obtain a pure compound. In addition, the corresponding pure isomer can also be obtained by isomerizing a double bond using heating, an acid catalyst, a transition metal complex, a metal catalyst, a radical catalyst, light irradiation, a strong base catalyst and the like, according to the method described in Shin Jikken Kagaku Kouza 14 (The Chemical Society of Japan ed.), pages 251 to 253, or 4th Edition Jikken Kagaku Kouza 19 (The Chemical Society of Japan ed.), pages 273 to 274, or a method analogous thereto.

Compound (I) contains a stereoisomer depending on the kind of a substituent, and each stereoisomer and a mixture thereof are encompassed in the present invention.

Compound (I) may be a hydrate or a non-hydrate.

When the objective product is obtained as a free form by the above-mentioned reaction, it can be converted to a salt according to a conventional method, or when the objective product is obtained as a salt, it can be converted to a free form or other salt according to a conventional method. The thus-obtained compound (I) can also be isolated and purified from a reaction mixture according to a known method such as phase transfer, concentration, solvent extraction, distillation, crystallization, recrystallization, chromatography and the like.

When compound (I) contains a configurational isomer, a diastereomer, a conformer and the like, each can be isolated according to the above-mentioned separation and purification methods, if desired. In addition, when compound (I) is racemic, d-form and l-form can be isolated according to a conventional optical resolution such as preparative high performance liquid chromatography (preparative HPLC), supercritical fluid chromatography (preparative SFC) and the like.

The thus-obtained compound (I), other reaction intermediate therefor and starting compounds thereof can be isolated and purified from a reaction mixture according to a method known per se, for example, extraction, concentration, neutralization, filtration, distillation, recrystallization, column chromatography, thin layer chromatography, preparative high performance liquid chromatography (preparative HPLC), moderate-pressure preparative liquid chromatography (moderate-pressure preparative LC) and the like.

A salt of compound (I) can be produced according to a method known per se. For example, when compound (I) is a basic compound, it can be produced by adding an inorganic acid or organic acid, or when compound (I) is an acidic compound, by adding an organic base or inorganic base.

When compound (I) contains an optical isomer, each optical isomer and a mixture thereof are encompassed in the scope of the present invention, and these isomers can be subjected to optical resolution or can be produced respectively, according to a method known per se, if desired.

Compound (I) may be a crystal.

The crystal of compound (I) can be produced according to a crystallization method known per se.

Examples of the crystallization method include crystallization method from a solution, crystallization method from vapor, crystallization method from a melt, and the like.

The "crystallization method from a solution" is typically a method of shifting a non-saturated state to supersaturated state by varying factors involved in solubility of compounds (solvent composition, pH, temperature, ionic strength, redox state, etc.) or the amount of solvent. Specific examples thereof include a concentration method, a slow cooling method, a reaction method (a diffusion method, an electrolysis method), a hydrothermal growth method, a flux method and the like. Examples of the solvent to be used include aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitriles (e.g., acetonitrile, etc.), ketones (e.g., acetone, etc.), sulfoxides (e.g., dimethyl sulfoxide, etc.), acid amides (e.g., N,N-dimethylformamide, etc.), esters (e.g., ethyl acetate, isopropyl acetate, etc.), alcohols (e.g., methanol, ethanol, 2-propanol, etc.), water and the like. These solvents are used alone or in a combination of two or more at a suitable ratio (e.g., 1:1 to 1:100 (a volume ratio)). Where necessary, a seed crystal can be used.

The "crystallization method from vapor" is, for example, a vaporization method (a sealed tube method, a gas stream method), a gas phase reaction method, a chemical transportation method and the like.

The "crystallization method from a melt" is, for example, a normal freezing method (a pulling method, a temperature gradient method, a Bridgman method), a zone melting method (a zone leveling method, a floating zone method), a special growth method (a VLS method, a liquid phase epitaxy method) and the like.

Preferable examples of the crystallization method include a method comprising dissolving compound (I) in a suitable solvent (e.g., alcohols such as methanol, ethanol etc.) at 20° C. to 120° C., and cooling the obtained solution to a temperature (e.g., 0 to 50° C., preferably 0 to 20° C.) not higher than the dissolution temperature, and the like.

The thus-obtained crystals of the present invention can be isolated, for example, by filtration and the like.

An analysis method of the obtained crystal is generally a method of crystal analysis by powder X-ray diffraction. As a method of determining crystal orientation, a mechanical method or an optical method and the like can also be used.

The crystal of compound (I) obtained by the abovementioned production method may have high purity, high quality, and low hygroscopicity, may not be denatured even after a long-term preservation under general conditions, and may be expected to be superior in the stability. In addition, it may be also superior in the biological properties (e.g., pharmacokinetics (absorption, distribution, metabolism, excretion), efficacy expression etc.) and may be extremely useful as a medicament.

Compound (I) may be a prodrug. The prodrug of compound (I) means a compound which is converted to compound (I) with a reaction due to an enzyme, gastric acid and the like under the physiological condition in the living body, that is, a compound which is converted to compound (I) by enzymatic oxidation, reduction, hydrolysis and the like; a compound which is converted to compound (I) by hydrolysis and the like due to gastric acid, and the like. Examples of the prodrug for compound (I) include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation or tert-butylation); a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation); a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. These compounds can be produced from compound (I) according to a method known per se.

The prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, compound (I) and the prodrug of compound (I) are sometimes collectively abbreviated as "the compound of the present invention".

Compound (I) may be a hydrate, a non-hydrate, a solvate or a non-solvate.

In addition, compound (I) may be a compound labeled or substituted with an isotope (e.g., $^2$H, $^3$H, $^{11}$C, $^{14}$C, $^{18}$F, $^{35}$S, $^{125}$I) and the like. The compound labeled or substituted with an isotope may be used, for example, as a tracer (PET tracer) used in positron emission tomography (PET), and useful in the field of medical diagnosis and the like.

Compound (I) also encompasses a deuterium conversion form wherein $^1$H is converted to $^2$H(D).

Compound (I) also encompasses a tautomer thereof.

Compound (I) may be a pharmaceutically acceptable cocrystal or a salt thereof. The cocrystal or a salt thereof means a crystalline substance constituted with two or more special solids at room temperature, each having different physical properties (e.g., structure, melting point, melting heat, hygroscopicity, solubility and stability). The cocrystal or a salt thereof can be produced according to a cocrystallization a method known per se.

Compound (I) may also be used as a PET tracer.

Since the compound of the present invention has a superior HDAC inhibitory action, preferably class II HDAC inhibitory action, more preferably HDAC6 inhibitory action, it may be also useful as safe medicaments based on such action.

For example, the medicament of the present invention containing the compound of the present invention may be expected to show low toxicity (e.g., acute toxicity, chronic toxicity, genetic toxicity, hematotoxicity, reproductive toxicity, cardiotoxicity, carcinogenicity), and used for a mammal (e.g., mouse, rat, hamster, rabbit, cat, dog, bovine, sheep, monkey, human) as a prophylactic or therapeutic agent for HDAC-associated diseases, preferably class II HDAC-associated diseases, more preferably HDAC6-associated diseases, more specifically, the diseases described in (1)-(7) below.

Particularly, the compound of the present invention may be expected to show low genetic toxicity, and therefore, the medicament of the present invention may be expected to show low genetic toxicity.

(1) inflammatory diseases (e.g., acute pancreatitis, chronic pancreatitis, asthma, adult respiratory distress syndrome, chronic obstructive pulmonary disease (COPD), idiopathic pulmonary fibrosis, inflammatory bone disease, inflammatory pulmonary disease, inflammatory bowel disease, celiac disease, hepatitis, systemic inflammatory response syndrome (SIRS), postoperative or posttraumatic inflammation, pneumonia, nephritis, meningitis, cystitis, pharyngolaryngitis, gastric mucosal injury, spondylitis, arthritis, dermatitis, chronic pneumonia, bronchitis, pulmonary infarction, silicosis, pulmonary sarcoidosis, diabetic nephropathy, uveitis, suppurative hidradenitis etc.), (2) autoimmune diseases (e.g., rheumatoid arthritis, psoriasis, inflammatory bowel disease (e.g., Crohn's disease, ulcerative colitis etc.), Sjogren's syndrome, Behcet's disease, multiple sclerosis, systemic lupus erythematosus, lupus nephritis, discoid lupus erythematosus, Castleman's disease, ankylopoietic spondylarthritis, polymyositis, dermatomyositis (DM), polyarteritis nodosa (PN), mixed connective tissue disease (MCTD), scleroderma, profundus lupus erythematosus, chronic thyroiditis, Graves' disease, autoimmune gastritis, type I diabetes, autoimmune hemolytic anemia, autoimmune neutropenia, thrombocytopenia, atopic dermatitis, pemphigus, chronic active hepatitis, myasthenia gravis, graft versus host disease, Addison's disease, abnormal immunoresponse, arthritis, dermatitis, radiodermatitis, primary biliary cirrhosis etc.), (3) osteoarticular degenerative disease (e.g., rheumatoid arthritis, osteoporosis, osteoarthritis etc.), (4) neoplastic diseases [e.g., malignant tumor, angiogenesis glaucoma, infantile hemangioma, multiple myeloma, chronic sarcoma, metastasis melanoma, Kaposi's sacroma, vascular proliferation, cachexia, metastasis of the breast cancer, cancer (e.g., colorectal cancer (e.g., familial colorectal cancer, hereditary nonpolyposis colorectal cancer, gastrointestinal stromal tumor etc.), lung cancer (e.g., non-small cell lung cancer, small cell lung cancer, malignant mesothelioma etc.), mesothelioma, pancreatic cancer (e.g., pancreatic duct cancer etc.), gastric cancer (e.g., papillary adenocarcinoma, mucinous adenocarcinoma, adenosquamous carcinoma, etc.), breast cancer (e.g., invasive ductal carcinoma, ductal carcinoma in situ, inflammatory breast cancer etc.), ovarian cancer (e.g., ovarian epithelial carcinoma, extragonadal germ cell tumor, ovarian germ cell tumor, ovarian low malignant potential tumor etc.), prostate cancer (e.g., hormone-dependent prostate cancer, non-hormone dependent prostate cancer etc.), liver cancer (e.g., primary liver cancer, extrahepatic bile duct cancer etc.), thyroid cancer (e.g., medullary thyroid carcinoma etc.), kidney cancer (e.g., renal cell carcinoma, transitional cell carcinoma in kidney and urinary duct etc.), uterine cancer, brain tumor (e.g., pineal astrocytoma, pilocytic astrocytoma, diffuse astrocytoma, anaplastic astrocytoma etc.), melanoma, sarcoma, urinary bladder cancer, hematologic cancer and the like including multiple myeloma, hypophyseal adenoma, glioma, acoustic neurinoma, retinoblastoma, pharyngeal cancer, laryngeal cancer, cancer of the tongue, thymoma, esophagus cancer, duodenal cancer, colorectal cancer, rectal cancer, hepatoma, pancreatic endocrine tumor, bile duct cancer, gallbladder cancer, penile cancer, urinary duct cancer, testis tumor, vulvar cancer, cervix cancer, endometrial cancer, uterus sarcoma, cholionic disease, vaginal cancer, skin cancer, fungoid mycosis, basal cell tumor, soft tissue sarcoma, malignant lymphoma, Hodgkin's disease, myelodysplastic syndrome, adult T cell leukemia, chronic bone marrow proliferative disease, pancreatic endocrine, tumor fibrous histiocytoma, leiomyosarcoma, rhabdomyosarcoma, cancer of unknown primary), leukemia (e.g., acute leukemia (e.g., acute lymphatic leukemia, acute myelocytic leukemia etc.), chronic leukemia (e.g., chronic lymphatic leukemia, chronic myelocytic leukemia etc.), myelodysplastic syndrome), uterine sarcoma (e.g., mixed mesodermal tumor, uterine leiomyosarcoma, endometrial stromal tumor etc.), myelofibrosis etc.], (5) neurodegenerative diseases and/or central diseases (i) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, autistic spectrum syndrome, fragile X syndrome, Rett syndrome, adjustment disorder, bipolar disorder, neurosis, schizophrenia (e.g., positive symptom, negative symptom, cognitive symptom), cognitive dysfunction associated with schizophrenia, chronic fatigue syndrome, anxiety neurosis, compulsive neurosis, epilepsy, anxiety, anxious mental state, emotional abnormality, cyclothymia, nervous erethism, faint, addiction, low sex drive, attention deficit hyperactivity disorder (ADHD), psychotic major depression, refractory major depression, treatment-resistant depression, hreditary sastic praplegia], (ii) neurodegenerative diseases [e.g., Alzheimer's disease, dementia of Alzheimer type, Alzheimer-type senile dementia, Parkinson's disease, muscular dystrophy, Parkinson's disease associated with dementia, Huntington's disease, multi-infarct dementia, frontotemporal lobar degeneration [progressive supranuclear palsy, corticobasal degeneration, frontotemporal dementia and parkinsonism linked to MAPT mutation (FTDP-17), frontotemporal dementia, Pick's disease, argyrophilic grain dementia etc.], Parkinson's type dementia, Niemann-Pick syndrome, Down's disease, vascular dementia, postencephalitic parkinsonism, Lewy body dementia, Rubinstein-Taybi syndrome, HIV dementia, amyotrophic lateral sclerosis (ALS), motor neurogenesis disease (MND), Creutzfeldt-Jakob disease or prion disease, cerebral palsy, multiple sclerosis, Riley-Day syndrome], (iii) age-related cognition memory disorders [e.g., age-related memory disorders, senile dementia], (iv) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (v) respiratory depression caused by anesthetics, traumatic disease, or neurodegenerative disease and the like, (vi) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular spasm, Meniere's disease, autonomic ataxia, alopecia, glaucoma, hypertension, cardiac disease, tachycardia, congestive cardiac failure, hyperventilation, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, stress vomiting, peptic ulcer, diarrhea, constipation, postoperative ileus, (vii) pain (pain, cancer pain, acute pain caused by inflammation, pain associated with chronic inflammation, postoperative pain (incision pain, deep pain, visceral pain, chronic pain after operation and the like), muscular pain (muscular pain associated with chronic pain disease, stiff shoulder and the like), arthralgia, toothache, temporomandibular joint pain, headache (migraine, catatonic headache, headache associated with fever, headache associated with hypertension), visceral pain (cardiac pain, angina pain, abdominal pain, renal pain, urinary tract pain, bladder pain), obstetric and gynecologic pain (mittelschmerz, dysmenorrhea, labor pain), neuropathic pain (hernia of intervertebral disk, nerve root pain, neuralgia after herpes zoster, trigeminal neuralgia, lumbago and the like), peripheral neuropathy (CIPN) derived from anticancer drugs (taxane anti-cancer agent (e.g., paclitaxel (taxol), docetaxel), vinca alkaloid anti-cancer agent (e.g., vincristine, vinblastine), platinum preparation (e.g., cisplatin, carboplatin, oxaliplatin), molecularly targeted drug (e.g., bortezomib) and the like) and neurological symptoms associated therewith (chemotherapy-induced neuropathic pain (CINP))), (6) chronic heart failure or acute heart failure, acute decompensated heart failure, ischemic heart disease, cardiomyopathy, myocarditis, valvular disease, (7) peripheral neuropathy and the like (e.g., demyelinating diseases and neuropathy (multiple sclerosis, Guillain-Barre syndrome, Fisher syndrome, chronic inflammatory demyelinating polyneuropathy (CIDP), multifocal motor neuropathy (MMN), Charcot-Marie-Tooth disease, hereditary sensory and autonomic neuropathy, familial amyloidotic polyneuropathy)).

The medicament of the present invention may be preferably used as an agent for the prophylaxis or treatment of autoimmune disease, inflammatory disease, osteoarticular degenerative disease, neurodegenerative disease, central disease, neoplastic disease, or peripheral neuropathy, more preferably inflammatory bowel disease (preferably Crohn's disease or ulcerative colitis), systemic lupus erythematosus, rheumatoid arthritis, psoriasis, Sjogren's syndrome, Behcet's syndrome, multiple sclerosis, graft versus host disease, Alzheimer's disease (preferably dementia of Alzheimer type), schizophrenia, dementia with Lewy Bodies, frontotemporal lobar degeneration [progressive supranuclear palsy, corticobasal degeneration, frontotemporal dementia and parkisonism linked to MAPT mutation (FTDP-17), frontotemporal dementia, Pick's disease, argyrophilic grain dementia etc.], Parkinson's disease, Huntington's disease, Rubinstein-Taybi Syndrome, muscular dystrophy, Rett Syndrome, amyotrophic lateral sclerosis, Charcot-Marie-Tooth disease, depression, hereditary spastic praplegia, Riley-Day syndrome, Castleman's disease, leukemia, uterine leiomyosarcoma, prostate cancer, colon cancer, multiple myeloma, cachexia or myelofibrosis, chronic heart failure or acute heart failure, acute decompensated heart failure, ischemic heart disease, cardiomyopathy, myocarditis, valvular disease, peripheral neuropathy and the like.

The medicament of the present invention may be more preferably used as an agent for the prophylaxis or treatment of Alzheimer's disease, frontotemporal lobar degeneration [progressive supranuclear palsy, corticobasal degeneration, frontotemporal dementia and parkisonism linked to MAPT mutation (FTDP-17), frontotemporal dementia, Pick's disease, argyrophilic grain dementia etc.], Charcot-Marie-Tooth disease and the like, particularly Alzheimer's disease or progressive supranuclear palsy.

Here, the above-mentioned "prophylaxis" of a disease means, for example, administration of a medicament containing the compound of the present invention to patients who are expected to have a high risk of the onset due to some factor relating to the disease but have not developed the disease or patients who have developed the disease but do not have a subjective symptom, or administration of a medicament containing the compound of the present invention to patients who are feared to show recurrence of the disease after treatment of the disease.

A medicament containing the compound of the present invention may be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal etc.), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, cream, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor and administration to the lesion).

The content of the compound of the present invention in the medicament of the present invention is about 0.01 to 100% by weight of the entire medicament. The dose of the medicament of the present invention may vary depending on administration subject, administration route, disease and the like. For example, for oral administration to patients (body weight about 60 kg) with neurodegenerative disease (for example Alzheimer's disease, progressive supranuclear palsy, etc.), about 0.01 mg/kg body weight-about 50 mg/kg body weight, preferably about 0.05 mg/kg body weight-about 25 mg/kg body weight, more preferably about 0.1 mg/kg body weight-about 2 mg/kg body weight of an active ingredient (compound (I)) may be administered once to several portions per day.

Examples of the pharmaceutically acceptable carrier include various organic or inorganic carrier materials that are conventionally used as preparation materials, for example, excipient, lubricant, binding agent and disintegrant for solid preparations; or solvent, solubilizing agent, suspending agent, isotonic agent, buffering agent, soothing agent and the like for liquid preparations. Furthermore, when necessary, ordinary additives such as preservative, antioxidant, colorant, sweetening agent, adsorbing agent, wetting agent and the like can be also used as appropriate in an appropriate amount.

The dose of the medicament of the present invention as a sustained-release preparation varies depending on the kind and content of compound (I), dosage form, period of sustained drug release, subject animal of administration (e.g., mammals such as mouse, rat, hamster, guinea pig, rabbit, cat, dog, bovine, horse, swine, sheep, monkey, human etc.), and administration object. For example, for application by parenteral administration, about 0.1 to about 100 mg of compound (I) needs to be released from the administered preparation per 1 week.

Examples of the excipient include lactose, white sugar, D-mannitol, starch, corn starch, crystalline cellulose, and light anhydrous silicic acid.

Examples of the lubricant include magnesium stearate, calcium stearate, talc, and colloidal silica.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, and carboxymethylcellulose sodium.

Examples of the disintegrant include starch, carboxymethylcellulose, carboxymethylcellulose calcium, carboxymethylstarch sodium, and L-hydroxypropylcellulose.

Examples of the solvent include water for injection, alcohol, propylene glycol, Macrogol, sesame oil, corn oil, and olive oil.

Examples of the solubilizing agent include polyethylene glycol, propylene glycol, D-mannitol, benzyl benzoate, ethanol, trisaminomethane, cholesterol, triethanolamine, and sodium carbonate, sodium citrate.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; and hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like.

Examples of the isotonic agent include glucose, D-sorbitol, sodium chloride, glycerin, and D-mannitol.

Examples of the buffering agent include buffer solutions such as phosphates, acetates, carbonates, and citrates.

Examples of the soothing agent include benzyl alcohol.

Examples of the preservative include parahydroxybenzoates, chlorobutanol, benzyl alcohol, phenylethyl alcohol, dehydroacetic acid, and sorbic acid.

Examples of the antioxidant include sulfites, ascorbic acid, and α-tocopherol.

For the prophylaxis or treatment of various diseases, the compound of the present invention may also be used together with other drug (hereinafter, to be referred to as concomitant drug). In the following, a medicament to be used when the compound of the present invention is used together with other drug is referred to as "the combination agent of the present invention".

For example, when the compound of the present invention is used as a HDAC inhibitor, preferably a class II HDAC inhibitor, more preferably a HDAC6 inhibitor, it may be used together with the following drugs.

tranquilizer (diazepam, lorazepam, clorazepate dipotassium, oxazepam, chlordiazepoxide, medazepam, oxazolam, cloxazolam, clotiazepam, bromazepam, etizolam, fludiazepam, hydroxyzine, nitrazepam, triazolam, alprazolam etc.), antipsychotic (chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, clozapine, trifluoperazine dihydrochloride, fluphenazine hydrochloride, olanzapine, quetiapine fumarate, risperidone, aripiprazole, bromperidol, spiperone, reserpine, clocapramine hydrochloride, sulpiride, zotepine, tiotixene etc.), antiepileptic drug (phenytoin, ethosuximide, acetazolamide, chlordiazepoxide, trimethadione, carbamazepine, phenobarbital, primidone, sulthiame, sodium valproate, clonazepam, diazepam, nitrazepam etc.), antidepressant and therapeutic drug for manic psychosis [tricyclic or tetracyclic antidepressant drug (imipramine hydrochloride, clomipramine hydrochloride, desipramine hydrochloride, amitriptyline hydrochloride, nortriptyline hydrochloride, amoxapine, mianserin hydrochloride, maprotiline hydrochloride, etc.), noxiptiline, phenelzine, sulpiride, trazodone hydrochloride, lithium carbonate, selective serotonin reuptake inhibitor (fluvoxamine maleate, fluoxetine hydrochloride, citalopram hydrobromide, sertraline hydrochloride, paroxetine hydrochloride, paroxetine hydrochloride hydrate, escitalopram oxalate etc.), serotonin-noradrenalin reuptake inhibitor (venlafaxine hydrochloride, duloxetine hydrochloride, venlafaxine hydrochloride etc.), noradrenalin reuptake inhibitor (reboxetine mesylate etc.), noradrenalin-dopamine reuptake inhibitor (bupropion hydrochloride etc.), mirtazapine, trazodone hydrochloride, nefazodone hydrochloride, setiptiline maleate, 5-$HT_{1A}$ agonist (buspirone hydrochloride, tandospirone citrate, osemozotan hydrochloride) etc.]

benzodiazepine (clonazepam etc.), L-type calcium channel inhibitor (pregabalin etc.), 5-$HT_{1A}$ agonist (buspirone hydrochloride, tandospirone citrate, osemozotan hydrochloride etc.), 5-$HT_3$ antagonist (cyamemazine etc.), heart non-selective β inhibitor (propranolol hydrochloride, oxiprenolol hydrochloride etc.), histamine $H_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), drug that acts on metabotropic glutamate receptor, CCK antagonist, B3 adrenaline antagonist (amibegron hydrochloride etc.), GAT-1 inhibitor (tiagabine hydrochloride etc.), N-type calcium channel inhibitor, type II carbonic anhydrase inhibitor, NMDA glycine site agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioids antagonist, opioids agonist, uridine, nicotinic acid receptor agonists, thyroid hormone (T3, T4), TSH, TRH, MAO inhibitor (phenelzine sulfate, tranylcypromine sulfate, moclobemide etc.), 5-$HT_{2A}$ antagonist, 5-$HT_{2A}$ inverse agonist, COMT inhibitor (entacapone, etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for convulsion, therapeutic drug for fibromyalgia, therapeutic drug for headache, therapeutic drug for insomnia (etizolam, zopiclone, triazolam, xolpidem, ramelteon, indiplon etc.), therapeutic drug for quitting smoking, therapeutic drug for myasthenia gravis, therapeutic drug for cerebral infarction, therapeutic drug for manic psychosis, therapeutic drug for hypersomnia, therapeutic drug for pain, therapeutic drug for dysthymia, therapeutic drug for dysautonomia, therapeutic drug for male and female sexual dysfunction, therapeutic drug for migraine, therapeutic drug for pathological gambling, therapeutic drug for restless legs syndrome, therapeutic drug for substance dependence, therapeutic drug for alcohol-related disease, therapeutic drug for irritable bowel syndrome, therapeutic drug for Alzheimer's disease (donepezil, galanthamine, memantine, rivastigmine, etc.), therapeutic drug for Parkinson's disease (levodopa, carbidopa, benserazide, selegiline, rasagiline, zonisamide, entacapone, amantadine, talipexole, pramipexole, ropinirole, rotigotine, apomorphine, cabergoline, pergolide, bromocriptine, istradefylline, trihexyphenidyl, biperiden, piroheptine, profenamine, promethazine, droxidopa, amantadine hydrochloride, bromocriptine mesilate, trihexyphenidyl hydrochloride, selegiline hydrochloride, combination thereof etc.), therapeutic drug for Parkinson's disease associated with dementia (rivastigmine), therapeutic drug for Lewy body dementia (donepezil), therapeutic drug for ALS (riluzole, neurotrophic factor, etc.), therapeutic drug for hyperlipidemia such as cholesterol-lowering drug (statin series (pravastatin sodium, atorvastatin, simvastatin, rosuvastatin, etc.), fibrate (clofibrate etc.), squalene synthase inhibitor), therapeutic drug for abnormal behavior or dementia-related wandering (sedative drug, antianxiety drug, etc.), apoptosis inhibitor, antiobesity drug, antidiabetic drug, therapeutic drug for hypertension, therapeutic drug for hypotension, therapeutic drug for rheumatism (DMARD), anticancer drug, therapeutic drug for hypoparathyroidism (PTH), calcium receptor antagonist, sex hormone or derivative thereof (progesterone, estradiol, estradiol benzoate etc.), neuron differentiation accelerator, neurogeneration promotor, non-steroidal anti-inflammatory drug (meloxicam, tenoxicam, indomethacin, ibuprofen, celecoxib, rofecoxib, aspirin etc.), steroid (dexamethasone, cortisone acetate, etc.), anti-cytokine drug (TNF inhibitor, MAP kinase inhibitor, etc.), antibody medicament, nucleic acid or nucleic acid derivative, aptamer and the like.

For combined use, the administration time of the compound of the present invention and the concomitant drug is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration form of the combined use is not particularly limited, and the compound of the present invention and a concomitant drug only need to be combined on administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug in the combination agent of the present invention can be appropriately selected based on the subject of administration, administration route, disease and the like.

For example, while the content of the compound of the present invention in the combination agent of the present invention varies depending on the preparation form, it is generally about 0.01-100 wt %, preferably about 0.1-50 wt %, more preferably about 0.5-20 wt %, of the whole preparation.

The content of the concomitant drug in the combination agent of the present invention varies depending on the preparation form, and generally about 0.01 to 100% by weight, preferably about 0.1 to 50% by weight, further preferably about 0.5 to 20% by weight, of the entire preparation.

While the content of the additive such as a carrier and the like in the combination agent of the present invention varies depending on the form of a preparation, it is generally about 1 to 99.99% by weight, preferably about 10 to 90% by weight, based on the preparation.

When the compound of the present invention and the concomitant drug are separately prepared, the same content may be adopted.

Any amount of the concomitant drug can be adopted as long as the side effects do not cause a problem. The daily dosage in terms of the concomitant drug varies depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, generally about 0.001 to 2000 mg, preferably about 0.01 to 500 mg, further preferably about 0.1 to 100 mg, per 1 kg of a mammal and this is generally administered once to 4-times, divided in a day.

When the combination agent of the present invention is administered, the compound of the present invention and the concomitant drug can be administered simultaneously, or may be administered in a staggered manner. When administered at a time interval, the interval varies depending on the effective ingredient, dosage form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is an example. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is an example.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

The elution by column chromatography in the Examples was performed under the observation by TLC (Thin Layer Chromatography) unless otherwise specified. In the observation by TLC, 60 $F_{254}$ manufactured by Merck was used as a TLC plate, the solvent used as an elution solvent in column chromatography was used as a developing solvent, and UV detector was used for the detection. In silica gel column chromatography, the indication of NH means use of aminopropylsilane-bonded silica gel, and the indication of Diol means use of 3-(2,3-dihydroxypropoxy)propylsilane-bonded silica gel. In preparative HPLC (high performance liquid chromatography), the indication of C18 means use of octadecyl-bonded silica gel. The ratio for elution solvent is, unless otherwise specified, a volume mixing ratio.

For the analysis of 1H NMR, ACD/SpecManager (trade name) software and the like were used. Peaks of a hydroxyl group, an amino group and the like, having very mild proton peak, are not sometimes described.

MS (mass spectrum) was measured by LC/MS (liquid chromatograph mass spectrometer). As the ionization method, ESI (Electrospray Ionization) method, or APCI (Atmospheric Pressure Chemical Ionization) method was used. The data indicates actual measured value (found). While molecular ion peak is generally observed, a fragment ion is sometimes observed. In the case of a salt, a molecular ion peak or fragment ion peak of free form is generally observed. Elemental analysis value (Anal.) is described as calculated value (Calcd) and actual measured value (Found).

Powder X-RAY diffraction pattern was measured using Cu-Kα characteristic radiation from Rigaku Ultima IV, and characteristic peaks were described.

In the following Examples, the following abbreviations are used.

MS: mass spectrum
M: mol concentration
$CDCl_3$: deuterochloroform
$DMSO-d_6$: deuterodimethyl sulfoxide
$^1$H NMR: proton nuclear magnetic resonance
LC/MS: liquid chromatograph mass spectrometer
ESI: Electrospray Ionization
APCI: Atmospheric Pressure Chemical Ionization
AIBN: 2,2'-azobis(isobutyronitrile)
Boc: tert-butoxycarbonyl
CDI: 1,1'-carbonyldiimidazole
$CO_2$: carbon dioxide
DIPEA: N,N-diisopropylethylamine
DMF: N,N-dimethylformamide
DMSO: dimethyl sulfoxide
NBS: N-bromosuccinimide
TEA: triethylamine
THF: tetrahydrofuran
XANTPHOS: 4,5-bis(diphenylphosphino)-9,9-dimethylxanthene Example 1 and Example 2

6-[5-(difluoromethyl)-1,3,4-oxadiazol-2-yl]-2-[(1R,2R)-2-hydroxy-1,2-di(pyridin-2-yl)ethyl]-2,3-dihydro-1H-isoindol-1-one (Compound of Example 1)

6-[5-(difluoromethyl)-1,3,4-oxadiazol-2-yl]-2-[(1S,2S)-2-hydroxy-1,2-di(pyridin-2-yl)ethyl]-2,3-dihydro-1H-isoindol-1-one (Compound of Example 2)

A) tert-butyl 2-[3-(methoxycarbonyl)-4-methylbenzoyl]hydrazine-1-carboxylate

The following reaction was carried out by dividing the described scale into 5 reactions. A mixture of methyl 5-bromo-2-methylbenzoate (42.0 g), tert-butyl hydrazinecarboxylate (29.1 g), bis(dibenzylideneacetone)palladium (0) (5.27 g), XANTPHOS (5.30 g), N,N-dicyclohexylmethylamine (58.3 mL) and cyclopentyl methyl ether (1000 mL) was stirred under carbon monoxide atmosphere (0.5 MPa) at 95° C. for 5 hr. The five reaction mixtures were combined, and filtered through Celite, and the filtrate was concentrated under reduced pressure. The obtained residue was dissolved in a mixture of ethyl acetate and THF, and the solution was washed with water and saturated brine, dried over anhydrous sodium sulfate, and concentrated under reduced pressure. The residue was purified by silica gel column chromatography (NH, ethyl acetate), and crystallized from hexane/THF to give the title compound (45.7 g). 1H NMR (300 MHz, DMSO-$d_6$) δ1.32-1.53 (9H, m), 2.57 (3H, s), 3.86 (3H, s), 7.46 (1H, d, J=7.9 Hz), 7.94 (1H, dd, J=7.9, 1.5 Hz), 8.33 (1H, s), 8.93 (1H, s), 10.30 (1H, s).

MS: [M−H]$^-$ 307.0.

B) methyl 5-(hydrazinecarbonyl)-2-methylbenzoate hydrochloride

To tert-butyl 2-[3-(methoxycarbonyl)-4-methylbenzoyl]hydrazine-1-carboxylate (45.7 g) was added 4 M hydrogen chloride cyclopentyl methyl ether solution (200 mL) at room temperature. The mixture was stirred at room temperature for 3 days. The precipitated solid was collected by filtration, and dried to give the title compound (36.3 g). 1H NMR (300 MHz, DMSO-$d_6$) δ 2.59 (3H, s), 3.88 (3H, s), 7.52 (1H, d, J=8.1 Hz), 8.03 (1H, dd, J=7.9, 2.1 Hz), 8.36 (1H, d, J=1.9 Hz), 9.71-10.80 (2H, m), 11.64 (1H, br s).

MS: [M+H]$^+$ 209.0.

C) methyl 5-(5-(difluoromethyl)-1,3,4-oxadiazol-2-yl)-2-methylbenzoate

To a mixture of methyl 5-(hydrazinecarbonyl)-2-methylbenzoate hydrochloride (36.3 g) and THF (750 mL) was added DIPEA (129 mL) at room temperature. To the mixture was added dropwise difluoroacetic acid anhydride (27.6 mL) at 0° C. The mixture was stirred at room temperature for 2 hr, and to the mixture was added 4-methylbenzenesulfonyl chloride (56.5 g) at room temperature. The mixture was stirred overnight at room temperature, to the mixture was added water at room temperature, and the mixture was extracted with ethyl acetate.

The organic layer was separated, washed with saturated aqueous sodium hydrogencarbonate solution, water and saturated brine, dried over anhydrous sodium sulfate, and concentrated under reduced pressure. The residue was crystallized from hexane/ethyl acetate to give the title compound (24.9 g).

$^1$H NMR (300 MHz, DMSO-$d_6$) δ 2.63 (3H, s), 3.90 (3H, s), 7.37-7.75 (2H, m), 8.15 (1H, dd, J=8.1, 2.1 Hz), 8.44 (1H, d, J=2.3 Hz).

D) methyl 2-(bromomethyl)-5-((5-(difluoromethyl)-1,3,4-oxadiazol-2-yl))benzoate

To a mixture of methyl 5-(5-(difluoromethyl)-1,3,4-oxadiazol-2-yl)-2-methylbenzoate (14.0 g) and benzotrifluoride (500 mL) were added NBS (16.7 g) and AIBN (0.857 g) at room temperature. The mixture was stirred under argon atmosphere at 90° C. for 1 hr. To the mixture was added water at room temperature, and the mixture was extracted with ethyl acetate. The organic layer was separated, washed with saturated brine, dried over anhydrous sodium sulfate, and concentrated under reduced pressure. To the mixture of the residue and THF (500 mL) was added DIPEA (10.0 mL) at room temperature. To the mixture was added dropwise diethyl phosphonate (7.40 mL) at 0° C., and the mixture was stirred overnight at room temperature. To the mixture was added water at room temperature, and the mixture was extracted with ethyl acetate. The organic layer was separated, washed with saturated aqueous ammonium chloride solution, water and saturated brine, dried over anhydrous sodium sulfate, and concentrated under reduced pressure. The residue was purified by silica gel column chromatography (ethyl acetate/hexane), and crystallized from hexane/ethyl acetate to give the title compound (12.7 g).

$^1$H NMR (300 MHz, CDCl$_3$) δ 4.01 (3H, s), 5.01 (2H, s), 6.94 (1H, t, J=51.6 Hz), 7.69 (1H, d, J=8.3 Hz), 8.24 (1H, dd, J=7.9, 1.9 Hz), 8.71 (1H, d, J=1.9 Hz).

MS: [M+H]$^+$ 347.0.

E) tert-butyl [(4-methylbenzene-1-sulfonyl) (pyridin-2-yl)methyl]carbamate

To a mixture of sodium p-toluenesulfinate (25.0 g), tert-butyl carbamate (10.9 g) and water (140 mL) was added a mixture of pyridine-2-carbaldehyde (10.0 g) and methanol (70 mL) at room temperature. The mixture was stirred at room temperature for 30 min until the suspension became a clear solution. To the mixture was added formic acid (7.16 mL) at room temperature, and the mixture was stirred at room temperature for 3 days. The precipitated solid was collected by filtration, and washed with water and diisopropyl ether to give the title compound (23.0 g).

$^1$H NMR (300 MHz, DMSO-$d_6$) δ 1.02-1.31 (9H, m), 2.39 (3H, s), 6.06 (1H, br d, J=10.2 Hz), 7.31-7.52 (3H, m), 7.66 (2H, d, J=8.3 Hz), 7.77-7.84 (1H, m), 7.85-8.00 (1H, m), 8.15 (1H, br d, J=10.5 Hz), 8.49-8.63 (1H, m).

F) tert-butyl [2-oxo-1,2-di(pyridin-2-yl)ethyl]carbamate

A mixture of tert-butyl [(4-methylbenzene-1-sulfonyl) (pyridin-2-yl)methyl]carbamate (11.0 g), pyridine-2-carbaldehyde (3.41 g), 3-ethyl-5-(2-hydroxyethyl)-4-methylthiazolium bromide (1.53 g) and THF (121 mL) was degassed, and to the mixture was added dropwise triethylamine (63.3 mL) under argon atmosphere at room temperature. The mixture was again degassed, and the mixture was stirred overnight under argon atmosphere at 60° C. To the mixture was added saturated aqueous ammonium chloride solution at room temperature, and the mixture was partitioned between water and ethyl acetate. The separated organic layer was washed with water and saturated brine, dried over anhydrous sodium sulfate, and concentrated under reduced pressure. The residue was purified by silica gel column chromatography (NH, ethyl acetate/hexane) to give the title compound (9.81 g) as a crude product. The obtained compound was used in the next step without further purification.

MS: [M+H−Boc]$^+$214.0.

G) tert-butyl [(1RS,2RS)-2-hydroxy-1,2-di(pyridin-2-yl)ethyl]carbamate

To a mixture of tert-butyl [2-oxo-1,2-di(pyridin-2-yl) ethyl]carbamate (9.81 g), methanol (60 mL) and THF (60 mL) was added sodium borohydride (1.72 g) at 0° C., and the mixture was stirred overnight at room temperature. To the mixture was added water at 0° C., and the mixture was stirred at room temperature for 1 hr, and partitioned between water and ethyl acetate. The separated organic layer was washed with water and saturated brine. The combined aqueous layer was re-extracted with ethyl acetate, and the extract was washed with water and saturated brine. The combined organic layer was dried over anhydrous sodium sulfate, and concentrated under reduced pressure. The residue was solidified from ethyl acetate/hexane, and the obtained solid was recrystallized from ethyl acetate/hexane to give the title compound (6.64 g).

$^1$H NMR (300 MHz, DMSO-$d_6$) δ 1.11-1.35 (9H, m), 4.82-5.09 (2H, m), 5.61 (1H, d, J=5.1 Hz), 7.02 (1H, br d, J=8.7 Hz), 7.10 (1H, br d, J=7.9 Hz), 7.15-7.30 (3H, m), 7.57-7.80 (2H, m), 8.42 (1H, d, J=4.3 Hz), 8.52 (1H, br d, J=4.1 Hz).

MS: [M+H]$^+$ 316.1.

H) 6-[5-(difluoromethyl)-1,3,4-oxadiazol-2-yl]-2-[(1RS,2RS)-2-hydroxy-1,2-di(pyridin-2-yl)ethyl]-2,3-dihydro-1H-isoindol-1-one To a mixture of tert-butyl [(1RS,2RS)-2-hydroxy-1,2-di (pyridin-2-yl)ethyl]carbamate (2.21 g) and acetic acid (20 mL) was added dropwise hydrogen bromide (30% acetic acid solution, ca. 5.1 M), 11.0 mL) at room temperature, and the mixture was stirred overnight at room temperature. The mixture was concentrated under reduced pressure, and subjected to azeotropy with toluene and toluene/ethanol to give a white solid (3.54 g). To a mixture of the obtained solid (2.83 g), methyl 2-(bromomethyl)-5-(5-(difluoromethyl)-1, 3,4-oxadiazol-2-yl)benzoate (2.15 g) and DMF (50 mL) was added dropwise DIPEA (6.46 mL) at 0° C., and the mixture was stirred at room temperature for 3 hr. To the mixture was added dropwise acetic acid (2.12 mL) at room temperature, and the mixture was stirred overnight at room temperature. The mixture was poured into water at room temperature, and extracted with ethyl acetate. The extract was washed with water and saturated brine, dried over anhydrous sodium sulfate, and concentrated under reduced pressure. The residue was purified by silica gel column chromatography (methanol/ethyl acetate), and crystallized from ethyl acetate/ diisopropyl ether to give the title compound (2.36 g).

$^1$H NMR (300 MHz, DMSO-$d_6$) δ 4.75 (1H, d, J=18.8 Hz), 5.03 (1H, d, J=18.8 Hz), 5.49 (1H, dd, J=8.8, 5.8 Hz), 5.76 (1H, d, J=9.0 Hz), 5.98 (1H, d, J=5.6 Hz), 7.17 (1H, ddd, J=7.3, 4.9, 1.3 Hz), 7.30-7.72 (4H, m), 7.72-7.89 (3H, m), 8.04 (1H, d, J=0.8 Hz), 8.17-8.24 (1H, m), 8.25-8.31 (1H, m), 8.60-8.66 (1H, m).

MS: [M+H]$^+$ 450.1.

I) 6-[5-(difluoromethyl)-1,3,4-oxadiazol-2-yl]-2-[(1R,2R)-2-hydroxy-1,2-di(pyridin-2-yl)ethyl]-2,3-dihydro-1H-isoindol-1-one (Compound of Example 1) and

6-[5-(difluoromethyl)-1,3,4-oxadiazol-2-yl]-2-[(1S,2S)-2-hydroxy-1,2-di(pyridin-2-yl)ethyl]-2,3-dihydro-1H-isoindol-1-one (Compound of Example 2)

6-[5-(Difluoromethyl)-1,3,4-oxadiazol-2-yl]-2-[(1RS, 2RS)-2-hydroxy-1,2-di(pyridin-2-yl)ethyl]-2,3-dihydro-1H-isoindol-1-one was optically resolved by preparative SFC (column: CHIRALCEL OD-H, 20 mmID×250 mmL, 5 μm, mobile phase: $CO_2$/ethanol=770/230 (v/v)).

The fraction of the optical isomer having a longer retention time was concentrated under reduced pressure, and the residue was crystallized from hexane/ethyl acetate to give a white solid (1.20 g). The obtained solid (1.17 g) was dissolved in ethyl acetate (12 mL) at 70° C., and to the mixture was added dropwise heptane (10 mL) at 70° C. The mixture was stirred at 70° C. for 30 min, and then to the mixture was added dropwise additional heptane (30 mL) at 50° C.-75° C. The mixture was stirred at 50° C. for 30 min, and then at room temperature for 1 hr. The precipitated solid was collected by filtration, and washed with heptane to give 6-[5-(difluoromethyl)-1,3,4-oxadiazol-2-yl]-2-[(1R,2R)-2-hydroxy-1,2-di(pyridin-2-yl)ethyl]-2,3-dihydro-1H-isoindol-1-one (1.09 g, >99% e.e., retention time: 5.48 min (analysis column, column: CHIRALCEL OD-H, 4.6 mmID×150 mmL, 5 μm, mobile phase: $CO_2$/ethanol=770/

230 (v/v))). The absolute stereochemistry of the compound was determined by X-ray crystallography.

¹H NMR (300 MHz, DMSO-d₆) δ 4.75 (1H, d, J=18.8 Hz), 5.03 (1H, d, J=18.8 Hz), 5.49 (1H, dd, J=8.8, 5.5 Hz), 5.76 (1H, d, J=9.0 Hz), 5.98 (1H, d, J=5.6 Hz), 7.17 (1H, ddd, J=7.3, 4.9, 1.3 Hz), 7.28-7.72 (4H, m), 7.72-7.91 (3H, m), 8.04 (1H, d, J=0.8 Hz), 8.18-8.24 (1H, m), 8.25-8.32 (1H, m), 8.60-8.67 (1H, m).

MS: [M+H]⁺ 450.1.

Anal. Calcd for $C_{23}H_{17}F_2N_5O_3$:C, 61.47; H, 3.81; N, 15.58. Found: C, 61.68; H, 4.01; N, 15.80.

powder X-RAY crystal diffraction pattern (diffraction angle 2θ): 5.0°, 7.1°, 9.1°, 10.8°, 16.6°, 18.3°, 19.8°, 21.6°, 22.8°, 23.7°, 26.1°

The fraction of the optical isomer having a shorter retention time was concentrated under reduced pressure, and the residue was dissolved in ethyl acetate (15 mL) at 70° C. To the mixture was added dropwise diisopropyl ether (30 mL) at 50° C.-70° C., and the obtained suspension was stirred at 50° C. for 1 hr. To the mixture was added dropwise diisopropyl ether (30 mL) at 50° C., and the mixture was stirred at 50° C. for 30 min, and then at room temperature for 1 hr. The precipitated solid was collected by filtration, and washed with diisopropyl ether to give 6-[5-(difluoromethyl)-1,3,4-oxadiazol-2-yl]-2-[(1S,2S)-2-hydroxy-1,2-di(pyridin-2-yl)ethyl]-2,3-dihydro-1H-isoindol-1-one (1.02 g, >99% e.e., retention time: 4.52 min (analysis column: column: CHIRALCEL OD-H, 4.6 mmID×150 mmL, 5 µm, mobile phase: CO₂/ethanol=770/230 (v/v))).

MS: [M+H]⁺ 450.1.

Example 3 and Example 4

6-[5-(difluoromethyl)-1,3,4-oxadiazol-2-yl]-2-[(1R, 2R)-2-(5-fluoropyridin-2-yl)-2-hydroxy-1-(pyridin-2-yl)ethyl]-2,3-dihydro-1H-isoindol-1-one (Compound of Example 3)

6-[5-(difluoromethyl)-1,3,4-oxadiazol-2-yl]-2-[(1S, 2S)-2-(5-fluoropyridin-2-yl)-2-hydroxy-1-(pyridin-2-yl)ethyl]-2,3-dihydro-1H-isoindol-1-one (Compound of Example 4)

A) tert-butyl [2-(5-fluoropyridin-2-yl)-2-oxo-1-(pyridin-2-yl)ethyl]carbamate

A mixture of tert-butyl [(4-methylbenzene-1-sulfonyl)(pyridin-2-yl)methyl]carbamate (12.1 g), 5-fluoropyridine-2-carbaldehyde (4.18 g), 3-ethyl-5-(2-hydroxyethyl)-4-methylthiazolium bromide (1.68 g) and THF (134 mL) was degassed, and to the mixture was added dropwise triethylamine (69.6 mL) under argon atmosphere at room temperature. The mixture was again degassed, and the mixture was stirred overnight under argon atmosphere at 60° C. To the mixture was added saturated aqueous ammonium chloride solution at 0° C., and the mixture was partitioned between water and ethyl acetate. The separated organic layer was washed with water and saturated brine, dried over anhydrous sodium sulfate, and concentrated under reduced pressure. The residue was purified by silica gel column chromatography (NH, ethyl acetate/hexane), and crystallized from ethyl acetate/hexane to give the title compound (7.14 g).

¹H NMR (300 MHz, DMSO-d₆) δ 1.12-1.51 (9H, m), 6.76 (1H, d, J=8.7 Hz), 7.25 (1H, ddd, J=7.5, 4.9, 1.1 Hz), 7.45 (1H, br d, J=8.3 Hz), 7.53 (1H, d, J=7.9 Hz), 7.78 (1H, td, J=7.7, 1.9 Hz), 7.90 (1H, td, J=8.7, 2.6 Hz), 8.11 (1H, dd, J=8.8, 4.7 Hz), 8.33 (1H, br d, J=4.5 Hz), 8.64 (1H, d, J=2.6 Hz).

B) tert-butyl [(1RS,2RS)-2-(5-fluoropyridin-2-yl)-2-hydroxy-1-(pyridin-2-yl)ethyl]carbamate To a mixture of tert-butyl [2-(5-fluoropyridin-2-yl)-2-oxo-1-(pyridin-2-yl)ethyl]carbamate (6.59 g) and THF (100 mL) was added dropwise potassium tri(sec-butyl)borohydride (1 M THF solution, 23.9 mL) under argon atmosphere at −78° C., and the mixture was stirred at −78° C. for 2 hr. To the mixture was added water (40 mL) at −78° C., and to the mixture were added 2 M aqueous sodium hydroxide solution (99 mL) and 30% aqueous hydrogen peroxide (20.3 mL) while keeping the internal temperature 0° C. or below. The mixture was stirred at room temperature for 2 hr. Then, sodium thiosulfate pentahydrate (49.4 g) was dissolved in water (190 mL), and the obtained solution was added dropwise to the mixture at 0° C. The mixture was stirred at room temperature for 2 hr, and extracted with ethyl acetate. The extract was washed with water and saturated brine, dried over anhydrous sodium sulfate, and concentrated under reduced pressure. The residue was recrystallized from ethyl acetate/heptane to give the title compound (5.62 g).

¹H NMR (300 MHz, DMSO-d₆) δ 1.02-1.46 (9H, m), 4.84-5.10 (2H, m), 5.69 (1H, br d, J=4.5 Hz), 6.98 (1H, br d, J=8.7 Hz), 7.13-7.25 (2H, m), 7.29 (1H, dd, J=8.7, 4.5 Hz), 7.50-7.78 (2H, m), 8.43 (1H, dd, J=4.9, 0.8 Hz), 8.51 (1H, d, J=2.6 Hz).

MS: [M+H−Boc]⁺ 234.0.

C) 6-[5-(difluoromethyl)-1,3,4-oxadiazol-2-yl]-2-[(1RS,2RS)-2-(5-fluoropyridin-2-yl)-2-hydroxy-1-(pyridin-2-yl)ethyl]-2,3-dihydro-1H-isoindol-1-one To a mixture of tert-butyl [(1RS,2RS)-2-(5-fluoropyridin-2-yl)-2-hydroxy-1-(pyridin-2-yl)ethyl]carbamate (4.09 g) and acetic acid (40 mL) was added hydrogen bromide (25% acetic acid solution, 10 mL) at room temperature. To the mixture was added acetic acid (20 mL) at room temperature, and the mixture was stirred at room temperature for 30 min. The mixture was concentrated under reduced pressure, and the residue was subjected three times to azeotropy with toluene, and dried. To a mixture of the obtained residue, DIPEA (13.5 mL) and DMF (29 mL) was added dropwise a solution prepared by dissolving methyl 2-(bromomethyl)-5-(5-(difluoromethyl)-1,3,4-oxadiazol-2-yl)benzoate (3.87 g) in DMF (10 mL), at room temperature, and the mixture was stirred at room temperature for 60 hr. To the mixture was added water, and the mixture was extracted with ethyl acetate. The separated organic layer was washed with water and saturated brine, dried over anhydrous magnesium sulfate, and concentrated under reduced pressure. The residue was purified by silica gel column chromatography (ethyl acetate/hexane). The obtained solid was suspended in diisopropyl ether/ethyl acetate, and collected by filtration. The solid was suspended in hexane/ethyl acetate=1/1 (50 mL), sonicated, and stirred at 50° C. for 10 min. The solid was collected by filtration, and washed with hexane/ethyl acetate to give the title compound (4.09 g).

¹H NMR (300 MHz, DMSO-d₆) δ 4.70 (1H, d, J=19.6 Hz), 4.97 (1H, d, J=20.0 Hz), 5.47-5.57 (1H, m), 5.72 (1H, d, J=9.0 Hz), 6.05 (1H, d, J=5.3 Hz), 7.31-7.74 (5H, m), 7.77-7.87 (2H, m), 8.05 (1H, d, J=1.1 Hz), 8.22 (1H, dd, J=7.9, 1.5 Hz), 8.26 (1H, t, J=1.5 Hz), 8.57-8.69 (1H, m).

MS: [M+H]⁺ 468.1.

D) 6-[5-(difluoromethyl)-1,3,4-oxadiazol-2-yl]-2-[(1R,2R)-2-(5-fluoropyridin-2-yl)-2-hydroxy-1-(pyridin-2-yl)ethyl]-2,3-dihydro-1H-isoindol-1-one (Compound of Example 3) and 6-[5-(difluoromethyl)-1,3,4-oxadiazol-2-yl]-2-[(1S,2S)-2-(5-fluoropyridin-2-yl)-2-hydroxy-1-(pyridin-2-yl)ethyl]-2,3-dihydro-1H-isoindol-1-one (Compound of Example 4)

6-[5-(Difluoromethyl)-1,3,4-oxadiazol-2-yl]-2-[(1RS,2RS)-2-(5-fluoropyridin-2-yl)-2-hydroxy-1-(pyridin-2-yl)ethyl]-2,3-dihydro-1H-isoindol-1-one (3.09 g) was optically resolved by preparative HPLC (column: CHIRALCEL OD, 50 mmID×500 mmL, 20 μm, mobile phase: hexane/ethanol=700/300 (v/v)).

The fraction of the optical isomer having a longer retention time was concentrated under reduced pressure, and the residue was crystallized from heptane/isopropyl acetate to give 6-[5-(difluoromethyl)-1,3,4-oxadiazol-2-yl]-2-[(1R,2R)-2-(5-fluoropyridin-2-yl)-2-hydroxy-1-(pyridin-2-yl)ethyl]-2,3-dihydro-1H-isoindol-1-one (1.35 g, 99% e.e., retention time: 9.16 min (analysis condition, column: CHIRALCEL OD-H, 4.6 mmID×250 mmL, 5 μm, mobile phase: hexane/ethanol=700/300 (v/v)). The absolute stereochemistry of the compound was determined by X-ray crystallography.

$^1$H NMR (300 MHz, DMSO-$d_6$) δ 4.71 (1H, d, J=18.8 Hz), 4.97 (1H, d, J=18.8 Hz), 5.52 (1H, dd, J=9.0, 5.3 Hz), 5.72 (1H, d, J=9.0 Hz), 6.05 (1H, d, J=5.3 Hz), 7.31-7.74 (5H, m), 7.77-7.89 (2H, m), 8.05 (1H, d, J=1.1 Hz), 8.22 (1H, dd, J=8.1, 1.7 Hz), 8.26 (1H, t, J=1.5 Hz), 8.53-8.72 (1H, m).

MS: [M+H]$^+$ 468.1.

Anal. Calcd for $C_{23}H_{16}F_3N_5O_3 \cdot 3H_2O$: C, 58.43; H, 3.54; N, 14.81. Found: C, 58.53; H, 3.53; N, 14.78.

powder X-RAY crystal diffraction pattern (diffraction angle 2θ): 7.2°, 11.3°, 16.2°, 19.2°, 22.1°, 22.7°, 24.2°, 26.5°

The fraction of the optical isomer having a shorter retention time was concentrated under reduced pressure, and the residue was crystallized from heptane/isopropyl acetate to give 6-[5-(difluoromethyl)-1,3,4-oxadiazol-2-yl]-2-[(1S,2S)-2-(5-fluoropyridin-2-yl)-2-hydroxy-1-(pyridin-2-yl)ethyl]-2,3-dihydro-1H-isoindol-1-one (1.37 g, 99% e.e., retention time: 7.35 min (analysis condition, column: CHIRALCEL OD-H, 4.6 mmID×250 mmL, 5 μm, mobile phase: hexane/ethanol=700/300 (v/v)).

MS: [M+H]$^+$ 468.1.

Example 5 and Example 6

2-[(1R,2R)-1,2-bis(5-fluoropyridin-2-yl)-2-hydroxyethyl]-6-[5-(difluoromethyl)-1,3,4-oxadiazol-2-yl]-2,3-dihydro-1H-isoindol-1-one (Compound of Example 5)

2-[(1S,2S)-1,2-bis(5-fluoropyridin-2-yl)-2-hydroxyethyl]-6-[5-(difluoromethyl)-1,3,4-oxadiazol-2-yl]-2,3-dihydro-1H-isoindol-1-one (Compound of Example 6)

A) tert-butyl [(5-fluoropyridin-2-yl) (4-methylbenzene-1-sulfonyl)methyl]carbamate To a mixture of sodium p-toluenesulfinate (21.4 g), tert-butyl carbamate (9.36 g) and water (120 mL) was added a solution prepared by dissolving 5-fluoropyridine-2-carbaldehyde (10 g) in methanol (60 mL), at room temperature. The mixture was stirred at room temperature for 30 min until the suspension became a clear solution. To the mixture was added formic acid (6.13 mL) at room temperature, and the mixture was stirred at room temperature for 3 days. The precipitated solid was collected by filtration, washed with water and diisopropyl ether, and dried under reduced pressure to give the title compound (24.4 g).

$^1$H NMR (300 MHz, DMSO-$d_6$) 1.10-1.28 (9H, m), 2.39 (3H, s), 6.09 (1H, d, J=10.5 Hz), 7.44 (2H, d, J=7.9 Hz), 7.67 (2H, d, J=7.9 Hz), 7.81-7.97 (2H, m), 8.26 (1H, d, J=10.2 Hz), 8.56 (1H, d, J=2.3 Hz).

B) tert-butyl [1,2-bis(5-fluoropyridin-2-yl)-2-oxoethyl]carbamate

A mixture of tert-butyl [(5-fluoropyridin-2-yl) (4-methylbenzene-1-sulfonyl)methyl]carbamate (12.7 g), 5-fluoropyridine-2-carbaldehyde (4.18 g), 3-ethyl-5-(2-hydroxyethyl)-4-methylthiazolium bromide (1.68 g) and THF (134 mL) was degassed, and to the mixture was added triethylamine (69.6 mL) under argon atmosphere at room temperature. The mixture was again degassed, and the mixture was stirred overnight under argon atmosphere at 60° C. To the mixture was added saturated aqueous ammonium chloride solution at 0° C., and the mixture was partitioned between water and ethyl acetate. The separated organic layer was washed with water and saturated brine, dried over anhydrous sodium sulfate, and concentrated under reduced pressure. The residue was purified by silica gel column chromatography (NH, ethyl acetate/hexane), and crystallized from hexane/ethyl acetate to give the title compound (7.68 g).

$^1$H NMR (300 MHz, DMSO-$d_6$) δ 1.13-1.58 (9H, m), 6.74 (1H, d, J=8.7 Hz), 7.54 (1H, br d, J=8.7 Hz), 7.58-7.67 (1H, m), 7.68-7.81 (1H, m), 7.91 (1H, td, J=8.8, 2.8 Hz), 8.12 (1H, dd, J=8.7, 4.9 Hz), 8.34 (1H, d, J=2.6 Hz), 8.63 (1H, d, J=3.0 Hz).

MS: [M+H−Boc]$^+$250.0.

C) tert-butyl [(1RS,2RS)-1,2-bis(5-fluoropyridin-2-yl)-2-hydroxyethyl]carbamate

To a mixture of tert-butyl [1,2-bis(5-fluoropyridin-2-yl)-2-oxoethyl]carbamate (7.0 g) and THF (100 mL) was added dropwise potassium tri(sec-butyl)borohydride (1 M THF solution, 30.1 mL) under argon atmosphere at −78° C., and the mixture was stirred at −78° C. for 2 hr. To the mixture was added water (20 mL) at −78° C., and 2 M aqueous sodium hydroxide solution (100 mL) and 30% aqueous hydrogen peroxide (20.5 mL) were added thereto while keeping the internal temperature 0° C. or below. The mixture was stirred at room temperature for 4 hr. Sodium thiosulfate pentahydrate (49.7 g) was dissolved in water (200 mL), the obtained solution was added to the mixture at 0° C., and the mixture was stirred at room temperature for 2 hr. The mixture was extracted with ethyl acetate. The extract was washed with water and saturated brine, dried over anhydrous sodium sulfate, and concentrated under reduced pressure. The residue was purified by silica gel column chromatography (ethyl acetate/hexane), and crystallized from hexane/ethyl acetate to give the title compound (5.97 g).

$^1$H NMR (300 MHz, DMSO-$d_6$) δ 1.01-1.48 (9H, m), 4.84-4.95 (1H, m), 4.96-5.10 (1H, m), 5.67 (1H, d, J=5.6 Hz), 7.05 (1H, br d, J=9.0 Hz), 7.22-7.41 (2H, m), 7.62 (2H, td, J=8.8, 2.8 Hz), 8.40 (1H, d, J=3.0 Hz), 8.51 (1H, d, J=2.6 Hz).

MS: [M+H−Boc]$^+$252.0.

D) 2-[(1RS,2RS)-1,2-bis(5-fluoropyridin-2-yl)-2-hydroxyethyl]-6-[5-(difluoromethyl)-1,3,4-oxadiazol-2-yl]-2,3-dihydro-1H-isoindol-1-one To a mixture of tert-butyl [(1RS,2RS)-1,2-bis(5-fluoropyridin-2-yl)-2-hydroxyethyl]carbamate (4.34 g) and acetic acid (30.9 mL) was added dropwise hydrogen bromide (30% acetic acid solution (ca. 5.1 M), 19.4 mL) at room temperature, and the mixture was stirred at room temperature for 3 hr. The mixture was concentrated under reduced pressure, and the residue was subjected to azeotropy with toluene. To a mixture of the obtained residue, methyl 2-(bromomethyl)-5-(5-(difluoromethyl)-1,3,4-oxadiazol-2-yl)benzoate (4.29 g) and DMF (50 mL) was added dropwise DIPEA (21.5 mL) at 0° C., and the mixture was stirred overnight at room temperature. The mixture was poured into water, and extracted with ethyl acetate. The extract was washed with water and saturated brine, dried over anhydrous sodium sulfate, and concentrated under reduced pressure. The residue was purified by silica gel column chromatography (ethyl acetate/hexane), and crystallized from diisopropyl ether/ethyl acetate to give the title compound (3.68 g).

$^1$H NMR (300 MHz, DMSO-$d_6$) δ 4.69 (1H, d, J=18.8 Hz), 4.95 (1H, d, J=18.8 Hz), 5.49 (1H, dd, J=9.0, 5.3 Hz), 5.75 (1H, d, J=9.0 Hz), 6.05 (1H, d, J=5.3 Hz), 7.33-7.79 (5H, m), 7.84 (1H, d, J=8.3 Hz), 8.06 (1H, d, J=1.1 Hz), 8.19-8.26 (1H, m), 8.26-8.31 (1H, m), 8.62 (1H, d, J=3.0 Hz).

MS: [M+H]$^+$ 486.1.

E) 2-[(1R,2R)-1,2-bis(5-fluoropyridin-2-yl)-2-hydroxyethyl]-6-[5-(difluoromethyl)-1,3,4-oxadiazol-2-yl]-2,3-dihydro-1H-isoindol-1-one (Compound of Example 5) and

2-[(1S,2S)-1,2-bis(5-fluoropyridin-2-yl)-2-hydroxyethyl]-6-[5-(difluoromethyl)-1,3,4-oxadiazol-2-yl]-2,3-dihydro-1H-isoindol-1-one (Compound of Example 6)

2-[(1RS,2RS)-1,2-Bis(5-fluoropyridin-2-yl)-2-hydroxyethyl]-6-[5-(difluoromethyl)-1,3,4-oxadiazol-2-yl]-2,3-dihydro-1H-isoindol-1-one (3.52 g) was optically resolved by preparative HPLC (column: CHIRALCEL OD, 50 mmID×500 mmL, 20 μm, mobile phase: hexane/ethanol=700/300 (v/v)).

The fraction of the optical isomer having a longer retention time was concentrated under reduced pressure, the residue was dissolved in ethyl acetate, and the solution was passed through short silica gel column. The filtrate was concentrated under reduced pressure, and the residue was crystallized from diisopropyl ether/ethyl acetate. The obtained solid was recrystallized from heptane/ethyl acetate. The obtained solid was further recrystallized from heptane/isopropyl acetate, and dried under reduced pressure at 55-60° C. to give a white solid (1.42 g). 593 mg of the white solid was recrystallized from pentane/isopropyl acetate to give 2-[(1R,2R)-1,2-bis(5-fluoropyridin-2-yl)-2-hydroxyethyl]-6-[5-(difluoromethyl)-1,3,4-oxadiazol-2-yl]-2,3-dihydro-1H-isoindol-1-one (506 mg, 99% e.e., retention time: 7.77 min (analysis condition, column: CHIRALCEL OD-H, 4.6 mmID×250 mmL, 5 μm, mobile phase: hexane/ethanol/diethylamine=700/300/1 (v/v/v)). The absolute stereochemistry of the compound was determined by X-ray crystallography.

$^1$H NMR (300 MHz, DMSO-$d_6$) δ4.68 (1H, d, J=18.4 Hz), 4.95 (1H, d, J=18.8 Hz), 5.49 (1H, dd, J=9.0, 5.6 Hz), 5.75 (1H, d, J=9.0 Hz), 6.04 (1H, d, J=6.0 Hz), 7.34-7.80 (5H, m), 7.84 (1H, d, J=7.9 Hz), 8.05 (1H, d, J=1.1 Hz), 8.23 (1H, dd, J=7.9, 1.5 Hz), 8.27 (1H, t, J=1.5 Hz), 8.61 (1H, d, J=3.0 Hz).

MS: [M+H]$^+$ 486.1

Anal. Calcd for $C_{23}H_{15}F_4N_5O_3 \cdot 1H_2O$:C, 56.70; H, 3.14; N, 14.37. Found: C, 56.57; H, 3.21; N, 14.32.

powder X-RAY crystal diffraction pattern (diffraction angle 2θ): 6.1°, 9.0°, 15.7°, 16.4°, 18.1°, 19.9°, 21.7°, 22.5°, 24.8°, 25.3°

The fraction of the optical isomer having a shorter retention time was concentrated under reduced pressure, the residue was crystallized from diisopropyl ether/ethyl acetate, and the obtained solid was further recrystallized from heptane/isopropyl acetate, and dried under reduced pressure to give a white solid (1.54 g). 100 mg of the white solid was recrystallized from pentane/isopropyl acetate to give 2-[(1S,2S)-1,2-bis(5-fluoropyridin-2-yl)-2-hydroxyethyl]-6-[5-(difluoromethyl)-1,3,4-oxadiazol-2-yl]-2,3-dihydro-1H-isoindol-1-one (83 mg, 99% e.e., retention time: 6.43 min (analysis condition, column: CHIRALCEL OD-H, 4.6 mmID×250 mmL, 5 μm, mobile phase: hexane/ethanol/diethylamine=700/300/1 (v/v/v)).

MS: [M+H]$^+$ 486.1

Example 7 and Example 8

6-[5-(difluoromethyl)-1,3,4-oxadiazol-2-yl]-2-[(1R,2R)-2-(6-fluoropyridin-2-yl)-2-hydroxy-1-(pyridin-2-yl)ethyl]-2,3-dihydro-1H-isoindol-1-one (Compound of Example 7)

6-[5-(difluoromethyl)-1,3,4-oxadiazol-2-yl]-2-[(1S,2S)-2-(6-fluoropyridin-2-yl)-2-hydroxy-1-(pyridin-2-yl)ethyl]-2,3-dihydro-1H-isoindol-1-one (Compound of Example 8)

A) tert-butyl [2-(6-fluoropyridin-2-yl)-2-oxo-1-(pyridin-2-yl)ethyl]carbamate To a mixture of tert-butyl [(4-methylbenzene-1-sulfonyl)(pyridin-2-yl)methyl]carbamate (11.9 g), 3-ethyl-5-(2-hydroxyethyl)-4-methylthiazolium bromide (2.48 g) and THF (230 mL) was added 6-fluoropyridine-2-carbaldehyde (4.60 g) under argon atmosphere at room temperature. The mixture was degassed, and replaced with argon gas. To the mixture was added dropwise triethylamine (68.5 mL) at 60° C., and the mixture was stirred overnight under argon atmosphere at 60° C. To the mixture was added water at room temperature, and the mixture was extracted with ethyl acetate. The extract was washed with water and saturated brine, dried over anhydrous sodium sulfate, and concentrated under reduced pressure. The residue was purified by silica gel column chromatography (ethyl acetate/hexane) to give the title compound (11.4 g) as a crude product. The obtained compound was used in the next step without further purification.

MS: [M+H]$^+$ 332.1.

B) tert-butyl [(1RS,2RS)-2-(6-fluoropyridin-2-yl)-2-hydroxy-1-(pyridin-2-yl)ethyl]carbamate To a mixture of tert-butyl [2-(6-fluoropyridin-2-yl)-2-oxo-1-(pyridin-2-yl)ethyl]carbamate (11.4 g), methanol (100 mL) and THF (100 mL) was added sodium borohydride (1.49 g) at 0° C. The mixture was stirred at room temperature for 2.5 hr. To the mixture was added water at 0° C., and the mixture was extracted with ethyl acetate. The separated organic layer was washed with water and saturated brine, dried over anhydrous sodium sulfate, and concentrated under reduced pressure. The residue was crystallized from toluene, collected by filtration, and washed with diisopropyl ether. The obtained solid was recrystallized from hexane/ethyl acetate to give the title compound (6.92 g).

$^1$H NMR (300 MHz, DMSO-$d_6$) δ 1.16-1.32 (9H, m), 4.78-4.88 (1H, m), 4.90-5.01 (1H, m), 5.74 (1H, d, J=5.3 Hz), 6.95-7.10 (2H, m), 7.16-7.30 (3H, m), 7.68 (1H, t, J=6.8 Hz), 7.82-7.96 (1H, m), 8.42 (1H, d, J=4.5 Hz).

MS: [M+H]$^+$ 334.1.

C) 6-[5-(difluoromethyl)-1,3,4-oxadiazol-2-yl]-2-[(1RS,2RS)-2-(6-fluoropyridin-2-yl)-2-hydroxy-1-(pyridin-2-yl)ethyl]-2,3-dihydro-1H-isoindol-1-one To a mixture of tert-butyl [(1RS,2RS)-2-(6-fluoropyridin-2-yl)-2-hydroxy-1-(pyridin-2-yl)ethyl]carbamate (4.55 g) and acetic acid (80 mL) was added hydrogen bromide (30% acetic acid solution (ca. 5.1 M), 21.4 mL) at room temperature. The mixture was stirred at room temperature for 30 min, concentrated under reduced pressure, and subjected to azeotropy with toluene. To a mixture of the obtained residue and DMF (50 mL) was added dropwise DIPEA (13.6 mL) at 0° C., and then a solution prepared by dissolving methyl 2-(bromomethyl)-5-(5-(difluoromethyl)-1,3,4-oxadiazol-2-yl)benzoate (4.51 g) in DMF (10 mL) was added to the mixture at 0° C. The mixture was stirred at 0° C. to room temperature for 3 days. The mixture was concentrated, and to the residue was added water at room temperature. The mixture was extracted with ethyl acetate. The separated organic layer was washed with water and saturated brine, dried over anhydrous sodium sulfate, and concentrated under reduced pressure. The residue was purified by silica gel column chromatography (hexane/ethyl acetate), and crystallized from hexane/ethyl acetate to give the title compound (4.29 g).

$^1$H NMR (300 MHz, DMSO-$d_6$) δ 4.68 (1H, d, J=18.8 Hz), 4.98 (1H, d, J=18.8 Hz), 5.39-5.48 (1H, m), 5.71 (1H, d, J=9.0 Hz), 6.11 (1H, d, J=4.0 Hz), 6.95 (1H, dd, J=8.1, 2.4 Hz), 7.32-7.73 (4H, m), 7.77-7.88 (2H, m), 7.89-8.01 (1H, m), 8.06 (1H, d, J=0.9 Hz), 8.23 (1H, dd, J=8.0, 1.6 Hz), 8.58-8.67 (1H, m).

MS: [M+H]$^+$ 468.1.

D) 6-[5-(difluoromethyl)-1,3,4-oxadiazol-2-yl]-2-[(1R,2R)-2-(6-fluoropyridin-2-yl)-2-hydroxy-1-(pyridin-2-yl)ethyl]-2,3-dihydro-1H-isoindol-1-one (Compound of Example 7) and 6-[5-(difluoromethyl)-1,3,4-oxadiazol-2-yl]-2-[(1S,2S)-2-(6-fluoropyridin-2-yl)-2-hydroxy-1-(pyridin-2-yl)ethyl]-2,3-dihydro-1H-isoindol-1-one (Compound of Example 8)

6-[5-(Difluoromethyl)-1,3,4-oxadiazol-2-yl]-2-[(1RS,2RS)-2-(6-fluoropyridin-2-yl)-2-hydroxy-1-(pyridin-2-yl)ethyl]-2,3-dihydro-1H-isoindol-1-one (4.27 g) was optically resolved by preparative HPLC (column: CHIRALPAK IA, 50 mmID×500 mmL, 20 μm, mobile phase: hexane/ethanol=200/800 (v/v)).

The fraction of the optical isomer having a shorter retention time was concentrated under reduced pressure, and the residue was recrystallized from heptane/isopropyl acetate to give 6-[5-(difluoromethyl)-1,3,4-oxadiazol-2-yl]-2-[(1R,2R)-2-(6-fluoropyridin-2-yl)-2-hydroxy-1-(pyridin-2-yl)ethyl]-2,3-dihydro-1H-isoindol-1-one (1.72 g, >99% e.e., retention time: 15.49 min (analysis condition, column: CHIRALPAK IA, 4.6 mmID×250 mmL, 5 μm, mobile phase: hexane/ethanol=200/800 (v/v)). The absolute stereochemistry of the compound was determined by X-ray crystallography.

$^1$H NMR (300 MHz, DMSO-$d_6$) δ 4.68 (1H, d, J=18.8 Hz), 4.98 (1H, d, J=18.8 Hz), 5.43 (1H, dd, J=8.8, 5.8 Hz), 5.71 (1H, d, J=8.7 Hz), 6.10 (1H, d, J=6.0 Hz), 6.95 (1H, dd, J=7.9, 2.6 Hz), 7.32-7.73 (4H, m), 7.76-7.89 (2H, m), 7.89-8.00 (1H, m), 8.07 (1H, d, J=1.1 Hz), 8.23 (1H, dd, J=7.9, 1.5 Hz), 8.56-8.66 (1H, m).

MS: [M+H]$^+$ 468.1.

Anal. Calcd for $C_{23}H_{16}F_3N_5O_3 \cdot 2H_2O$: C, 58.65; H, 3.51; N, 14.87. Found: C, 58.78; H, 3.75; N, 15.00.

powder X-RAY crystal diffraction pattern (diffraction angle 2θ): 5.7°, 12.1°, 13.0°, 16.7°, 19.0°, 20.2°, 21.8°, 24.2°

The fraction of the optical isomer having a longer retention time was concentrated under reduced pressure, and the residue was recrystallized from heptane/isopropyl acetate to give 6-[5-(difluoromethyl)-1,3,4-oxadiazol-2-yl]-2-[(1S,2S)-2-(6-fluoropyridin-2-yl)-2-hydroxy-1-(pyridin-2-yl)ethyl]-2,3-dihydro-1H-isoindol-1-one (1.84 g, 99% e.e., retention time: 19.48 min (analysis condition, column: CHIRALPAK IA, 4.6 mmID×250 mmL, 5 μm, mobile phase: hexane/ethanol=200/800 (v/v)).

MS: [M+H]$^+$ 468.1.

Example 9

2-[(1R,2S)-1-cyclopropyl-2-(4-fluorophenyl)-2-hydroxyethyl]-6-[5-(difluoromethyl)-1,3,4-oxadiazol-2-yl]-2,3-dihydro-1H-isoindol-1-one A) tert-butyl {(1R)-1-cyclopropyl-2-[methoxy(methyl)amino]-2-oxoethyl}carbamate To a mixture of (2R)-((tert-butoxycarbonyl)amino)(cyclopropyl)acetic acid (10.2 g) and THF (150 mL) was added CDI (9.22 g) at 0° C., and the mixture was stirred at 0° C. for 1 hr. N-Methoxymethanamine hydrochloride (5.55 g) and DIPEA (12.4 mL) were dissolved in DMF (30 mL), and the obtained solution was added to the mixture at 0° C. The mixture was stirred overnight at room temperature. The mixture was concentrated under reduced pressure. To the residue was added water, and the mixture was extracted with ethyl acetate/THF. The separated organic layer was washed with water and saturated brine, dried over anhydrous sodium sulfate, and concentrated under reduced pressure. The residue was purified by silica gel column chromatography (hexane/ethyl acetate) to give the title compound (12.1 g).

$^1$H NMR (300 MHz, DMSO-$d_6$) δ 0.21-0.32 (1H, m), 0.33-0.49 (3H, m), 0.93-1.09 (1H, m), 1.36 (9H, s), 3.11 (3H, s), 3.70 (3H, s), 3.90-4.09 (1H, m), 7.06 (1H, d, J=8.3 Hz).

MS: [M+H−Boc]$^+$159.1.

B) tert-butyl [(1R)-1-cyclopropyl-2-(4-fluorophenyl)-2-oxoethyl]carbamate

To a mixture of tert-butyl {(1R)-1-cyclopropyl-2-[methoxy(methyl)amino]-2-oxoethyl}carbamate (8.55 g) and THF (130 mL) was added 4-fluorophenylmagnesium bromide (2 M diethyl ether solution, 42 mL) at 40° C. The mixture was stirred under nitrogen atmosphere at 40° C. for 1 hr. To the mixture was added 4-fluorophenylmagnesium bromide (2 M diethyl ether solution, 3 mL) at 40° C. The mixture was stirred under nitrogen atmosphere at 40° C. for 30 min. The mixture was poured into saturated aqueous ammonium chloride solution at 0° C. To the mixture was added water, and the mixture was extracted with ethyl acetate. The separated organic layer was washed with water and saturated brine, dried over anhydrous sodium sulfate, and concentrated under reduced pressure. The residue was purified by silica gel column chromatography (hexane/ethyl acetate) to give the title compound (7.80 g).

$^1$H NMR (300 MHz, DMSO-d$_6$) δ 0.19-0.56 (4H, m), 0.91-1.10 (1H, m), 1.13-1.50 (9H, m), 4.09-4.50 (1H, m), 7.35 (2H, t, J=8.8 Hz), 7.46 (1H, br d, J=7.2 Hz), 8.04 (2H, dd, J=8.7, 5.6 Hz).

MS: [M+H−Boc]$^+$194.1.

C) tert-butyl [(1R,2S)-1-cyclopropyl-2-(4-fluorophenyl)-2-hydroxyethyl]carbamate To a mixture of tert-butyl [(1R)-1-cyclopropyl-2-(4-fluorophenyl)-2-oxoethyl]carbamate (7.80 g), toluene (22 mL) and 2-propanol (23 mL) was added aluminium triisopropoxide (1.09 g) at room temperature. The mixture was stirred at 70° C. 3 hr. The reaction mixture was added to a mixture of 0.5 M hydrochloric acid and ethyl acetate at 0° C., and the mixture was extracted with ethyl acetate. The separated organic layer was washed with saturated aqueous sodium hydrogencarbonate solution and saturated brine, dried over anhydrous sodium sulfate, and concentrated under reduced pressure to give the title compound (7.79 g).

$^1$H NMR (300 MHz, DMSO-d$_6$) δ −0.24-−0.08 (1H, m), 0.09-0.37 (3H, m), 0.95-1.13 (1H, m), 1.26 (9H, s), 3.08-3.25 (1H, m), 4.50 (1H, t, J=5.6 Hz), 5.37 (1H, d, J=4.5 Hz), 6.45 (1H, br d, J=9.4 Hz), 7.09 (2H, t, J=9.0 Hz), 7.29-7.41 (2H, m).

D) (1S,2R)-2-amino-2-cyclopropyl-1-(4-fluorophenyl)ethan-1-ol hydrobromide

To a mixture of tert-butyl [(1R,2S)-1-cyclopropyl-2-(4-fluorophenyl)-2-hydroxyethyl]carbamate (4.79 g) and acetic acid (50 mL) was added hydrogen bromide (25% acetic acid solution, 12.5 mL) at room temperature. The mixture was stirred at room temperature for 30 min. The mixture was concentrated under reduced pressure. The residue was subjected three times to azeotropy with toluene. The residue was suspended in ethyl acetate (10 mL) and diisopropyl ether (40 mL), and the obtained suspension was stirred at room temperature for 30 min. The precipitated solid was collected by filtration, washed with diisopropyl ether/ethyl acetate (4:1), and dried to give the title compound (4.29 g).

$^1$H NMR (300 MHz, DMSO-d$_6$) δ −0.41-−0.24 (1H, m), 0.12-0.34 (2H, m), 0.34-0.50 (1H, m), 0.77-0.97 (1H, m), 2.59 (1H, dd, J=10.5, 3.0 Hz), 4.94 (1H, br s), 6.15 (1H, d, J=3.8 Hz), 7.09-7.29 (2H, m), 7.37-7.52 (2H, m), 7.89 (3H, br s).

MS: [M+H]$^+$ 196.1.

E) 2-[(1R,2S)-1-cyclopropyl-2-(4-fluorophenyl)-2-hydroxyethyl]-6-[5-(difluoromethyl)-1,3,4-oxadiazol-2-yl]-2,3-dihydro-1H-isoindol-1-one To a mixture of (1S,2R)-2-amino-2-cyclopropyl-1-(4-fluorophenyl)ethan-1-ol hydrobromide (3.65 g), DIPEA (10.5 mL) and DMF (30 mL) was added dropwise a solution prepared by dissolving methyl 2-(bromomethyl)-5-(5-(difluoromethyl)-1,3,4-oxadiazol-2-yl)benzoate (4.17 g) in DMF (12 mL), at room temperature. The mixture was stirred overnight at room temperature. To the mixture was added water at room temperature, and the mixture was extracted with ethyl acetate. The separated organic layer was washed with saturated brine, dried over anhydrous sodium sulfate, and concentrated under reduced pressure. The residue was purified by silica gel column chromatography (hexane/ethyl acetate), the obtained solid was dissolved in ethyl acetate, and the solution was filtered to remove the insoluble substance. The filtrate was concentrated under reduced pressure, and the residue was recrystallized from heptane/ethyl acetate to give the title compound (3.75 g).

$^1$H NMR (300 MHz, DMSO-d$_6$) δ−0.24-−0.11 (1H, m), −0.11-−0.01 (1H, m), 0.28-0.51 (2H, m), 1.31-1.48 (1H, m), 3.51 (1H, dd, J=10.2, 4.1 Hz), 4.78 (1H, d, J=19.2 Hz), 4.88 (1H, d, J=19.2 Hz), 5.00 (1H, t, J=4.5 Hz), 5.74 (1H, d, J=4.9 Hz), 7.05-7.21 (2H, m), 7.35-7.78 (3H, m), 7.90 (1H, d, J=8.3 Hz), 8.21 (1H, d, J=0.8 Hz), 8.29 (1H, dd, J=7.9, 1.9 Hz).

MS: [M+H]$^+$ 430.1.

Anal. Calcd for C$_{22}$H$_{18}$F$_3$N$_3$O$_3$·0.1H$_2$O: C, 61.28; H, 4.25; N, 9.75. Found: C, 61.28; H, 4.48; N, 9.77.

powder X-RAY crystal diffraction pattern (diffraction angle 2θ): 6.9°, 13.9°, 16.9°, 18.6°, 20.2°, 20.9°, 22.2°, 22.7°, 25.6°, 28.1°

The compounds of Examples are shown in the following tables. MS in the tables means actual measured value. The compounds of Examples 10-150 in the following tables were produced according to the methods described in the above-mentioned Examples, or methods analogous thereto.

TABLE 1-1

| EXAMPLE | IUPAC NAME | Structure | MS |
|---|---|---|---|
| 1 | 6-[5-(difluoromethyl)-1,3,4-oxadiazol-2-yl]-2-[(1R,2R)-2-hydroxy-1,2-di(pyridin-2-yl)ethyl]-2,3-dihydro-1H-isoindol-1-one | 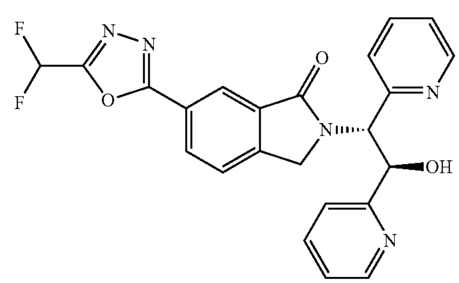 [SMILES: O=C1c2cc(-c3nnc(C(F)F)o3)ccc2CN1[C@H](c1ccccn1)[C@@H](O)c1ccccn1] | 450.2 |

TABLE 1-1-continued

| EXAMPLE | IUPAC NAME | Structure | MS |
|---|---|---|---|
| 2 | 6-[5-(difluoromethyl)-1,3,4-oxadiazol-2-yl]-2-[(1S,2S)-2-hydroxy-1,2-di(pyridin-2-yl)ethyl]-2,3-dihydro-1H-isoindol-1-one | 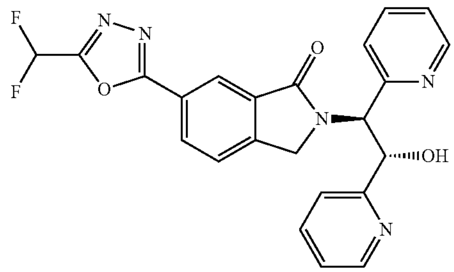 [SMILES: O=C1c2cc(-c3nnc(C(F)F)o3)ccc2CN1[C@@H](c1ccccn1)[C@H](O)c1ccccn1] | 450.2 |
| 3 | 6-[5-(difluoromethyl)-1,3,4-oxadiazol-2-yl]-2-[(1R,2R)-2-(5-fluoropyridin-2-yl)-2-hydroxy-1-(pyridin-2-yl)ethyl]-2,3-dihydro-1H-isoindol-1-one | 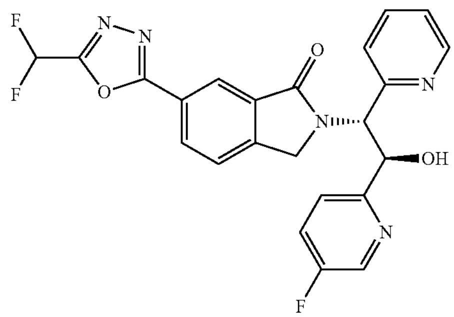 [SMILES: O=C1c2cc(-c3nnc(C(F)F)o3)ccc2CN1[C@H](c1ccccn1)[C@@H](O)c1ccc(F)cn1] | 468.1 |
| 4 | 6-[5-(difluoromethyl)-1,3,4-oxadiazol-2-yl]-2-[(1S,2S)-2-(5-fluoropyridin-2-yl)-2-hydroxy-1-(pyridin-2-yl)ethyl]-2,3-dihydro-1H-isoindol-1-one | 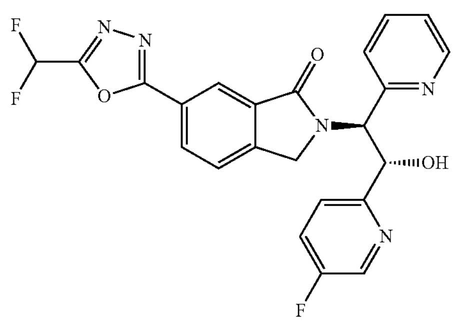 [SMILES: O=C1c2cc(-c3nnc(C(F)F)o3)ccc2CN1[C@@H](c1ccccn1)[C@H](O)c1ccc(F)cn1] | 468.2 |
| 5 | 2-[(1R,2R)-1,2-bis(5-fluoropyridin-2-yl)-2-hydroxyethyl]-6-[5-(difluoromethyl)-1,3,4-oxadiazol-2-yl]-2,3-dihydro-1H-isoindol-1-one | 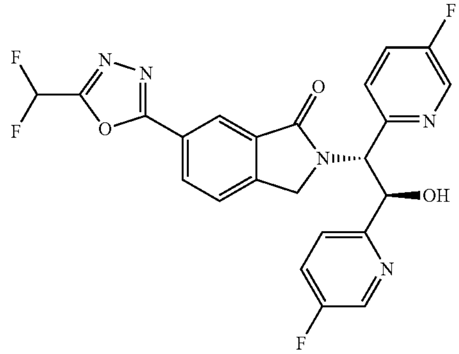 [SMILES: O=C1c2cc(-c3nnc(C(F)F)o3)ccc2CN1[C@H](c1ccc(F)cn1)[C@@H](O)c1ccc(F)cn1] | 486.1 |

TABLE 1-1-continued

| EXAMPLE | IUPAC NAME | Structure | MS |
| --- | --- | --- | --- |
| 6 | 2-[(1S,2S)-1,2-bis(5-fluoropyridin-2-yl)-2-hydroxyethyl]-6-[5-(difluoromethyl)-1,3,4-oxadiazol-2-yl]-2,3-dihydro-1H-isoindol-1-one | 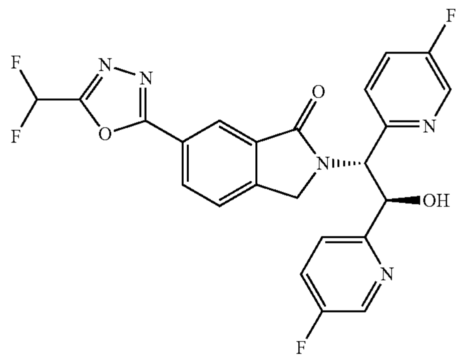 [SMILES: O=C1c2cc(-c3nnc(C(F)F)o3)ccc2CN1[C@H](c1ccc(F)cn1)[C@@H](O)c1ccc(F)cn1] | 486.1 |
| 7 | 6-[5-(difluoromethyl)-1,3,4-oxadiazol-2-yl]-2-[(1R,2R)-2-(6-fluoropyridin-2-yl)-2-hydroxy-1-(pyridin-2-yl)ethyl]-2,3-dihydro-1H-isoindol-1-one | 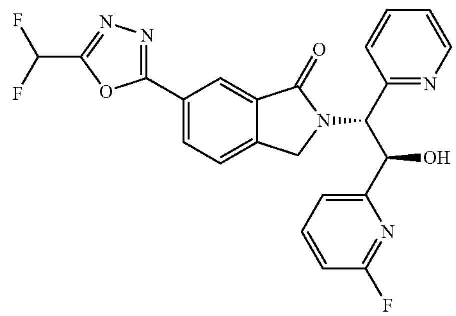 [SMILES: O=C1c2cc(-c3nnc(C(F)F)o3)ccc2CN1[C@H](c1ccccn1)[C@@H](O)c1cccc(F)n1] | 468.2 |

TABLE 1-2

| EXAMPLE | IUPAC NAME | Structure | MS |
| --- | --- | --- | --- |
| 8 | 6-[5-(difluoromethyl)-1,3,4-oxadiazol-2-yl]-2-[(1S,2S)-2-(6-fluoropyridin-2-yl)-2-hydroxy-1-(pyridin-2-yl)ethyl]-2,3-dihydro-1H-isoindol-1-one | 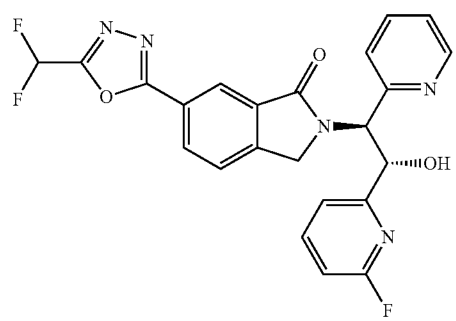 [SMILES: O=C1c2cc(-c3nnc(C(F)F)o3)ccc2CN1[C@@H](c1ccccn1)[C@H](O)c1cccc(F)n1] | 468.2 |
| 9 | 2-[(1R,2S)-1-cyclopropyl-2-(4-fluorophenyl)-2-hydroxyethyl]-6-[5-(difluoromethyl)-1,3,4-oxadiazol-2-yl]-2,3-dihydro-1H-isoindol-1-one | 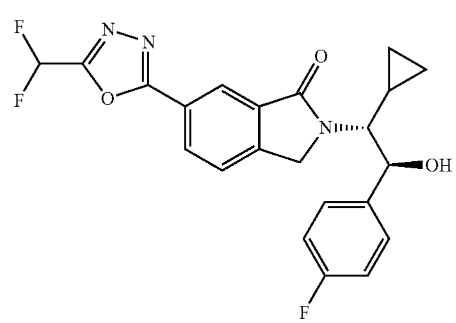 [SMILES: O=C1c2cc(-c3nnc(C(F)F)o3)ccc2CN1[C@H](C1CC1)[C@@H](O)c1ccc(F)cc1] | 430.3 |

TABLE 1-2-continued

| EXAMPLE | IUPAC NAME | Structure | MS |
|---|---|---|---|
| 10 | 2-[(1R,2S)-1-cyclopropyl-2-(3-fluorophenyl)-2-hydroxyethyl]-6-[5-(difluoromethyl)-1,3,4-oxadiazol-2-yl]-2,3-dihydro-1H-isoindol-1-one | 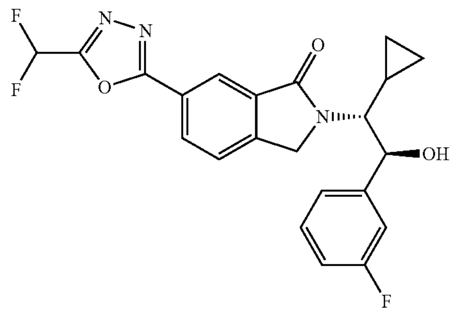 [SMILES: O=C1c2cc(-c3nnc(C(F)F)o3)ccc2CN1[C@H](C1CC1)[C@@H](O)c1cccc(F)c1] | 430.1 |
| 11 | 6-[5-(difluoromethyl)-1,3,4-oxadiazol-2-yl]-2-[(1R,2S)-2-hydroxy-1,2-diphenylethyl]-2,3-dihydro-1H-isoindol-1-one | 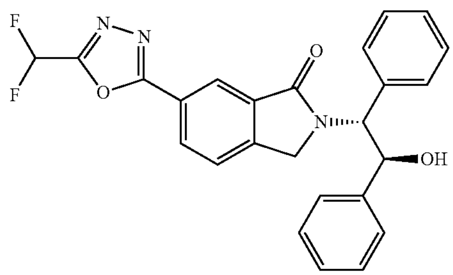 [SMILES: O=C1c2cc(-c3nnc(C(F)F)o3)ccc2CN1[C@H](c1ccccc1)[C@@H](O)c1ccccc1] | 446.2 |
| 12 | 6-[5-(difluoromethyl)-1,3,4-oxadiazol-2-yl]-2-[(1R,2R)-2-hydroxy-1,2-diphenylethyl]-2,3-dihydro-1H-isoindol-1-one | 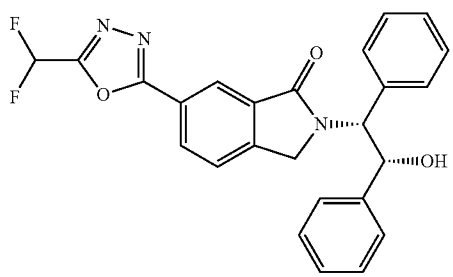 [SMILES: O=C1c2cc(-c3nnc(C(F)F)o3)ccc2CN1[C@H](c1ccccc1)[C@H](O)c1ccccc1] | 448.2 |
| 13 | 6-[5-(difluoromethyl)-1,3,4-oxadiazol-2-yl]-2-[(1S,2S)-2-hydroxy-1,2-diphenylethyl]-2,3-dihydro-1H-isoindol-1-one | 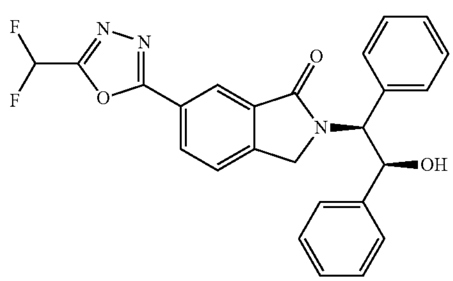 [SMILES: O=C1c2cc(-c3nnc(C(F)F)o3)ccc2CN1[C@@H](c1ccccc1)[C@@H](O)c1ccccc1] | 448.2 |
| 14 | 6-[5-(difluoromethyl)-1,3,4-oxadiazol-2-yl]-2-[(1S,2R)-2-hydroxy-1,2-diphenylethyl]-2,3-dihydro-1H-isoindol-1-one | 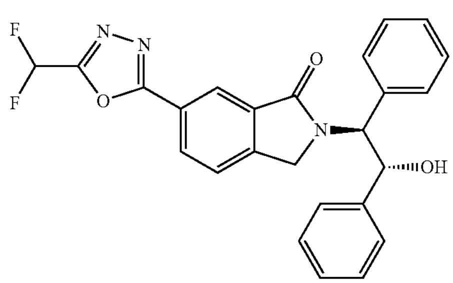 [SMILES: O=C1c2cc(-c3nnc(C(F)F)o3)ccc2CN1[C@@H](c1ccccc1)[C@H](O)c1ccccc1] | 448.2 |

TABLE 1-3

| EXAMPLE | IUPAC NAME | Structure | MS |
|---|---|---|---|
| 15 | 6-[5-(difluoromethyl)-1,3,4-oxadiazol-2-yl]-2-[(1RS,2RS)-2-hydroxy-2-(pyridin-2-yl)-1-(3,4,5-trifluorophenyl)ethyl]-2,3-dihydro-1H-isoindol-1-one | 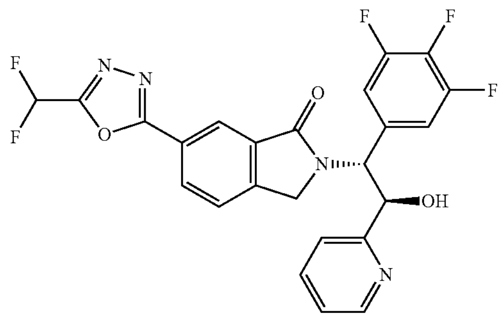 [SMILES: O=C1c2cc(-c3nnc(C(F)F)o3)ccc2CN1[C@H](c1cc(F)c(F)c(F)c1)[C@@H](O)c1ccccn1] | 503.1 |
| 16 | 6-[5-(difluoromethyl)-1,3,4-oxadiazol-2-yl]-2-[(1RS,2SR)-2-(3-fluorophenyl)-1-(4-fluorophenyl)-2-hydroxyethyl]-2,3-dihydro-1H-isoindol-1-one | 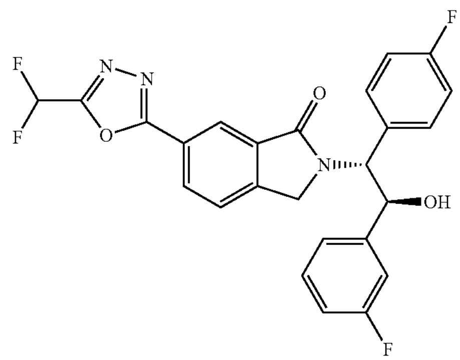 [SMILES: O=C1c2cc(-c3nnc(C(F)F)o3)ccc2CN1[C@H](c1ccc(F)cc1)[C@@H](O)c1cccc(F)c1] | 484.2 |
| 17 | 6-[5-(difluoromethyl)-1,3,4-oxadiazol-2-yl]-2-{(1RS,2SR)-2-hydroxy-2-phenyl-1-[6-(trifluoromethyl)pyridin-3-yl]ethyl}-2,3-dihydro-1H-isoindol-1-one | 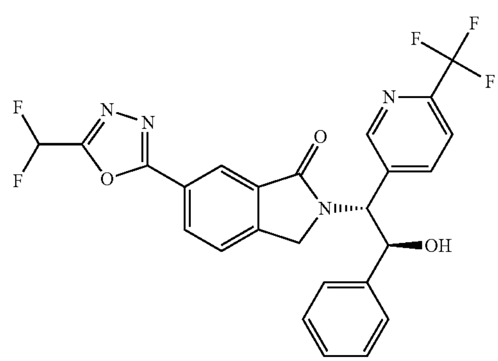 | 517.2 |
| 18 | 6-[5-(difluoromethyl)-1,3,4-oxadiazol-2-yl]-2-{(1RS,2SR)-2-(4-fluorophenyl)-2-hydroxy-1-[6-(trifluoromethyl)pyridin-3-yl]ethyl}-2,3-dihydro-1H-isoindol-1-one | 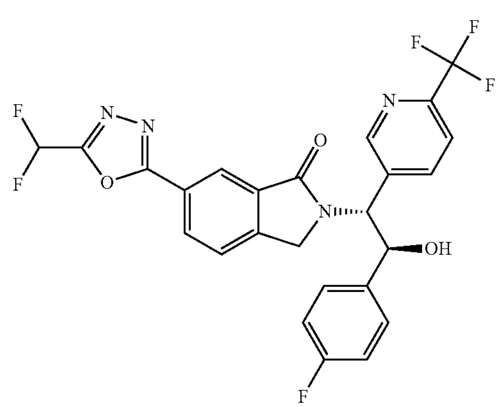 [SMILES: O=C1c2cc(-c3nnc(C(F)F)o3)ccc2CN1[C@H](c1ccc(C(F)(F)F)nc1)[C@@H](O)c1ccc(F)cc1] | 535.1 |

TABLE 1-3-continued

| EXAMPLE | IUPAC NAME | Structure | MS |
|---|---|---|---|
| 19 | 2-[(1RS,2SR)-2-cyclopropyl-1-(4-fluorophenyl)-2-hydroxyethyl]-6-[5-(difluoromethyl)-1,3,4-oxadiazol-2-yl]-2,3-dihydro-1H-isoindol-1-one | 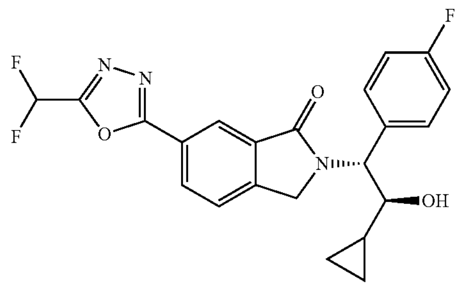 [SMILES: O=C1c2cc(-c3nnc(C(F)F)o3)ccc2CN1[C@H](c1ccc(F)cc1)[C@@H](O)C1CC1] | 428.2 |
| 20 | 6-[5-(difluoromethyl)-1,3,4-oxadiazol-2-yl]-2-[(1RS,2SR)-1-(3-fluorophenyl)-2-hydroxy-2-phenylethyl]-2,3-dihydro-1H-isoindol-1-one | 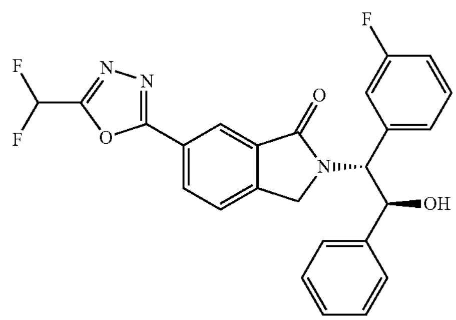 [SMILES: O=C1c2cc(-c3nnc(C(F)F)o3)ccc2CN1[C@H](c1cccc(F)c1)[C@@H](O)c1ccccc1] | 466.1 |
| 21 | 6-[5-(difluoromethyl)-1,3,4-oxadiazol-2-yl]-2-[(1RS,2SR)-1-(3-fluorophenyl)-2-(4-fluorophenyl)-2-hydroxyethyl]-2,3-dihydro-1H-isoindol-1-one | 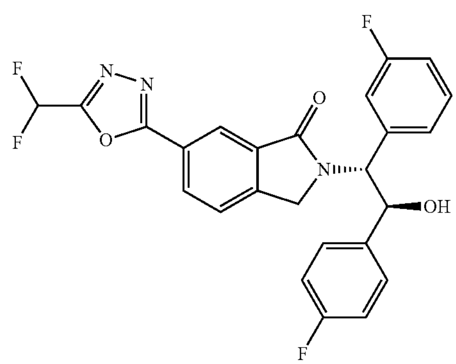 [SMILES: O=C1c2cc(-c3nnc(C(F)F)o3)ccc2CN1[C@H](c1cccc(F)c1)[C@@H](O)c1ccc(F)cc1] | 484.1 |

TABLE 1-4

| EXAMPLE | IUPAC NAME | Structure | MS |
|---|---|---|---|
| 22 | 6-[5-(difluoromethyl)-1,3,4-oxadiazol-2-yl]-2-[(1RS,2SR)-2-(4-fluorophenyl)-2-hydroxy-1-phenylethyl]-2,3-dihydro-1H-isoindol-1-one | 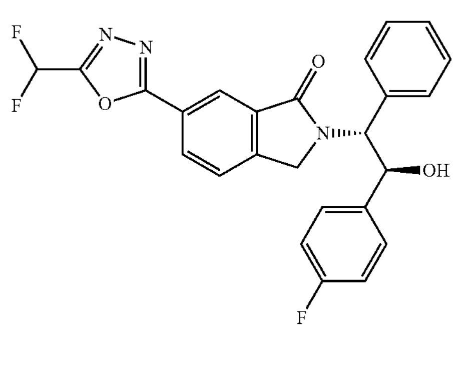 [SMILES: O=C1c2cc(-c3nnc(C(F)F)o3)ccc2CN1[C@H](c1ccccc1)[C@@H](O)c1ccc(F)cc1] | 466.1 |

TABLE 1-4-continued

| EXAMPLE | IUPAC NAME | Structure | MS |
|---|---|---|---|
| 23 | 6-[5-(difluoromethyl)-1,3,4-oxadiazol-2-yl]-2-[(1RS,2SR)-2-(3-fluorophenyl)-2-hydroxy-1-phenylethyl]-2,3-dihydro-1H-isoindol-1-one | 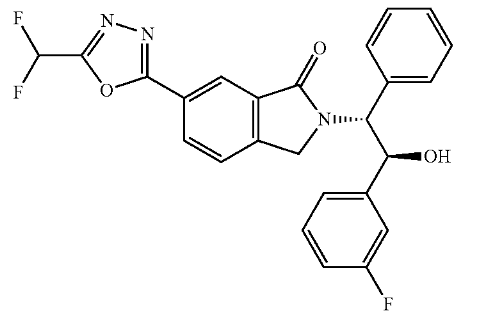 [SMILES: O=C1c2cc(-c3nnc(C(F)F)o3)ccc2CN1[C@H](c1ccccc1)[C@@H](O)c1cccc(F)c1] | 466.1 |
| 24 | 6-[5-(difluoromethyl)-1,3,4-oxadiazol-2-yl]-2-{(1RS,2RS)-2-hydroxy-2-(pyridin-2-yl)-1-[3-(trifluoromethyl)phenyl]ethyl}-2,3-dihydro-1H-isoindol-1-one | 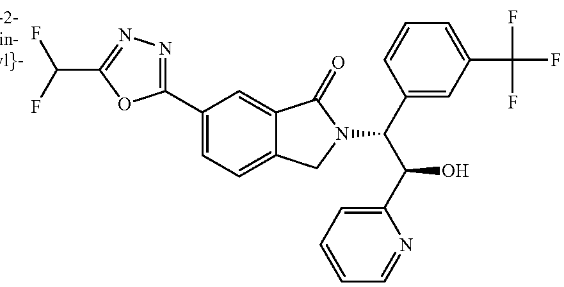 | 517.0 |
| 25 | 2-[(1RS,2SR)-2-(4,4-difluorocyclohexyl)-2-hydroxy-1-phenylethyl]-6-[5-(difluoromethyl)-1,3,4-oxadiazol-2-yl]-2,3-dihydro-1H-isoindol-1-one | 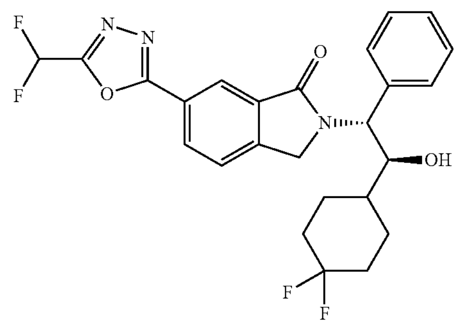 [SMILES: O=C1c2cc(-c3nnc(C(F)F)o3)ccc2CN1[C@H](c1ccccc1)[C@@H](O)C1CCC(F)(F)CC1] | 490.1 |
| 26 | 6-[5-(difluoromethyl)-1,3,4-oxadiazol-2-yl]-2-{(1RS,2RS)-2-hydroxy-2-(pyridin-2-yl)-1-[4-(trifluoromethyl)phenyl]ethyl}-2,3-dihydro-1H-isoindol-1-one | 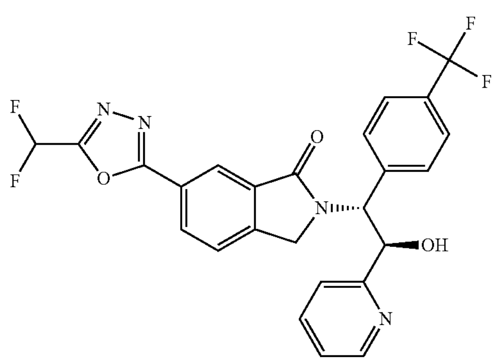 [SMILES: O=C1c2cc(-c3nnc(C(F)F)o3)ccc2CN1[C@H](c1ccc(C(F)(F)F)cc1)[C@@H](O)c1ccccn1] | 517.1 |
| 27 | 6-[5-(difluoromethyl)-1,3,4-oxadiazol-2-yl]-2-[(1RS,2SR)-1-(2-fluorophenyl)-2-hydroxy-2-phenylethyl]-2,3-dihydro-1H-isoindol-1-one | 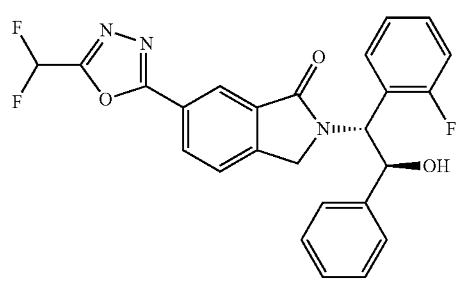 [SMILES: O=C1c2cc(-c3nnc(C(F)F)o3)ccc2CN1[C@H](c1ccccc1F)[C@@H](O)c1ccccc1] | 466.1 |

TABLE 1-4-continued

| EXAMPLE | IUPAC NAME | Structure | MS |
|---|---|---|---|
| 28 | 6-[5-(difluoromethyl)-1,3,4-oxadiazol-2-yl]-2-[(1RS,2SR)-1-(2-fluorophenyl)-2-(4-fluorophenyl)-2-hydroxyethyl]-2,3-dihydro-1H-isoindol-1-one | 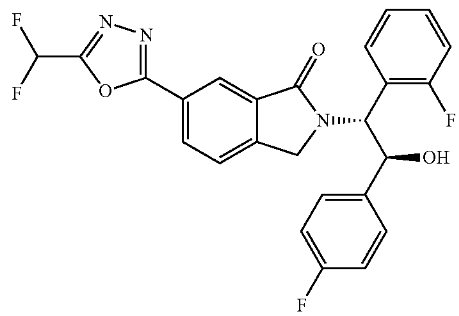 [SMILES: O=C1c2cc(-c3nnc(C(F)F)o3)ccc2CN1[C@H](c1ccccc1F)[C@@H](O)c1ccc(F)cc1] | 484.1 |

TABLE 1-5

| EXAMPLE | IUPAC NAME | Structure | MS |
|---|---|---|---|
| 29 | 6-[5-(difluoromethyl)-1,3,4-oxadiazol-2-yl]-2-[(1RS,2SR)-2-(2-fluorophenyl)-1-(4-fluorophenyl)-2-hydroxyethyl]-2,3-dihydro-1H-isoindol-1-one | 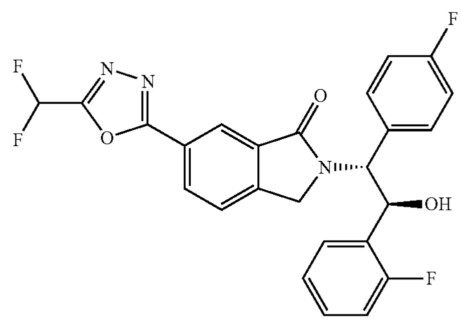 [SMILES: O=C1c2cc(-c3nnc(C(F)F)o3)ccc2CN1[C@H](c1ccc(F)cc1)[C@@H](O)c1ccccc1F] | 484.1 |
| 30 | 6-[5-(difluoromethyl)-1,3,4-oxadiazol-2-yl]-2-[(1RS,2SR)-1-(4-fluorophenyl)-2-hydroxy-2-(oxan-4-yl)ethyl]-2,3-dihydro-1H-isoindol-1-one | 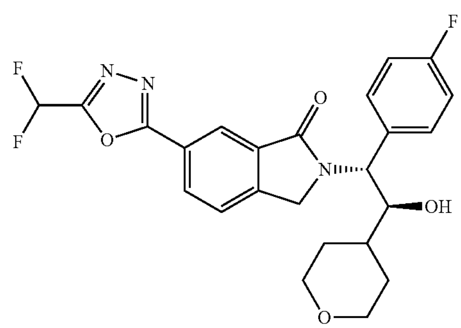 [SMILES: O=C1c2cc(-c3nnc(C(F)F)o3)ccc2CN1[C@H](c1ccc(F)cc1)[C@@H](O)C1CCOCC1] | 474.2 |
| 31 | 6-[5-(difluoromethyl)-1,3,4-oxadiazol-2-yl]-2-[(1RS,2RS)-1-(2,4-difluorophenyl)-2-hydroxy-2-(pyridin-2-yl)ethyl]-2,3-dihydro-1H-isoindol-1-one | 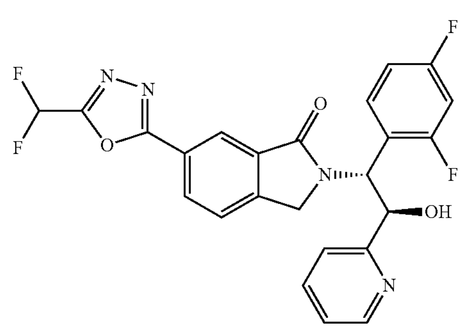 [SMILES: O=C1c2cc(-c3nnc(C(F)F)o3)ccc2CN1[C@H](c1ccc(F)cc1F)[C@@H](O)c1ccccn1] | 485.1 |

TABLE 1-5-continued

| EXAMPLE | IUPAC NAME | Structure | MS |
|---|---|---|---|
| 32 | 6-[5-(difluoromethyl)-1,3,4-oxadiazol-2-yl]-2-[(1R*,2S*)-1-(2,4-difluorophenyl)-2-(4-fluorophenyl)-2-hydroxyethyl]-2,3-dihydro-1H-isoindol-1-one (Enantiomer 1) | 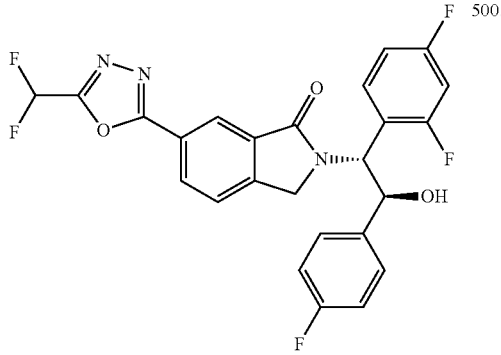 | 500.1 |
| 33 | 6-[5-(difluoromethyl)-1,3,4-oxadiazol-2-yl]-2-[(1R*,2S*)-1-(2,4-difluorophenyl)-2-(4-fluorophenyl)-2-hydroxyethyl]-2,3-dihydro-1H-isoindol-1-one (Enantiomer 2) | 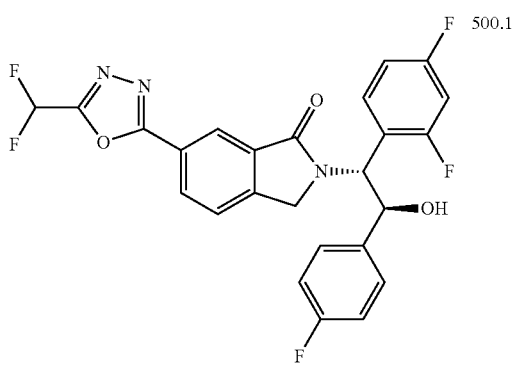 | 500.1 |
| 34 | 6-[5-(difluoromethyl)-1,3,4-oxadiazol-2-yl]-2-[(1R*,2S*)-2-(4-fluorophenyl)-1-(6-fluoropyridin-3-yl)-2-hydroxyethyl]-2,3-dihydro-1H-isoindol-1-one (Enantiomer 1) | 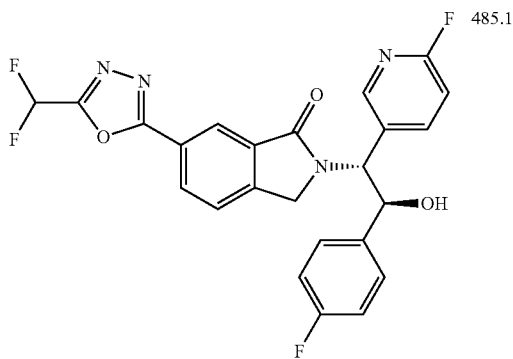 | 485.1 |
| 35 | 6-[5-(difluoromethyl)-1,3,4-oxadiazol-2-yl]-2-[(1R*,2S*)-2-(4-fluorophenyl)-1-(6-fluoropyridin-3-yl)-2-hydroxyethyl]-2,3-dihydro-1H-isoindol-1-one (Enantiomer 2) | 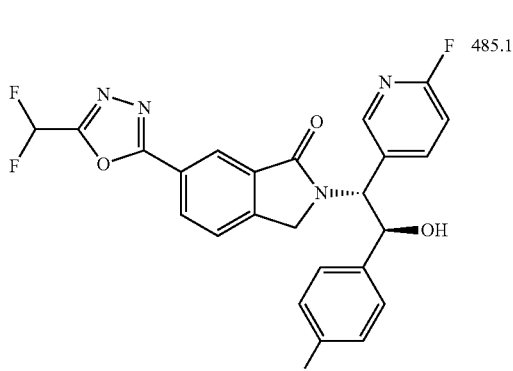 | 485.1 |

TABLE 1-6

| EXAMPLE | IUPAC NAME | Structure | MS |
|---|---|---|---|
| 36 | 6-[5-(difluoromethyl)-1,3,4-oxadiazol-2-yl]-2-[(1R*,2S*)-2-(4-fluorophenyl)-2-hydroxy-1-(pyridin-2-yl)ethyl]-2,3-dihydro-1H-isoindol-1-one (Enantiomer 1) | 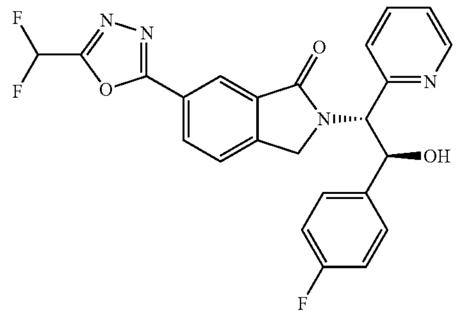 [SMILES: O=C1c2cc(-c3nnc(C(F)F)o3)ccc2CN1[C@H](c1ccccn1)[C@@H](O)c1ccc(F)cc1] | 467.1 |
| 37 | 6-[5-(difluoromethyl)-1,3,4-oxadiazol-2-yl]-2-[(1R*,2S*)-2-(4-fluorophenyl)-2-hydroxy-1-(pyridin-2-yl)ethyl]-2,3-dihydro-1H-isoindol-1-one (Enantiomer 2) | 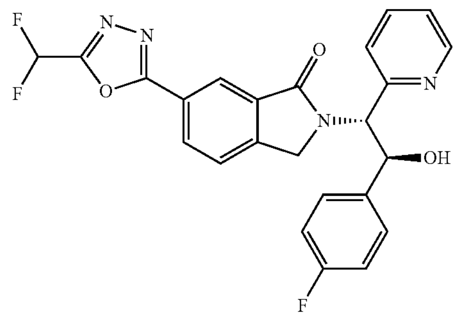 [SMILES: O=C1c2cc(-c3nnc(C(F)F)o3)ccc2CN1[C@H](c1ccccn1)[C@@H](O)c1ccc(F)cc1] | 467.1 |
| 38 | 2-[(1R,2R)-1-cyclopropyl-2-hydroxy-2-(pyridin-2-yl)ethyl]-6-[5-(difluoromethyl)-1,3,4-oxadiazol-2-yl]-2,3-dihydro-1H-isoindol-1-one | 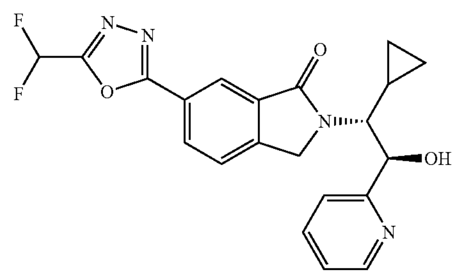 | 413.2 |
| 39 | 6-[5-(difluoromethyl)-1,3,4-oxadiazol-2-yl]-2-{(1RS,2RS)-2-hydroxy-2-(pyridin-2-yl)-1-[2-(trifluoromethyl)phenyl]ethyl}-2,3-dihydro-1H-isoindol-1-one | 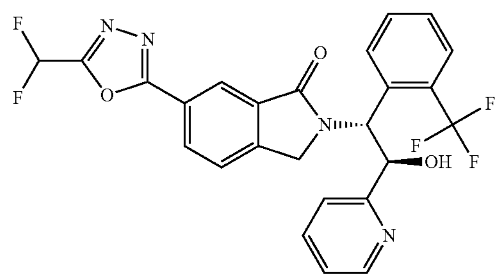 [SMILES: O=C1c2cc(-c3nnc(C(F)F)o3)ccc2CN1[C@H](c1ccccc1C(F)(F)F)[C@@H](O)c1ccccn1] | 517.1 |
| 40 | 3-[(1RS,2SR)-1-{6-[5-(difluoromethyl)-1,3,4-oxadiazol-2-yl]-1-oxo-1,3-dihydro-2H-isoindol-2-yl}-2-hydroxy-2-phenylethyl]benzonitrile | 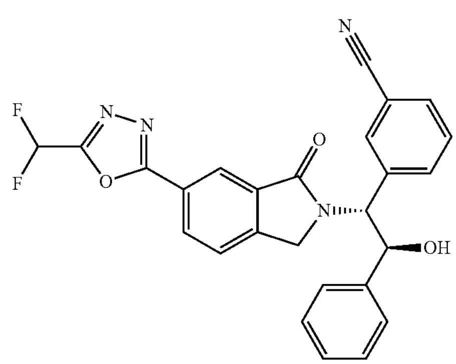 [SMILES: N#Cc1cccc([C@H]([C@@H](O)c2ccccc2)N2Cc3ccc(-c4nnc(C(F)F)o4)cc3C2=O)c1] | 471.2 |

TABLE 1-6-continued

| EXAMPLE | IUPAC NAME | Structure | MS |
|---|---|---|---|
| 41 | 4-[(1RS,2SR)-1-{6-[5-(difluoromethyl)-1,3,4-oxadiazol-2-yl]-1-oxo-1,3-dihydro-2H-isoindol-2-yl}-2-hydroxy-2-phenylethyl]benzonitrile | 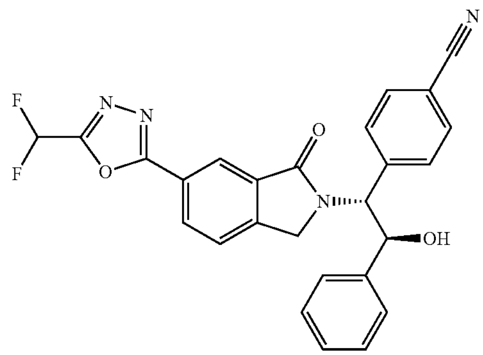 [SMILES: N#Cc1ccc([C@H]([C@@H](O)c2ccccc2)N2Cc3ccc(-c4nnc(C(F)F)o4)cc3C2=O)cc1] | 471.1 |
| 42 | 6-[5-(difluoromethyl)-1,3,4-oxadiazol-2-yl]-2-[(1RS,2SR)-2-hydroxy-1-(1-methyl-1H-pyrazol-4-yl)-2-phenylethyl]-2,3-dihydro-1H-isoindol-1-one | 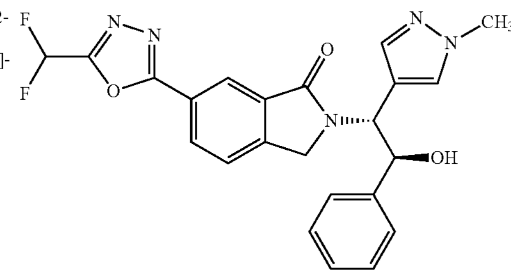 | 452.1 |

TABLE 1-7

| EXAMPLE | IUPAC NAME | Structure | MS |
|---|---|---|---|
| 43 | 6-[5-(difluoromethyl)-1,3,4-oxadiazol-2-yl]-2-[(1RS,2SR)-2-(4-fluorophenyl)-2-hydroxy-1-(1-methyl-1H-pyrazol-4-yl)ethyl]-2,3-dihydro-1H-isoindol-1-one | 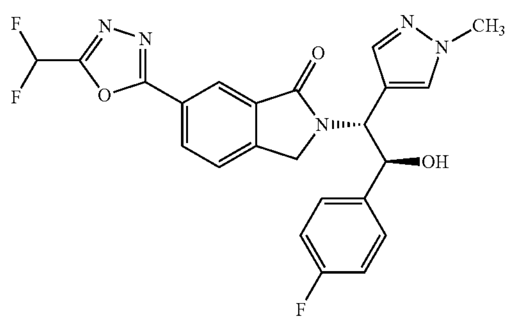 [SMILES: Cn1cc([C@H]([C@@H](O)c2ccc(F)cc2)N2Cc3ccc(-c4nnc(C(F)F)o4)cc3C2=O)cn1] | 468.2 |
| 44 | 6-[5-(difluoromethyl)-1,3,4-oxadiazol-2-yl]-2-[(1RS,2SR)-2-(6-ethoxypyridin-3-yl)-2-hydroxy-1-phenylethyl]-2,3-dihydro-1H-isoindol-1-one | 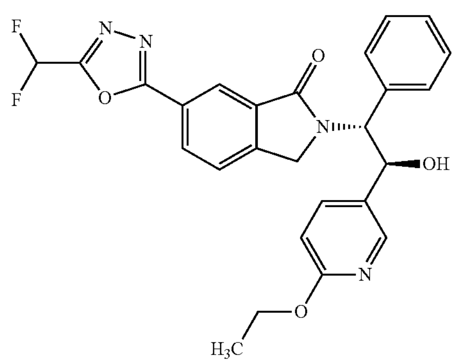 [SMILES: CCOc1ccc([C@H](O)[C@@H](c2ccccc2)N2Cc3ccc(-c4nnc(C(F)F)o4)cc3C2=O)cn1] | 493.1 |

TABLE 1-7-continued

| EXAMPLE | IUPAC NAME | Structure | MS |
|---|---|---|---|
| 45 | 6-[5-(difluoromethyl)-1,3,4-oxadiazol-2-yl]-2-[(1R*,2S*)-1-(4-fluorophenyl)-2-hydroxy-2-phenylethyl]-2,3-dihydro-1H-isoindol-1-one (Enantiomer 1) | 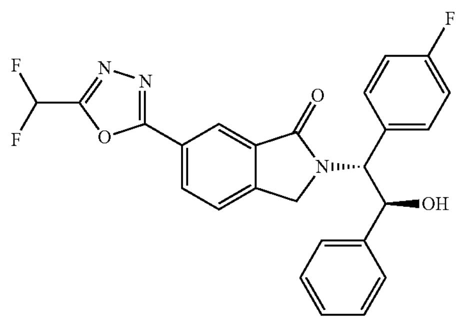 [SMILES: O=C1c2cc(-c3nnc(C(F)F)o3)ccc2CN1[C@H](c1ccc(F)cc1)[C@@H](O)c1ccccc1] | 464.2 |
| 46 | 6-[5-(difluoromethyl)-1,3,4-oxadiazol-2-yl]-2-[(1R*,2S*)-1-(4-fluorophenyl)-2-hydroxy-2-phenylethyl]-2,3-dihydro-1H-isoindol-1-one (Enantiomer 2) | 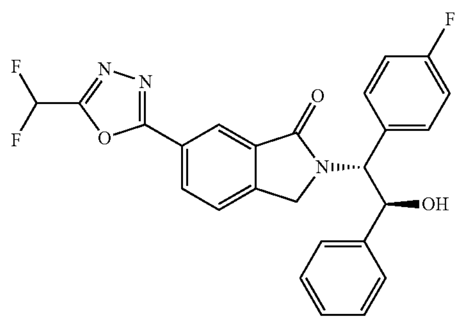 [SMILES: O=C1c2cc(-c3nnc(C(F)F)o3)ccc2CN1[C@H](c1ccc(F)cc1)[C@@H](O)c1ccccc1] | 464.2 |
| 47 | 6-[5-(difluoromethyl)-1,3,4-oxadiazol-2-yl]-2-[(1R*,2R*)-2-hydroxy-1-phenyl-2-(pyridin-2-yl)ethyl]-2,3-dihydro-1H-isoindol-1-one (Enantiomer 1) | 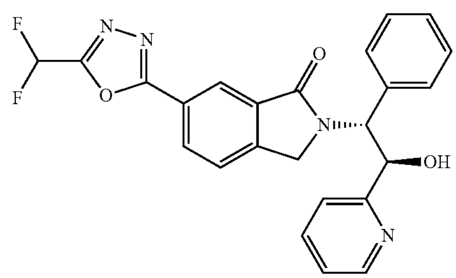 [SMILES: O=C1c2cc(-c3nnc(C(F)F)o3)ccc2CN1[C@H](c1ccccc1)[C@@H](O)c1ccccn1] | 449.2 |
| 48 | 6-[5-(difluoromethyl)-1,3,4-oxadiazol-2-yl]-2-[(1R*,2R*)-2-hydroxy-1-phenyl-2-(pyridin-2-yl)ethyl]-2,3-dihydro-1H-isoindol-1-one (Enantiomer 2) | 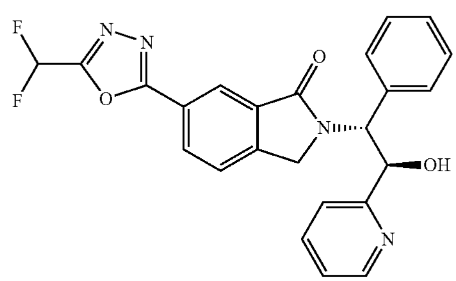 | 449.2 |
| 49 | 6-[5-(difluoromethyl)-1,3,4-oxadiazol-2-yl]-2-[(1R*,2S*)-1-(4-fluorophenyl)-2-hydroxy-2-(pyridin-3-yl)ethyl]-2,3-dihydro-1H-isoindol-1-one (Enantiomer 2) | 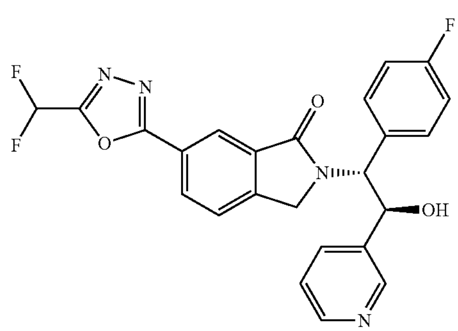 [SMILES: O=C1c2cc(-c3nnc(C(F)F)o3)ccc2CN1[C@H](c1ccc(F)cc1)[C@@H](O)c1cccnc1] | 467.1 |

TABLE 1-8

| EXAMPLE | IUPAC NAME | Structure | MS |
|---|---|---|---|
| 50 | 6-[5-(difluoromethyl)-1,3,4-oxadiazol-2-yl]-2-[(1R*,2R*)-1-(3,4-difluorophenyl)-2-hydroxy-2-(pyridin-2-yl)ethyl]-2,3-dihydro-1H-isoindol-1-one (Enantiomer 1) | 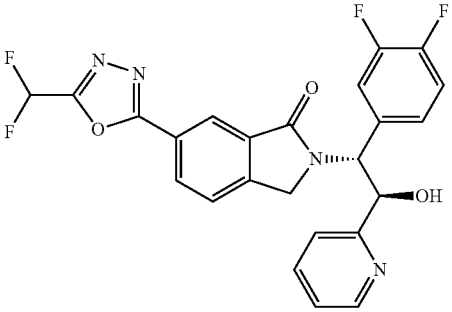 [SMILES: O=C1c2cc(-c3nnc(C(F)F)o3)ccc2CN1[C@H](c1ccc(F)c(F)c1)[C@@H](O)c1ccccn1] | 485.1 |
| 51 | 6-[5-(difluoromethyl)-1,3,4-oxadiazol-2-yl]-2-[(1R*,2R*)-1-(3,4-difluorophenyl)-2-hydroxy-2-(pyridin-2-yl)ethyl]-2,3-dihydro-1H-isoindol-1-one (Enantiomer 2) | 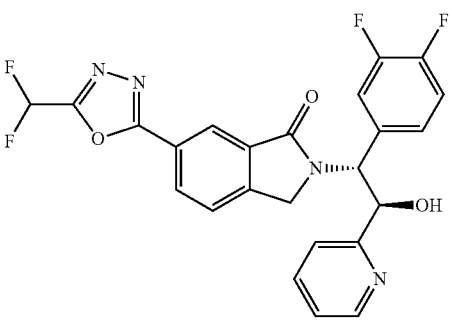 | 485.1 |
| 52 | 6-[5-(difluoromethyl)-1,3,4-oxadiazol-2-yl]-2-[(1R*,2S*)-1-(4-fluorophenyl)-2-hydroxy-2-(pyridin-3-yl)ethyl]-2,3-dihydro-1H-isoindol-1-one (Enantiomer 1) | 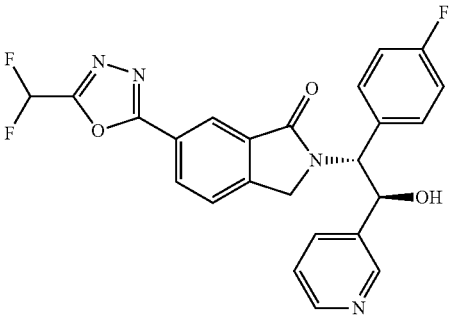 [SMILES: O=C1c2cc(-c3nnc(C(F)F)o3)ccc2CN1[C@H](c1ccc(F)cc1)[C@@H](O)c1cccnc1] | 467.1 |
| 53 | 6-[5-(difluoromethyl)-1,3,4-oxadiazol-2-yl]-2-[(1RS,2SR)-2-(3,4-difluorophenyl)-1-(6-ethoxypyridin-3-yl)-2-hydroxyethyl]-2,3-dihydro-1H-isoindol-1-one | 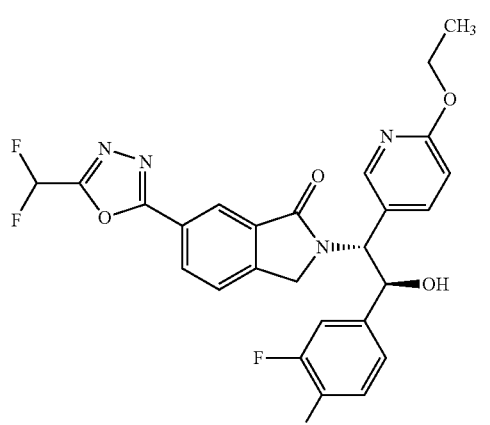 | 529.1 |

TABLE 1-8-continued

| EXAMPLE | IUPAC NAME | Structure | MS |
|---|---|---|---|
| 54 | 6-[5-(difluoromethyl)-1,3,4-oxadiazol-2-yl]-2-{(1R*,2S*)-1-(4-fluorophenyl)-2-hydroxy-2-[6-(trifluoromethyl)pyridin-3-yl]ethyl}-2,3-dihydro-1H-isoindol-1-one (Enantiomer 1) | 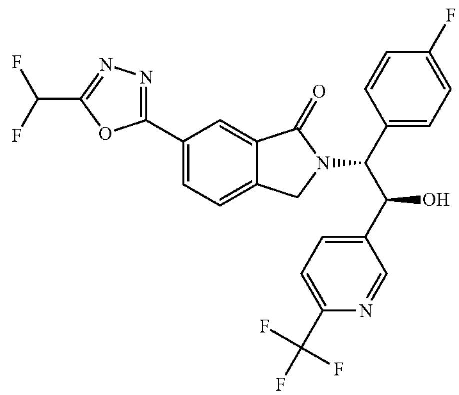 [SMILES: O=C1c2cc(-c3nnc(C(F)F)o3)ccc2CN1[C@H](c1ccc(F)cc1)[C@@H](O)c1ccc(C(F)(F)F)nc1] | 533.1 |
| 55 | 6-[5-(difluoromethyl)-1,3,4-oxadiazol-2-yl]-2-{(1R*,2S)-1-(4-fluorophenyl)-2-hydroxy-2-[6-(trifluoromethyl)pyridin-3-yl]ethyl}-2,3-dihydro-1H-isoindol-1-one (Enantiomer 2) | 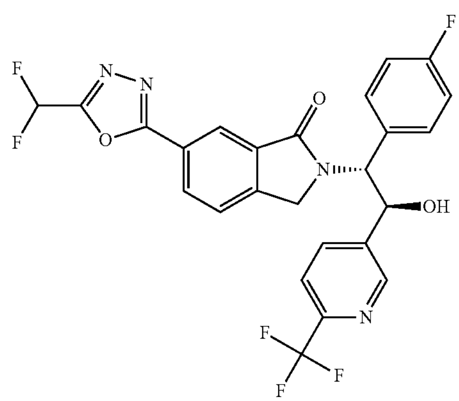 [SMILES: O=C1c2cc(-c3nnc(C(F)F)o3)ccc2CN1[C@H](c1ccc(F)cc1)[C@@H](O)c1ccc(C(F)(F)F)nc1] | 533.2 |
| 56 | 6-[5-(difluoromethyl)-1,3,4-oxadiazol-2-yl]-2-[(1RS,2SR)-2-(3,4-difluorophenyl)-1-(6-fluoropyridin-3-yl)-2-hydroxyethyl]-2,3-dihydro-1H-isoindol-1-one | 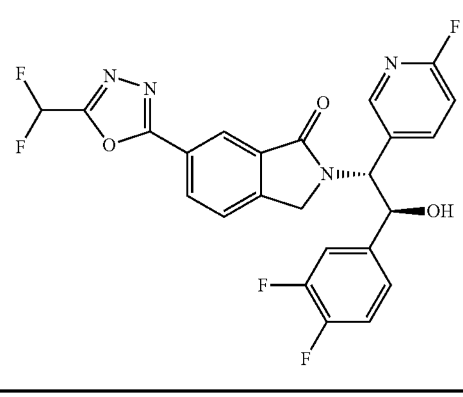 | 501.2 |

TABLE 1-9

| EXAMPLE | IUPAC NAME | Structure | MS |
|---|---|---|---|
| 57 | 2-[(1R,2R)-1-cyclopropyl-2-(5-fluoropyridin-2-yl)-2-hydroxyethyl]-6-[5-(difluoromethyl)-1,3,4-oxadiazol-2-yl]-2,3-dihydro-1H-isoindol-1-one | 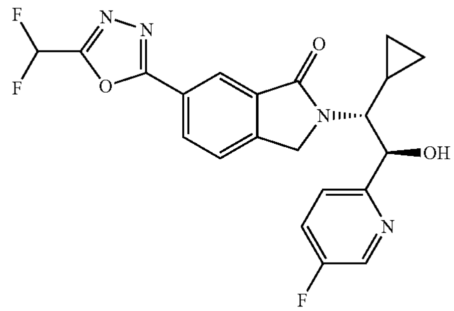 [SMILES: O=C1c2cc(-c3nnc(C(F)F)o3)ccc2CN1[C@H](C1CC1)[C@@H](O)c1ccc(F)cn1] | 431.2 |
| 58 | 6-[5-(difluoromethyl)-1,3,4-oxadiazol-2-yl]-2-[(1RS,2SR)-1-(4-fluorophenyl)-2-(6-fluoropyridin-3-yl)-2-hydroxyethyl]-2,3-dihydro-1H-isoindol-1-one | 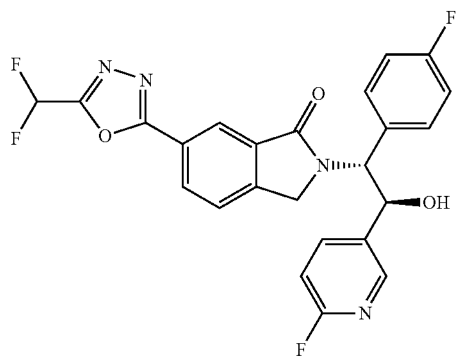 [SMILES: O=C1c2cc(-c3nnc(C(F)F)o3)ccc2CN1[C@H](c1ccc(F)cc1)[C@@H](O)c1ccc(F)nc1] | 483.2 |
| 59 | 6-[5-(difluoromethyl)-1,3,4-oxadiazol-2-yl]-2-[(1R*,2R*)-1-(5-fluoropyridin-2-yl)-2-hydroxy-2-(pyridin-2-yl)ethyl]-2,3-dihydro-1H-isoindol-1-one (Enantiomer 1) | 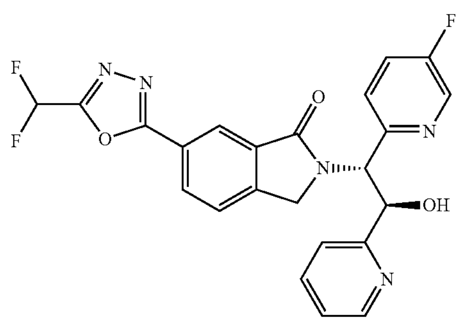 [SMILES: O=C1c2cc(-c3nnc(C(F)F)o3)ccc2CN1[C@H](c1ccc(F)cn1)[C@@H](O)c1ccccn1] | 468.2 |
| 60 | 6-[5-(difluoromethyl)-1,3,4-oxadiazol-2-yl]-2-[(1R*,2R*)-2-(5-fluoropyridin-2-yl)-2-hydroxy-2-(pyridin-2-yl)ethyl]-2,3-dihydro-1H-isoindol-1-one (Enantiomer 2) | 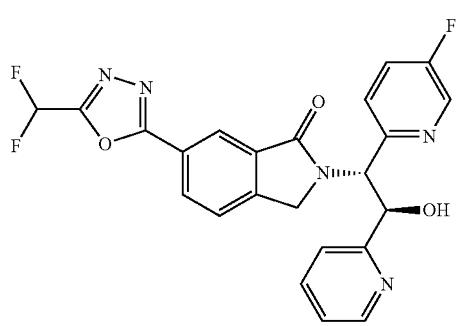 [SMILES: O=C1c2cc(-c3nnc(C(F)F)o3)ccc2CN1[C@H](c1ccc(F)cn1)[C@@H](O)c1ccccn1] | 468.2 |

TABLE 1-9-continued

| EXAMPLE | IUPAC NAME | Structure | MS |
|---|---|---|---|
| 61 | 6-[5-(difluoromethyl)-1,3,4-oxadiazol-2-yl]-2-[(1R*,2S*)-2-(3-fluorophenyl)-2-hydroxy-1-(pyridin-2-yl)ethyl]-2,3-dihydro-1H-isoindol-1-one (Enantiomer 1) | 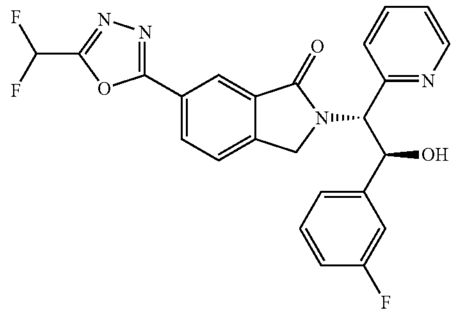 [SMILES: O=C1c2cc(-c3nnc(C(F)F)o3)ccc2CN1[C@H](c1ccccn1)[C@@H](O)c1cccc(F)c1] | 467.1 |
| 62 | 6-[5-(difluoromethyl)-1,3,4-oxadiazol-2-yl]-2-[(1R*,2S*)-2-(3-fluorophenyl)-2-hydroxy-1-(pyridin-2-yl)ethyl]-2,3-dihydro-1H-isoindol-1-one (Enantiomer 2) | 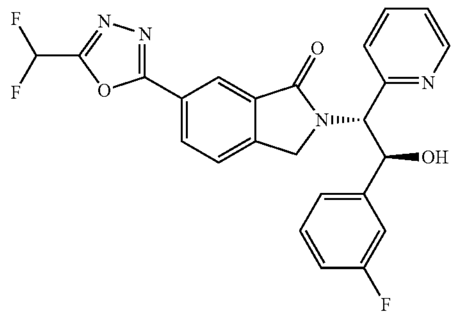 [SMILES: O=C1c2cc(-c3nnc(C(F)F)o3)ccc2CN1[C@H](c1ccccn1)[C@@H](O)c1cccc(F)c1] | 467.1 |
| 63 | 2-[(1R,2S)-1-cyclopropyl-2-(6-fluoropyridin-3-yl)-2-hydroxyethyl]-6-[5-(difluoromethyl)-1,3,4-oxadiazol-2-yl]-2,3-dihydro-1H-isoindol-1-one | 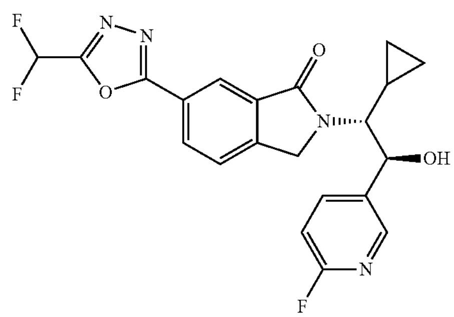 [SMILES: O=C1c2cc(-c3nnc(C(F)F)o3)ccc2CN1[C@H](C1CC1)[C@@H](O)c1ccc(F)nc1] | 429.2 |

TABLE 1-10

| EXAMPLE | IUPAC NAME | Structure | MS |
|---|---|---|---|
| 64 | 6-[5-(difluoromethyl)-1,3,4-oxadiazol-2-yl]-2-[(1R,2S)-2-(3-fluorophenyl)-2-hydroxy-1-(oxan-4-yl)ethyl]-2,3-dihydro-1H-isoindol-1-one | 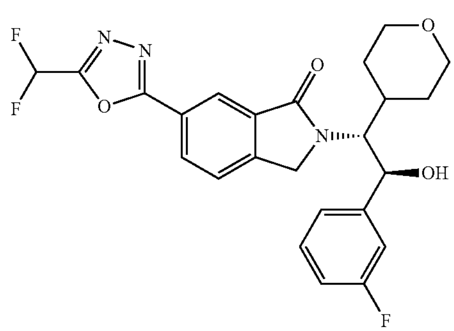 | 472.2 |

TABLE 1-10-continued

| EXAMPLE | IUPAC NAME | Structure | MS |
|---|---|---|---|
| 65 | 2-[(1RS,2RS)-2-(5-chloropyridin-2-yl)-1-cyclopropyl-2-hydroxyethyl]-6-[5-(difluoromethyl)-1,3,4-oxadiazol-2-yl]-2,3-dihydro-1H-isoindol-1-one | 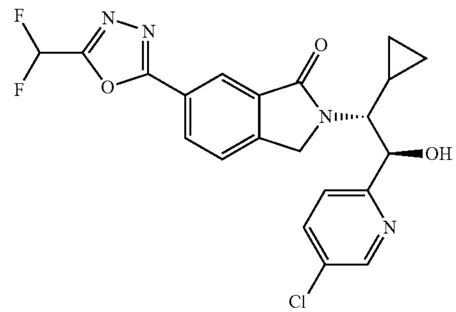 | 447.1 |
| 66 | 6-[5-(difluoromethyl)-1,3,4-oxadiazol-2-yl]-2-[(1R*,2R*)-1-(5-fluoropyridin-2-yl)-2-(6-fluoropyridin-2-yl)-2-hydroxyethyl]-2,3-dihydro-1H-isoindol-1-one (Enantiomer 1) | 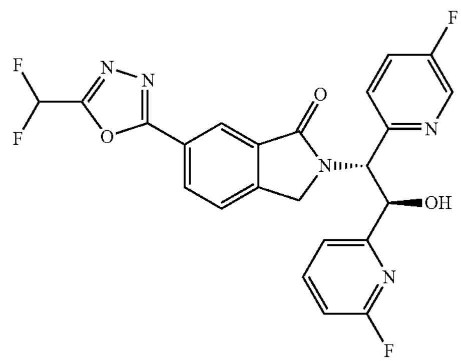 [SMILES: O=C1c2cc(-c3nnc(C(F)F)o3)ccc2CN1[C@H](c1ccc(F)cn1)[C@@H](O)c1cccc(F)n1] | 486.1 |
| 67 | 6-[5-(difluoromethyl)-1,3,4-oxadiazol-2-yl]-2-[(1R*,2R*)-1-(5-fluoropyridin-2-yl)-2-(6-fluoropyridin-2-yl)-2-hydroxyethyl]-2,3-dihydro-1H-isoindol-1-one (Enantiomer 2) | 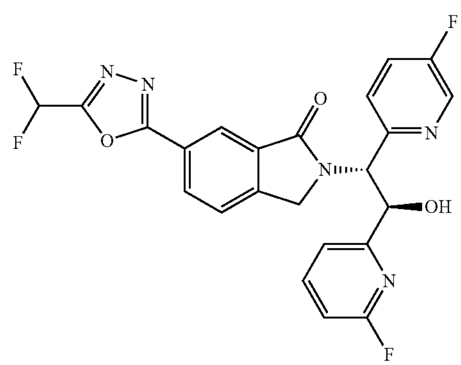 [SMILES: O=C1c2cc(-c3nnc(C(F)F)o3)ccc2CN1[C@H](c1ccc(F)cn1)[C@@H](O)c1cccc(F)n1] | 486.1 |
| 68 | 6-[5-(difluoromethyl)-1,3,4-oxadiazol-2-yl]-2-[(1R*,2S*)-2-(3-fluorophenyl)-2-hydroxy-1-(pyrimidin-2-yl)ethyl]-2,3-dihydro-1H-isoindol-1-one (Enantiomer 1) | 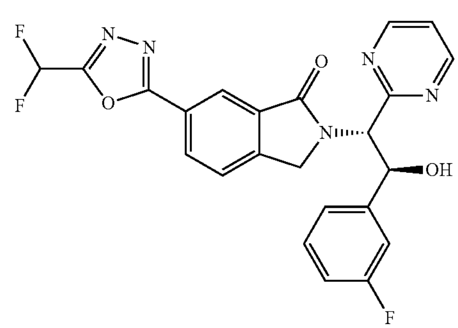 [SMILES: O=C1c2cc(-c3nnc(C(F)F)o3)ccc2CN1[C@H](c1ncccn1)[C@@H](O)c1cccc(F)c1] | 468.1 |

TABLE 1-10-continued

| EXAMPLE | IUPAC NAME | Structure | MS |
|---|---|---|---|
| 69 | 6-[5-(difluoromethyl)-1,3,4-oxadiazol-2-yl]-2-[(1R*,2S*)-2-(3-fluorophenyl)-2-hydroxy-1-(pyrimidin-2-yl)ethyl]-2,3-dihydro-1H-isoindol-1-one (Enantiomer 2) | 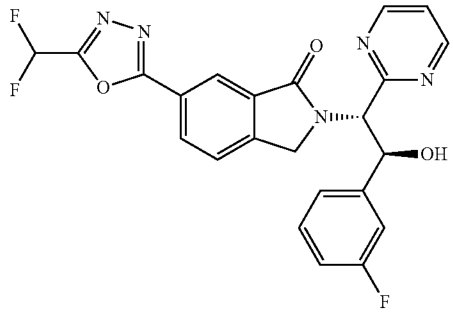 [SMILES: O=C1c2cc(-c3nnc(C(F)F)o3)ccc2CN1[C@H](c1ncccn1)[C@@H](O)c1cccc(F)c1] | 468.2 |
| 70 | 2-[(1R*,2S*)-2-(3-chlorophenyl)-2-hydroxy-1-(oxan-4-yl)ethyl]-6-[5-(difluoromethyl)-1,3,4-oxadiazol-2-yl]-2,3-dihydro-1H-isoindol-1-one (Enantiomer 1) | 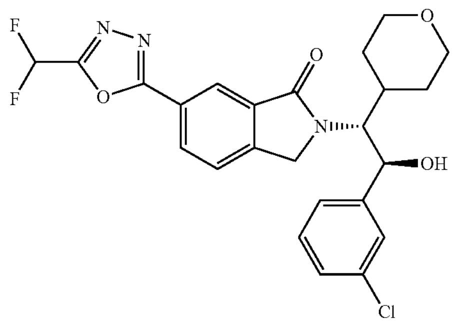 [SMILES: O=C1c2cc(-c3nnc(C(F)F)o3)ccc2CN1[C@H](C1CCOCC1)[C@@H](O)c1cccc(Cl)c1] | 488.1 |

TABLE 1-11

| EXAMPLE | IUPAC NAME | Structure | MS |
|---|---|---|---|
| 71 | 2-[(1R*,2S*)-2-(3-chlorophenyl)-2-hydroxy-1-(oxan-4-yl)ethyl]-6-[5-(difluoromethyl)-1,3,4-oxadiazol-2-yl]-2,3-dihydro-1H-isoindol-1-one (Enantiomer 2) | 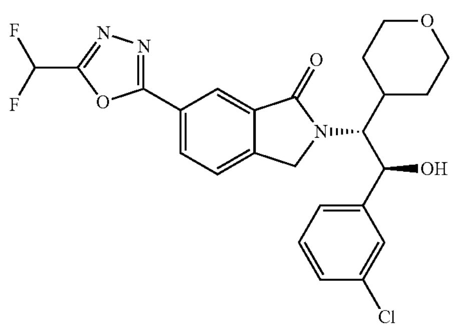 [SMILES: O=C1c2cc(-c3nnc(C(F)F)o3)ccc2CN1[C@H](C1CCOCC1)[C@@H](O)c1cccc(Cl)c1] | 488.1 |
| 72 | 6-[5-(difluoromethyl)-1,3,4-oxadiazol-2-yl]-2-[(1R,2S)-2-(4-fluorophenyl)-2-hydroxy-1-(oxan-4-yl)ethyl]-2,3-dihydro-1H-isoindol-1-one | 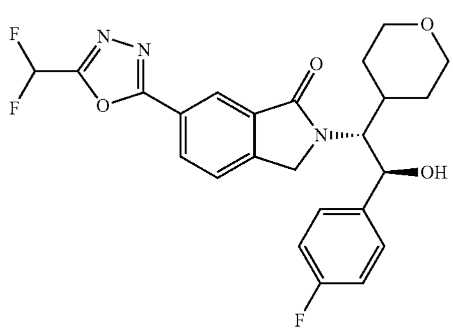 [SMILES: O=C1c2cc(-c3nnc(C(F)F)o3)ccc2CN1[C@H](C1CCOCC1)[C@@H](O)c1ccc(F)cc1] | 472.2 |

TABLE 1-11-continued

| EXAMPLE | IUPAC NAME | Structure | MS |
|---|---|---|---|
| 73 | 2-[(1R*,2R*)-1-cyclopropyl-2-hydroxy-2-(pyrimidin-2-yl)ethyl]-6-[5-(difluoromethyl)-1,3,4-oxadiazol-2-yl]-2,3-dihydro-1H-isoindol-1-one (Enantiomer 1) | 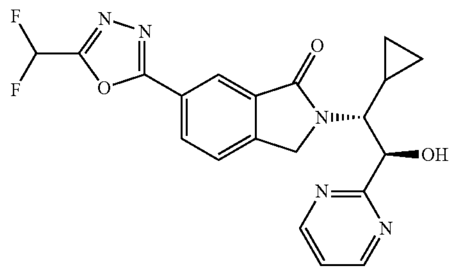 [SMILES: O=C1c2cc(-c3nnc(C(F)F)o3)ccc2CN1[C@H](C1CC1)[C@@H](O)c1ncccn1] | 414.2 |
| 74 | 2-[(1R*,2R*)-1-cyclopropyl-2-hydroxy-2-(pyrimidin-2-yl)ethyl]-6-[5-(difluoromethyl)-1,3,4-oxadiazol-2-yl]-2,3-dihydro-1H-isoindol-1-one (Enantiomer 2) | 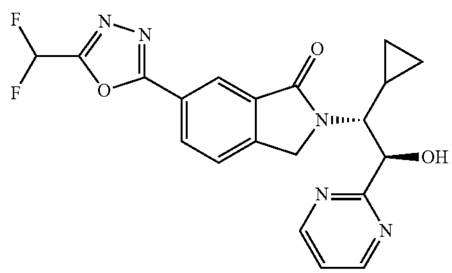 [SMILES: O=C1c2cc(-c3nnc(C(F)F)o3)ccc2CN1[C@H](C1CC1)[C@@H](O)c1ncccn1] | 414.2 |
| 75 | 6-[5-(difluoromethyl)-1,3,4-oxadiazol-2-yl]-2-[(1R*,2R*)-1-(6-fluoropyridin-2-yl)-2-hydroxy-2-(pyridin-2-yl)ethyl]-2,3-dihydro-1H-isoindol-1-one (Enantiomer 1) | 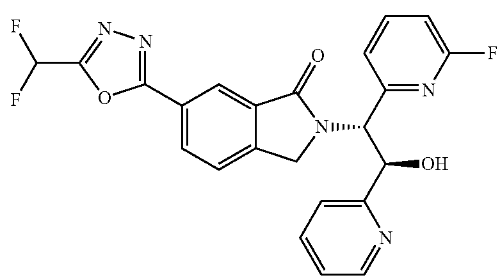 [SMILES: O=C1c2cc(-c3nnc(C(F)F)o3)ccc2CN1[C@H](c1cccc(F)n1)[C@@H](O)c1ccccn1] | 468.2 |
| 76 | 6-[5-(difluoromethyl)-1,3,4-oxadiazol-2-yl]-2-[(1R*,2R*)-1-(6-fluoropyridin-2-yl)-2-hydroxy-2-(pyridin-2-yl)ethyl]-2,3-dihydro-1H-isoindol-1-one (Enantiomer 2) | 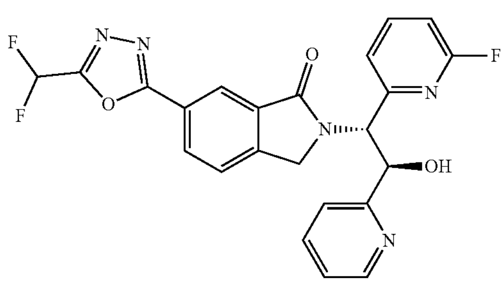 [SMILES: O=C1c2cc(-c3nnc(C(F)F)o3)ccc2CN1[C@H](c1cccc(F)n1)[C@@H](O)c1ccccn1] | 468.2 |
| 77 | 2-{(1R*,2S*)-1-cyclopropyl-2-hydroxy-2-[6-(trifluoromethyl)pyridin-3-yl]ethyl}-6-[5-(difluoromethyl)-1,3,4-oxadiazol-2-yl]-2,3-dihydro-1H-isoindol-1-one (Enantiomer 1) | 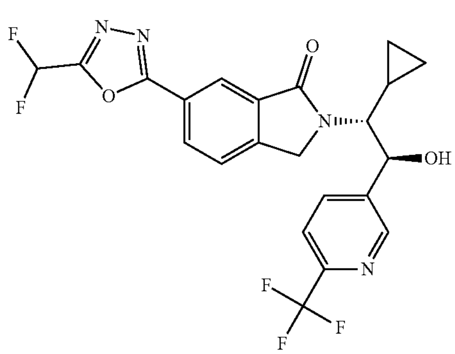 [SMILES: O=C1c2cc(-c3nnc(C(F)F)o3)ccc2CN1[C@H](C1CC1)[C@@H](O)c1ccc(C(F)(F)F)nc1] | 479.1 |

TABLE 1-12

| EXAMPLE | IUPAC NAME | Structure | MS |
|---|---|---|---|
| 78 | 2-{(1R*,2S*)-1-cyclopropyl-2-hydroxy-2-[6-(trifluoromethyl)pyridin-3-yl]ethyl}-6-[5-(difluoromethyl)-1,3,4-oxadiazol-2-yl]-2,3-dihydro-1H-isoindol-1-one (Enantiomer 2) | 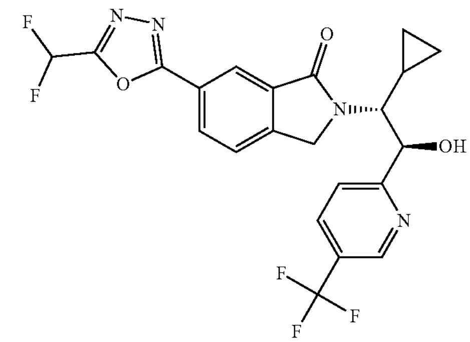 [SMILES: O=C1c2cc(-c3nnc(C(F)F)o3)ccc2CN1[C@H](C1CC1)[C@@H](O)c1ccc(C(F)(F)F)cn1] | 479.1 |
| 79 | 2-[(1R*,2R*)-1-cyclopropyl-2-(6-fluoropyridin-2-yl)-2-hydroxyethyl]-6-[5-(difluoromethyl)-1,3,4-oxadiazol-2-yl]-2,3-dihydro-1H-isoindol-1-one (Enantiomer 1) | 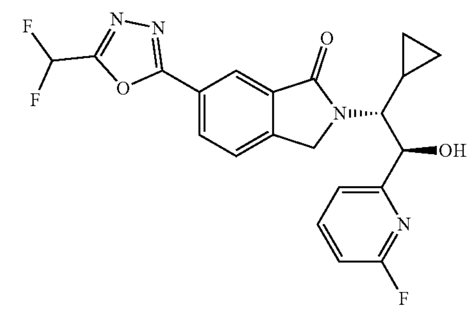 [SMILES: O=C1c2cc(-c3nnc(C(F)F)o3)ccc2CN1[C@H](C1CC1)[C@@H](O)c1cccc(F)n1] | 431.2 |
| 80 | 2-[(1R*,2R*)-1-cyclopropyl-2-(6-fluoropyridin-2-yl)-2-hydroxyethyl]-6-[5-(difluoromethyl)-1,3,4-oxadiazol-2-yl]-2,3-dihydro-1H-isoindol-1-one (Enantiomer 2) | 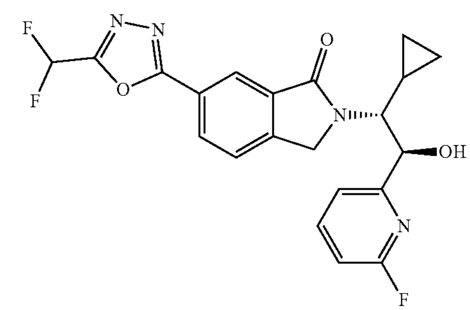 [SMILES: O=C1c2cc(-c3nnc(C(F)F)o3)ccc2CN1[C@H](C1CC1)[C@@H](O)c1cccc(F)n1] | 431.2 |
| 81 | 2-[(1RS,2RS)-1-(4,4-difluorocyclohexyl)-2-hydroxy-2-(pyridin-2-yl)ethyl]-6-[5-(difluoromethyl)-1,3,4-oxadiazol-2-yl]-2,3-dihydro-1H-isoindol-1-one | 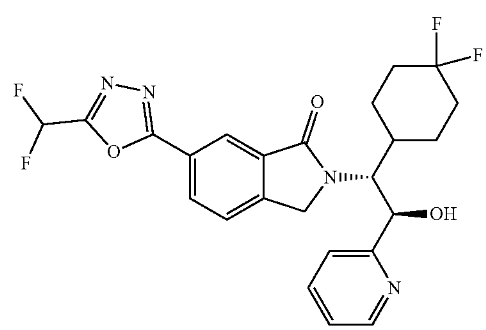 [SMILES: O=C1c2cc(-c3nnc(C(F)F)o3)ccc2CN1[C@H](C1CCC(F)(F)CC1)[C@@H](O)c1ccccn1] | 491.1 |

TABLE 1-12-continued

| EXAMPLE | IUPAC NAME | Structure | MS |
|---|---|---|---|
| 82 | 2-[(1RS,2SR)-1-(4,4-difluoro-cyclohexyl)-2-(6-fluoropyridin-3-yl)-2-hydroxyethyl]-6-[5-(difluoromethyl)-1,3,4-oxadiazol-2-yl]-2,3-dihydro-1H-isoindol-1-one | 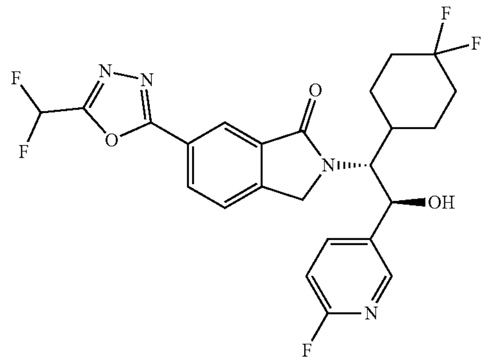 [SMILES: O=C1c2cc(-c3nnc(C(F)F)o3)ccc2CN1[C@H](C1CCC(F)(F)CC1)[C@@H](O)c1ccc(F)nc1] | 507.2 |
| 83 | 2-[(1R*,2S*)-2-(4-chlorophenyl)-2-hydroxy-1-(oxan-4-yl)ethyl]-6-[5-(difluoromethyl)-1,3,4-oxadiazol-2-yl]-2,3-dihydro-1H-isoindol-1-one (Enantiomer 1) | 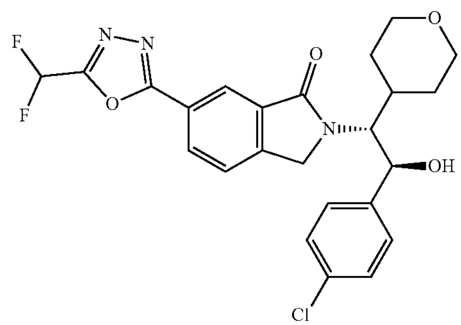 [SMILES: O=C1c2cc(-c3nnc(C(F)F)o3)ccc2CN1[C@H](C1CCOCC1)[C@@H](O)c1ccc(Cl)cc1] | 488.1 |
| 84 | 2-[(1R*,2S*)-2-(4-chlorophenyl)-2-hydroxy-1-(oxan-4-yl)ethyl]-6-[5-(difluoromethyl)-1,3,4-oxadiazol-2-yl]-2,3-dihydro-1H-isoindol-1-one (Enantiomer 2) | 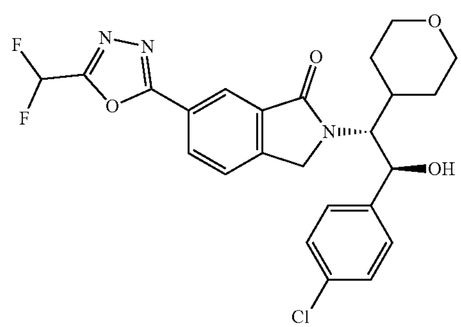 [SMILES: O=C1c2cc(-c3nnc(C(F)F)o3)ccc2CN1[C@H](C1CCOCC1)[C@@H](O)c1ccc(Cl)cc1] | 488.2 |

TABLE 1-13

| EXAMPLE | IUPAC NAME | Structure | MS |
|---|---|---|---|
| 85 | 6-[5-(difluoromethyl)-1,3,4-oxadiazol-2-yl]-2-[(1R*,2S*)-2-(3,4-difluorophenyl)-2-hydroxy-1-(pyrazin-2-yl)ethyl]-2,3-dihydro-1H-isoindol-1-one (Enantiomer 1) | 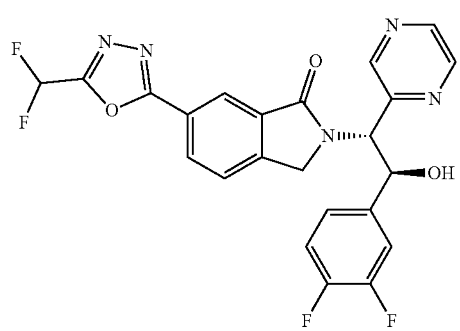 [SMILES: O=C1c2cc(-c3nnc(C(F)F)o3)ccc2CN1[C@H](c1cnccn1)[C@@H](O)c1ccc(F)c(F)c1] | 486.1 |

TABLE 1-13-continued

| EXAMPLE | IUPAC NAME | Structure | MS |
|---|---|---|---|
| 86 | 6-[5-(difluoromethyl)-1,3,4-oxadiazol-2-yl]-2-[(1R*,2S*)-2-(3,4-difluorophenyl)-2-hydroxy-1-(pyrazin-2-yl)ethyl]-2,3-dihydro-1H-isoindol-1-one (Enantiomer 2) | 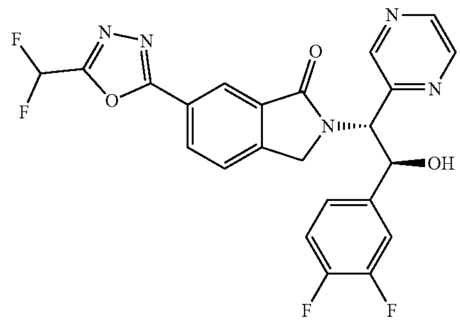 [SMILES: O=C1c2cc(-c3nnc(C(F)F)o3)ccc2CN1[C@H](c1cnccn1)[C@@H](O)c1ccc(F)c(F)c1] | 486.1 |
| 87 | 6-[5-(difluoromethyl)-1,3,4-oxadiazol-2-yl]-2-[(1R*,2S*)-2-(3,4-difluorophenyl)-2-hydroxy-1-(oxan-4-yl)ethyl]-2,3-dihydro-1H-isoindol-1-one (Enantiomer 1) | 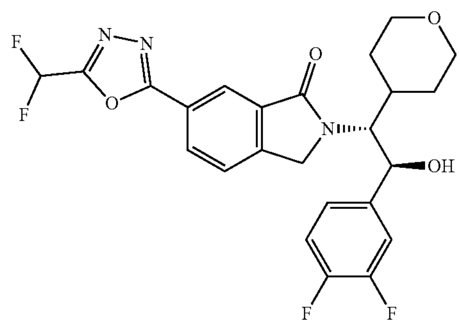 [SMILES: O=C1c2cc(-c3nnc(C(F)F)o3)ccc2CN1[C@H](C1CCOCC1)[C@@H](O)c1ccc(F)c(F)c1] | 490.2 |
| 88 | 6-[5-(difluoromethyl)-1,3,4-oxadiazol-2-yl]-2-[(1R*,2S*)-2-(3,4-difluorophenyl)-2-hydroxy-1-(oxan-4-yl)ethyl]-2,3-dihydro-1H-isoindol-1-one (Enantiomer 2) | 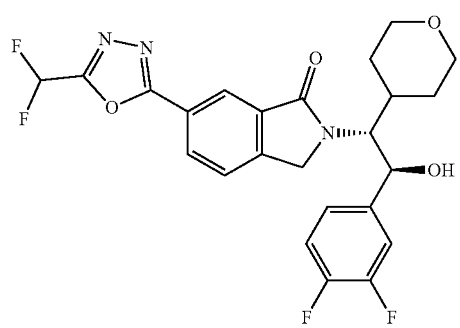 [SMILES: O=C1c2cc(-c3nnc(C(F)F)o3)ccc2CN1[C@H](C1CCOCC1)[C@@H](O)c1ccc(F)c(F)c1] | 490.1 |
| 89 | 6-[5-(difluoromethyl)-1,3,4-oxadiazol-2-yl]-2-[(1R*,2S*)-2-(3-fluorophenyl)-1-(6-fluoropyridin-2-yl)-2-hydroxyethyl]-2,3-dihydro-1H-isoindol-1-one (Enantiomer 1) | 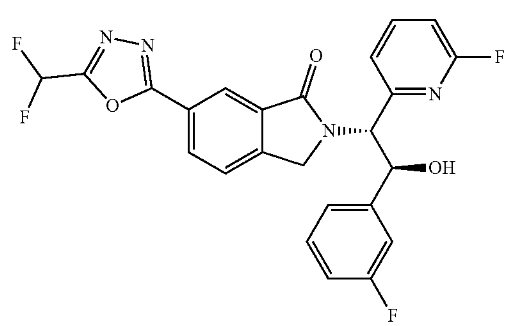 [SMILES: O=C1c2cc(-c3nnc(C(F)F)o3)ccc2CN1[C@H](c1cccc(F)n1)[C@@H](O)c1cccc(F)c1] | 485.1 |
| 90 | 6-[5-(difluoromethyl)-1,3,4-oxadiazol-2-yl]-2-[(1R*,2S*)-2-(3-fluorophenyl)-1-(6-fluoropyridin-2-yl)-2-hydroxyethyl]-2,3-dihydro-1H-isoindol-1-one (Enantiomer 2) | 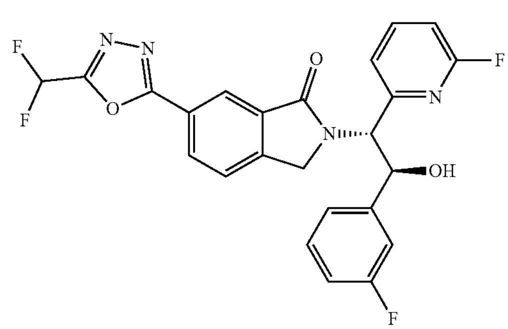 [SMILES: O=C1c2cc(-c3nnc(C(F)F)o3)ccc2CN1[C@H](c1cccc(F)n1)[C@@H](O)c1cccc(F)c1] | 485.0 |

TABLE 1-13-continued

| EXAMPLE | IUPAC NAME | Structure | MS |
|---|---|---|---|
| 91 | 2-[(1R*,2S*)-2-(3-chlorophenyl)-2-hydroxy-1-(pyrazin-2-yl)ethyl]-6-[5-(difluoromethyl)-1,3,4-oxadiazol-2-yl]-2,3-dihydro-1H-isoindol-1-one (Enantiomer 1) | 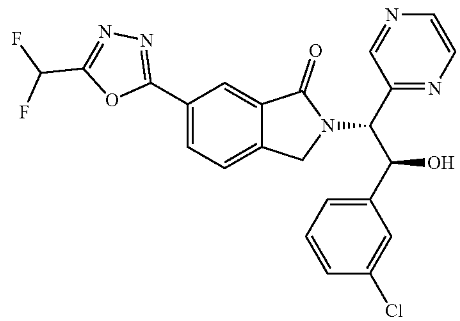 [SMILES: O=C1c2cc(-c3nnc(C(F)F)o3)ccc2CN1[C@H](c1cnccn1)[C@@H](O)c1cccc(Cl)c1] | 484.1 |

TABLE 1-14

| EXAMPLE | IUPAC NAME | Structure | MS |
|---|---|---|---|
| 92 | 2-[(1R*,2S*)-2-(3-chlorophenyl)-2-hydroxy-1-(pyrazin-2-yl)ethyl]-6-[5-(difluoromethyl)-1,3,4-oxadiazol-2-yl]-2,3-dihydro-1H-isoindol-1-one (Enantiomer 2) | 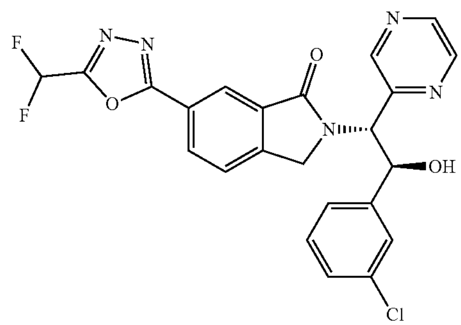 | 484.1 |
| 93 | 2-[(1RS,2SR)-2-(4-chlorophenyl)-2-hydroxy-1-(pyrimidin-2-yl)ethyl]-6-[5-(difluoromethyl)-1,3,4-oxadiazol-2-yl]-2,3-dihydro-1H-isoindol-1-one | 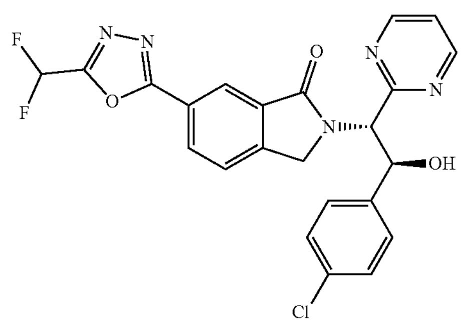 | 484.1 |
| 94 | 6-[5-(difluoromethyl)-1,3,4-oxadiazol-2-yl]-2-[(1R*,2S*)-2-(3,4-difluorophenyl)-2-hydroxy-1-(pyrimidin-2-yl)ethyl]-2,3-dihydro-1H-isoindol-1-one (Enantiomer 1) | 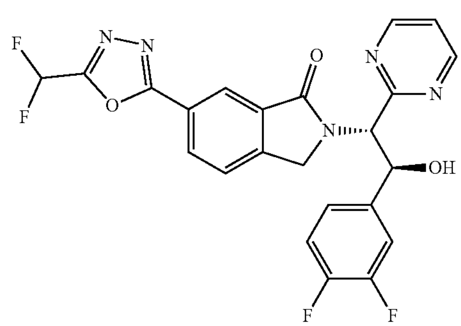 [SMILES: O=C1c2cc(-c3nnc(C(F)F)o3)ccc2CN1[C@H](c1ncccn1)[C@@H](O)c1ccc(F)c(F)c1] | 486.1 |

TABLE 1-14-continued

| EXAMPLE | IUPAC NAME | Structure | MS |
|---|---|---|---|
| 95 | 6-[5-(difluoromethyl)-1,3,4-oxadiazol-2-yl]-2-[(1R*,2S*)-2-(3,4-difluorophenyl)-2-hydroxy-1-(pyrimidin-2-yl)ethyl]-2,3-dihydro-1H-isoindol-1-one (Enantiomer 2) | 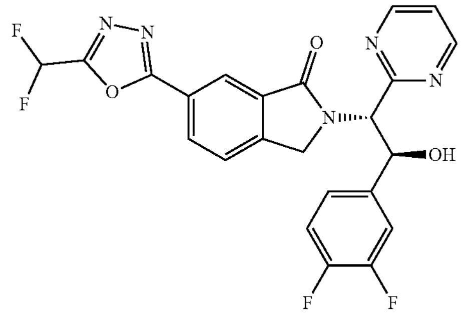 [SMILES: O=C1c2cc(-c3nnc(C(F)F)o3)ccc2CN1[C@H](c1ncccn1)[C@@H](O)c1ccc(F)c(F)c1] | 486.1 |
| 96 | 2-[(1R*,2S*)-2-(4-chlorophenyl)-2-hydroxy-1-(pyrazin-2-yl)ethyl]-6-[5-(difluoromethyl)-1,3,4-oxadiazol-2-yl]-2,3-dihydro-1H-isoindol-1-one (Enantiomer 1) | 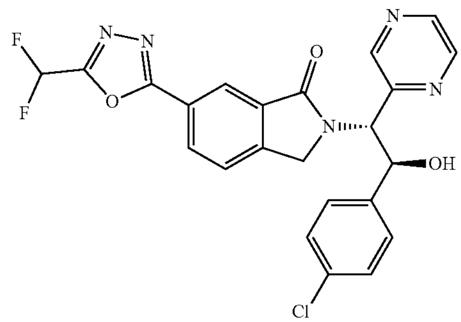 [SMILES: O=C1c2cc(-c3nnc(C(F)F)o3)ccc2CN1[C@H](c1cnccn1)[C@@H](O)c1ccc(Cl)cc1] | 484.1 |
| 97 | 2-[(1R*,2S*)-2-(4-chlorophenyl)-2-hydroxy-1-(pyrazin-2-yl)ethyl]-6-[5-(difluoromethyl)-1,3,4-oxadiazol-2-yl]-2,3-dihydro-1H-isoindol-1-one (Enantiomer 2) | 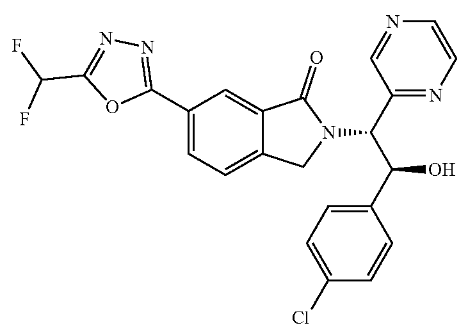 [SMILES: O=C1c2cc(-c3nnc(C(F)F)o3)ccc2CN1[C@H](c1cnccn1)[C@@H](O)c1ccc(Cl)cc1] | 484.1 |
| 98 | 6-[5-(difluoromethyl)-1,3,4-oxadiazol-2-yl]-2-[(1R*,2S*)-2-(4-fluorophenyl)-2-hydroxy-1-(pyrazin-2-yl)ethyl]-2,3-dihydro-1H-isoindol-1-one (Enantiomer 1) | 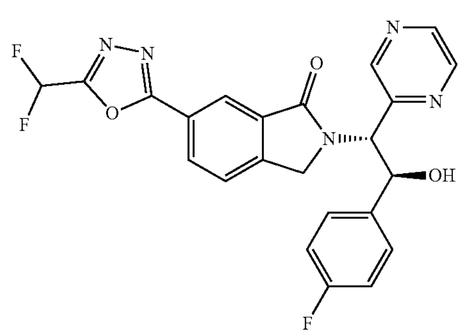 [SMILES: O=C1c2cc(-c3nnc(C(F)F)o3)ccc2CN1[C@H](c1cnccn1)[C@@H](O)c1ccc(F)cc1] | 468.2 |

TABLE 1-15

| EXAMPLE | IUPAC NAME | Structure | MS |
|---|---|---|---|
| 99 | 6-[5-(difluoromethyl)-1,3,4-oxadiazol-2-yl]-2-[(1R*,2S*)-2-(4-fluorophenyl)-2-hydroxy-1-(pyrazin-2-yl)ethyl]-2,3-dihydro-1H-isoindol-1-one (Enantiomer 2) | 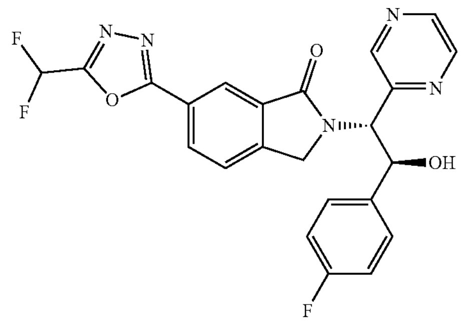 | 468.2 |
| 100 | 6-[5-(difluoromethyl)-1,3,4-oxadiazol-2-yl]-2-[(1R*,2S*)-2-(3-fluorophenyl)-2-hydroxy-1-(pyrazin-2-yl)ethyl]-2,3-dihydro-1H-isoindol-1-one (Enantiomer 1) | 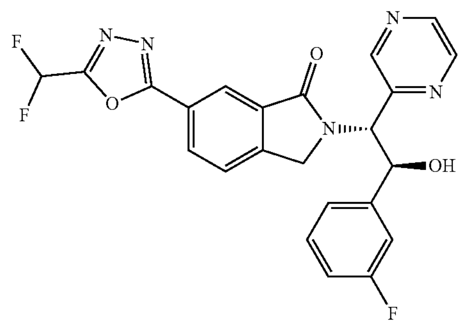 [SMILES: O=C1c2cc(-c3nnc(C(F)F)o3)ccc2CN1[C@H](c1cnccn1)[C@@H](O)c1cccc(F)c1] | 468.2 |
| 101 | 6-[5-(difluoromethyl)-1,3,4-oxadiazol-2-yl]-2-[(1R*,2S*)-2-(3-fluorophenyl)-2-hydroxy-1-(pyrazin-2-yl)ethyl]-2,3-dihydro-1H-isoindol-1-one (Enantiomer 2) | 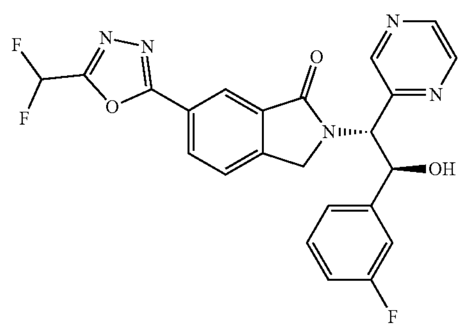 [SMILES: O=C1c2cc(-c3nnc(C(F)F)o3)ccc2CN1[C@H](c1cnccn1)[C@@H](O)c1cccc(F)c1] | 468.2 |
| 102 | 6-[5-(difluoromethyl)-1,3,4-oxadiazol-2-yl]-2-[(1R*,2S*)-2-hydroxy-2-phenyl-1-(pyridin-2-yl)ethyl]-2,3-dihydro-1H-isoindol-1-one (Enantiomer 1) | 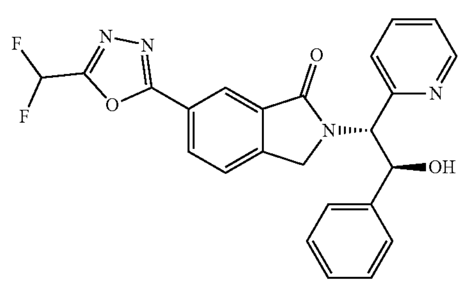 [SMILES: O=C1c2cc(-c3nnc(C(F)F)o3)ccc2CN1[C@H](c1ccccn1)[C@@H](O)c1ccccc1] | 449.2 |
| 103 | 6-[5-(difluoromethyl)-1,3,4-oxadiazol-2-yl]-2-[(1R*,2S*)-2-hydroxy-2-phenyl-1-(pyridin-2-yl)ethyl]-2,3-dihydro-1H-isoindol-1-one (Enantiomer 2) | 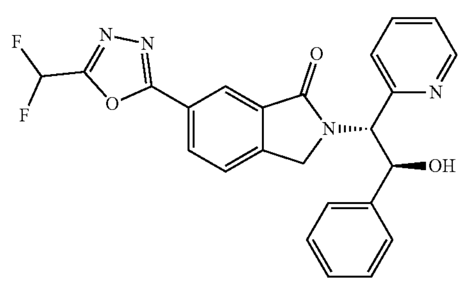 [SMILES: O=C1c2cc(-c3nnc(C(F)F)o3)ccc2CN1[C@H](c1ccccn1)[C@@H](O)c1ccccc1] | 449.2 |

TABLE 1-15-continued

| EXAMPLE | IUPAC NAME | Structure | MS |
|---|---|---|---|
| 104 | 6-[5-(difluoromethyl)-1,3,4-oxadiazol-2-yl]-2-{(1R*,2R*)-2-hydroxy-1-(pyridin-2-yl)-2-[5-(trifluoromethyl)pyridin-2-yl]ethyl}-2,3-dihydro-1H-isoindol-1-one (Enantiomer 1) | 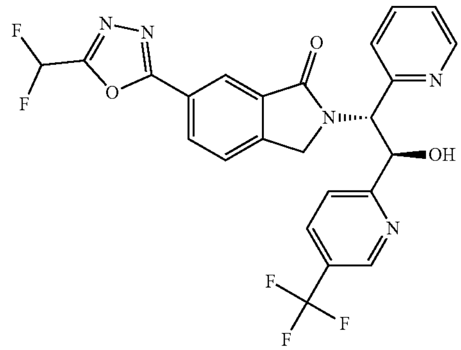 [SMILES: O=C1c2cc(-c3nnc(C(F)F)o3)ccc2CN1[C@H](c1ccccn1)[C@@H](O)c1ccc(C(F)(F)F)cn1] | 518.2 |
| 105 | 6-[5-(difluoromethyl)-1,3,4-oxadiazol-2-yl]-2-{(1R*,2R*)-2-hydroxy-1-(pyridin-2-yl)-2-[5-(trifluoromethyl)pyridin-2-yl]ethyl}-2,3-dihydro-1H-isoindol-1-one (Enantiomer 2) | 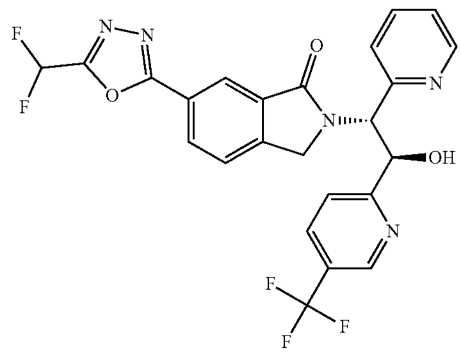 [SMILES: O=C1c2cc(-c3nnc(C(F)F)o3)ccc2CN1[C@H](c1ccccn1)[C@@H](O)c1ccc(C(F)(F)F)cn1] | 518.2 |

TABLE 1-16

| EXAMPLE | IUPAC NAME | Structure | MS |
|---|---|---|---|
| 106 | 2-[(1RS,2SR)-2-(3-chloro-5-fluorophenyl)-2-hydroxy-1-(oxan-4-yl)ethyl]-6-[5-(difluoromethyl)-1,3,4-oxadiazol-2-yl]-2,3-dihydro-1H-isoindol-1-one | 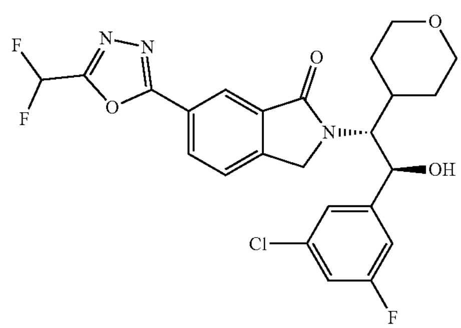 [SMILES: O=C1c2cc(-c3nnc(C(F)F)o3)ccc2CN1[C@H](C1CCOCC1)[C@@H](O)c1cc(F)cc(Cl)c1] | 506.1 |
| 107 | 2-[(1RS,2SR)-2-(3-chloro-4-fluorophenyl)-2-hydroxy-1-(oxan-4-yl)ethyl]-6-[5-(difluoromethyl)-1,3,4-oxadiazol-2-yl]-2,3-dihydro-1H-isoindol-1-one | 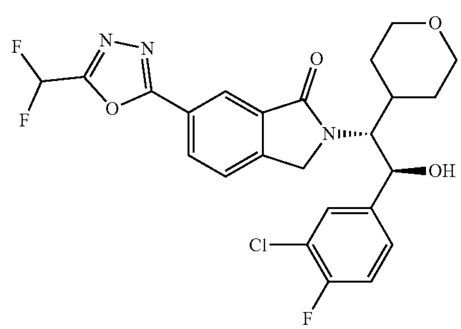 [SMILES: O=C1c2cc(-c3nnc(C(F)F)o3)ccc2CN1[C@H](C1CCOCC1)[C@@H](O)c1ccc(F)c(Cl)c1] | 506.2 |

TABLE 1-16-continued

| EXAMPLE | IUPAC NAME | Structure | MS |
|---|---|---|---|
| 108 | 6-[5-(difluoromethyl)-1,3,4-oxadiazol-2-yl]-2-[(1R*,2S*)-2-(3,4-difluorophenyl)-2-hydroxy-1-(pyridazin-3-yl)ethyl]-2,3-dihydro-1H-isoindol-1-one (Enantiomer 1) | 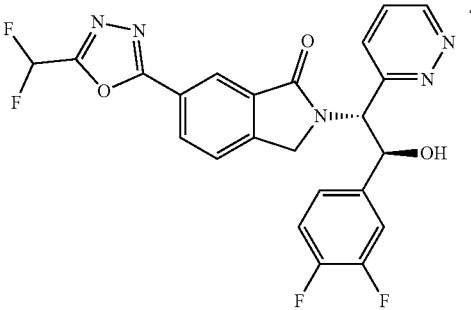 | 486.1 |
| 109 | 6-[5-(difluoromethyl)-1,3,4-oxadiazol-2-yl]-2-[(1R*,2S*)-2-(3,4-difluorophenyl)-2-hydroxy-1-(pyridazin-3-yl)ethyl]-2,3-dihydro-1H-isoindol-1-one (Enantiomer 2) | 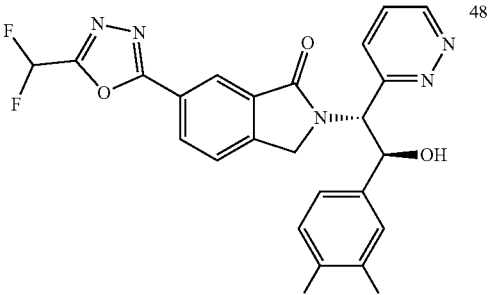 | 486.1 |
| 110 | 2-[(1R*,2S)-2-(4-chlorophenyl)-2-hydroxy-1-(pyridazin-3-yl)ethyl]-6-[5-(difluoromethyl)-1,3,4-oxadiazol-2-yl]-2,3-dihydro-1H-isoindol-1-one (Enantiomer 1) | 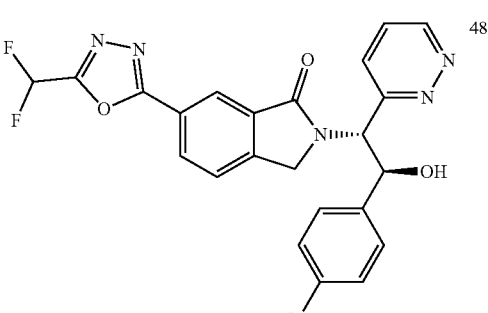 | 484.1 |
| 111 | 2-[(1R*,2S*)-2-(4-chlorophenyl)-2-hydroxy-1-(pyridazin-3-yl)ethyl]-6-[5-(difluoromethyl)-1,3,4-oxadiazol-2-yl]-2,3-dihydro-1H-isoindol-1-one (Enantiomer 2) | 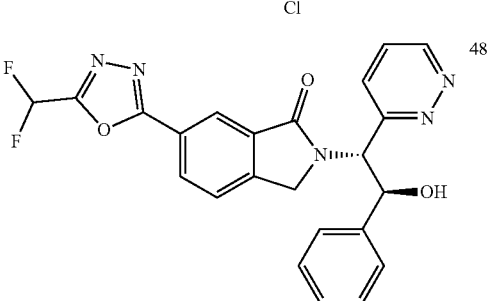 | 484.1 |
| 112 | 2-[(1R*,2R*)-2-(5-chloropyridin-2-yl)-2-hydroxy-1-(pyridin-2-yl)ethyl]-6-[5-(difluoromethyl)-1,3,4-oxadiazol-2-yl]-2,3-dihydro-1H-isoindol-1-one (Enantiomer 1) | 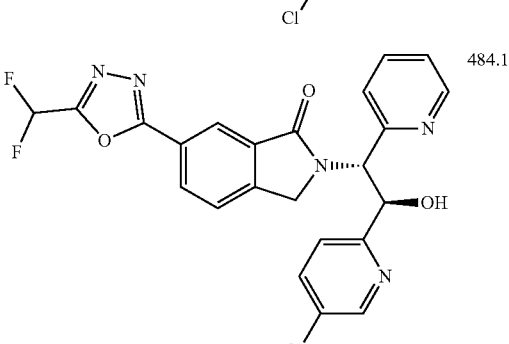 | 484.1 |

TABLE 1-17

| EXAMPLE | IUPAC NAME | Structure | MS |
|---|---|---|---|
| 113 | 2-[(1R*,2R)-2-(5-chloropyridin-2-yl)-2-hydroxy-1-(pyridin-2-yl)ethyl]-6-[5-(difluoromethyl)-1,3,4-oxadiazol-2-yl]-2,3-dihydro-1H-isoindol-1-one (Enantiomer 2) | 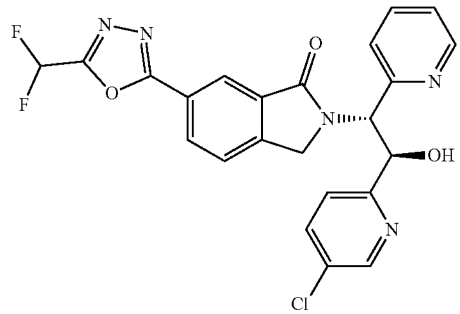 [SMILES: O=C1c2cc(-c3nnc(C(F)F)o3)ccc2CN1[C@H](c1ccccn1)[C@@H](O)c1ccc(Cl)cn1] | 484.1 |
| 114 | 2-[(1R*,2R*)-2-(6-chloropyridin-2-yl)-2-hydroxy-1-(pyridin-2-yl)ethyl]-6-[5-(difluoromethyl)-1,3,4-oxadiazol-2-yl]-2,3-dihydro-1H-isoindol-1-one (Enantiomer 2) | 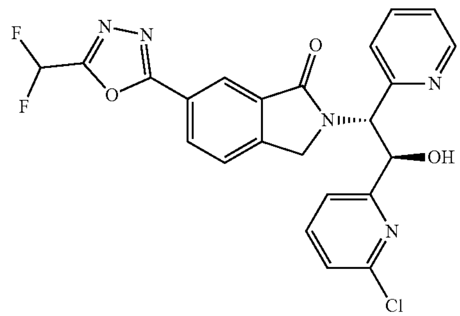 [SMILES: O=C1c2cc(-c3nnc(C(F)F)o3)ccc2CN1[C@H](c1ccccn1)[C@@H](O)c1cccc(Cl)n1] | 484.1 |
| 115 | 2-[(1R*,2R*)-2-(6-chloropyridin-2-yl)-2-hydroxy-1-(pyridin-2-yl)ethyl]-6-[5-(difluoromethyl)-1,3,4-oxadiazol-2-yl]-2,3-dihydro-1H-isoindol-1-one (Enantiomer 1) | 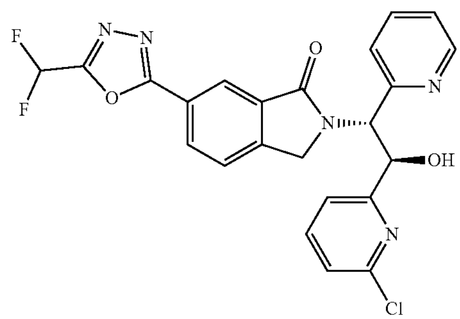 [SMILES: O=C1c2cc(-c3nnc(C(F)F)o3)ccc2CN1[C@H](c1ccccn1)[C@@H](O)c1cccc(Cl)n1] | 484.0 |
| 116 | 6-[5-(difluoromethyl)-1,3,4-oxadiazol-2-yl]-2-{(1RS,2SR)-2-hydroxy-1-(oxan-4-yl)-2-[3-(trifluoromethyl)phenyl]ethyl}-2,3-dihydro-1H-isoindol-1-one | 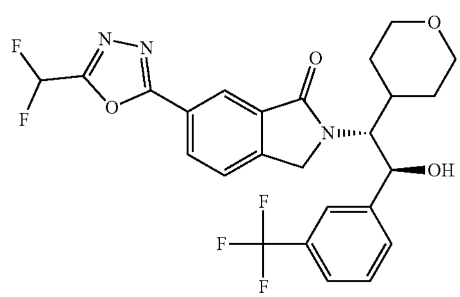 [SMILES: O=C1c2cc(-c3nnc(C(F)F)o3)ccc2CN1[C@H](C1CCOCC1)[C@@H](O)c1cccc(C(F)(F)F)c1] | 522.1 |
| 117 | 2-[(1R*,2R*)-1,2-bis(6-fluoropyridin-2-yl)-2-hydroxyethyl]-6-[5-(difluoromethyl)-1,3,4-oxadiazol-2-yl]-2,3-dihydro-1H-isoindol-1-one (Enantiomer 1) | 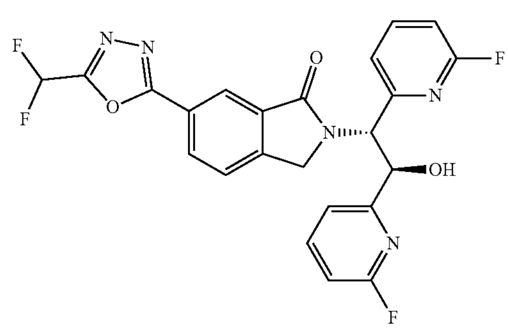 [SMILES: O=C1c2cc(-c3nnc(C(F)F)o3)ccc2CN1[C@H](c1cccc(F)n1)[C@@H](O)c1cccc(F)n1] | 486.1 |

TABLE 1-17-continued

| EXAMPLE | IUPAC NAME | Structure | MS |
|---|---|---|---|
| 118 | 2-[(1R*,2R*)-1,2-bis(6-fluoropyridin-2-yl)-2-hydroxyethyl]-6-[5-(difluoromethyl)-1,3,4-oxadiazol-2-yl]-2,3-dihydro-1H-isoindol-1-one (Enantiomer 2) | 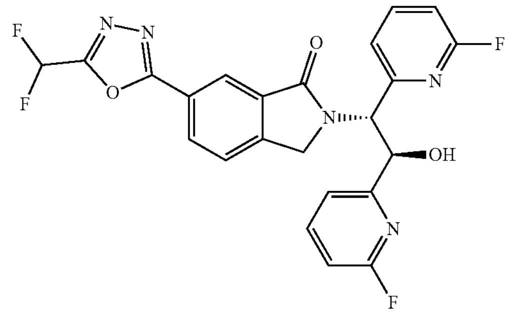 [SMILES: O=C1c2cc(-c3nnc(C(F)F)o3)ccc2CN1[C@H](c1cccc(F)n1)[C@@H](O)c1cccc(F)n1] | 486.1 |
| 119 | 6-[5-(difluoromethyl)-1,3,4-oxadiazol-2-yl]-2-{(1R*,2R*)-2-hydroxy-1-(pyridin-2-yl)-2-[6-(trifluoromethyl)pyridin-2-yl]ethyl}-2,3-dihydro-1H-isoindol-1-one (Enantiomer 1) | 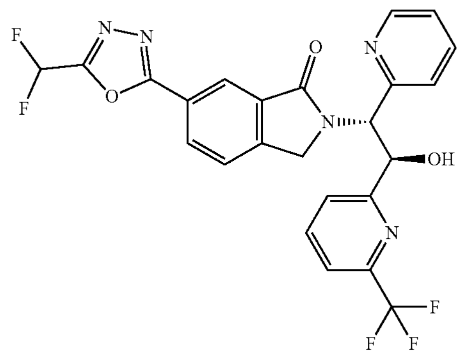 [SMILES: O=C1c2cc(-c3nnc(C(F)F)o3)ccc2CN1[C@H](c1ccccn1)[C@@H](O)c1cccc(C(F)(F)F)n1] | 518.1 |

TABLE 1-18

| EXAMPLE | IUPAC NAME | Structure | MS |
|---|---|---|---|
| 120 | 6-[5-(difluoromethyl)-1,3,4-oxadiazol-2-yl]-2-{(1R*,2R*)-2-hydroxy-1-(pyridin-2-yl)-2-[6-(trifluoromethyl)pyridin-2-yl]ethyl}-2,3-dihydro-1H-isoindol-1-one (Enantiomer 2) | 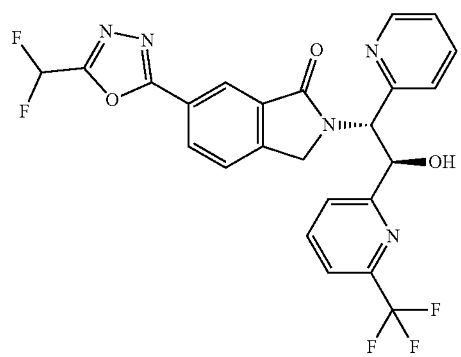 [SMILES: O=C1c2cc(-c3nnc(C(F)F)o3)ccc2CN1[C@H](c1ccccn1)[C@@H](O)c1cccc(C(F)(F)F)n1] | 518.1 |
| 121 | 2-[(1R*,2S)-2-(3-chlorophenyl)-2-hydroxy-1-(pyridazin-3-yl)ethyl]-6-[5-(difluoromethyl)-1,3,4-oxadiazol-2-yl]-2,3-dihydro-1H-isoindol-1-one (Enantiomer 1) | 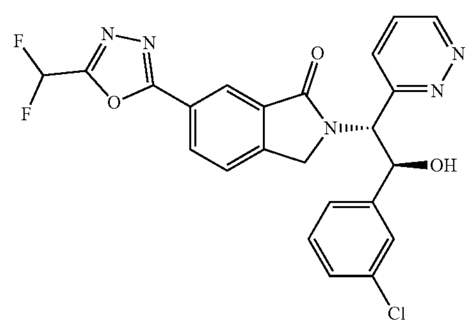 [SMILES: O=C1c2cc(-c3nnc(C(F)F)o3)ccc2CN1[C@H](c1cccnn1)[C@@H](O)c1cccc(Cl)c1] | 484.1 |

TABLE 1-18-continued

| EXAMPLE | IUPAC NAME | Structure | MS |
|---|---|---|---|
| 122 | 2-[(1R*,2S*)-2-(3-chlorophenyl)-2-hydroxy-1-(pyridazin-3-yl)ethyl]-6-[5-(difluoromethyl)-1,3,4-oxadiazol-2-yl]-2,3-dihydro-1H-isoindol-1-one (Enantiomer 2) | 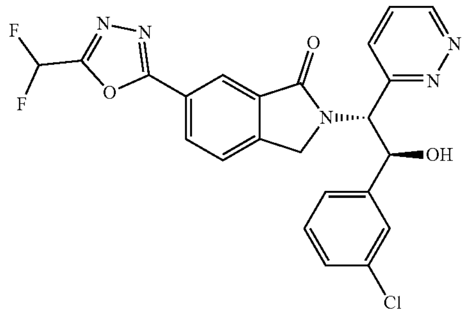 [SMILES: O=C1c2cc(-c3nnc(C(F)F)o3)ccc2CN1[C@H](c1cccnn1)[C@@H](O)c1cccc(Cl)c1] | 484.1 |
| 123 | 2-[(1R*,2R*)-2-(4-chloropyridin-2-yl)-2-hydroxy-1-(pyridin-2-yl)ethyl]-6-[5-(difluoromethyl)-1,3,4-oxadiazol-2-yl]-2,3-dihydro-1H-isoindol-1-one (Enantiomer 1) | 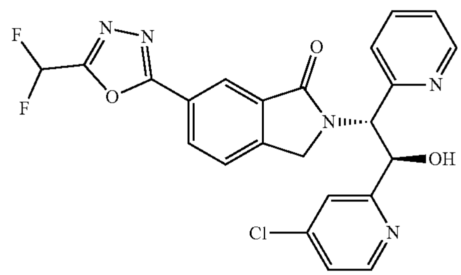 [SMILES: O=C1c2cc(-c3nnc(C(F)F)o3)ccc2CN1[C@H](c1ccccn1)[C@@H](O)c1cc(Cl)ccn1] | 484.1 |
| 124 | 2-[(1R*,2R*)-2-(4-chloropyridin-2-yl)-2-hydroxy-1-(pyridin-2-yl)ethyl]-6-[5-(difluoromethyl)-1,3,4-oxadiazol-2-yl]-2,3-dihydro-1H-isoindol-1-one (Enantiomer 2) | 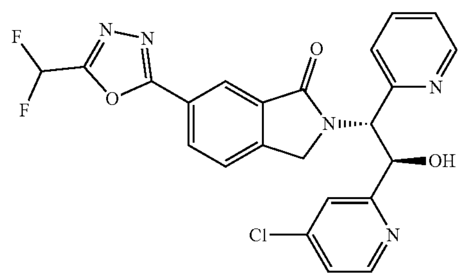 [SMILES: O=C1c2cc(-c3nnc(C(F)F)o3)ccc2CN1[C@H](c1ccccn1)[C@@H](O)c1cc(Cl)ccn1] | 484.1 |
| 125 | 6-[5-(difluoromethyl)-1,3,4-oxadiazol-2-yl]-2-[(1R*,2R)-2-(5-fluoropyridin-2-yl)-1-(6-fluoropyridin-2-yl)-2-hydroxyethyl]-2,3-dihydro-1H-isoindol-1-one (Enantiomer 1) | 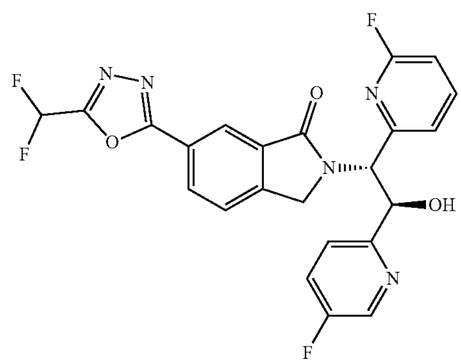 [SMILES: O=C1c2cc(-c3nnc(C(F)F)o3)ccc2CN1[C@H](c1cccc(F)n1)[C@@H](O)c1ccc(F)cn1] | 486.1 |
| 126 | 6-[5-(difluoromethyl)-1,3,4-oxadiazol-2-yl]-2-[(1R*,2R*)-2-(5-fluoropyridin-2-yl)-1-(6-fluoropyridin-2-yl)-2-hydroxyethyl]-2,3-dihydro-1H-isoindol-1-one (Enantiomer 2) | 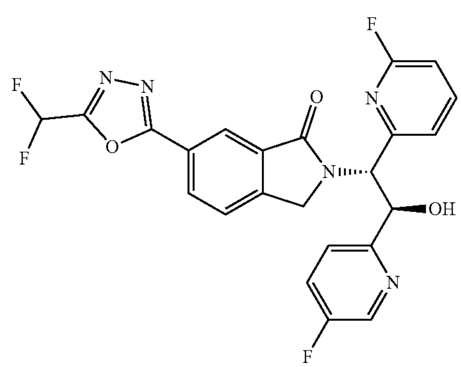 [SMILES: O=C1c2cc(-c3nnc(C(F)F)o3)ccc2CN1[C@H](c1cccc(F)n1)[C@@H](O)c1ccc(F)cn1] | 486.1 |

TABLE 1-19

| EXAMPLE | IUPAC NAME | Structure | MS |
|---|---|---|---|
| 127 | 6-[5-(difluoromethyl)-1,3,4-oxadiazol-2-yl]-2-[(1R*,2S*)-2-hydroxy-2-phenyl-1-(pyrazin-2-yl)ethyl]-2,3-dihydro-1H-isoindol-1-one (Enantiomer 1) | 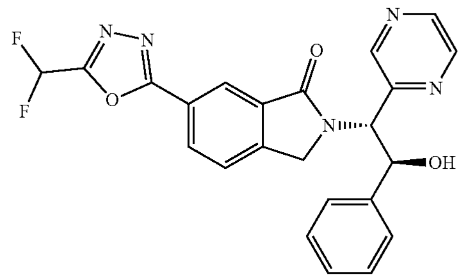 [SMILES: O=C1c2cc(-c3nnc(C(F)F)o3)ccc2CN1[C@H](c1cnccn1)[C@@H](O)c1ccccc1] | 450.1 |
| 128 | 6-[5-(difluoromethyl)-1,3,4-oxadiazol-2-yl]-2-[(1R*,2S*)-2-hydroxy-2-phenyl-1-(pyrazin-2-yl)ethyl]-2,3-dihydro-1H-isoindol-1-one (Enantiomer 2) | 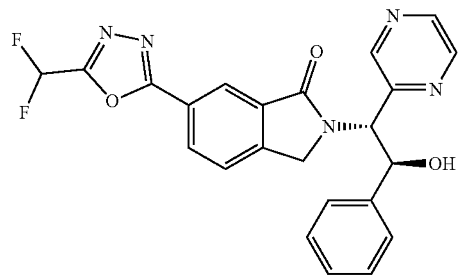 [SMILES: O=C1c2cc(-c3nnc(C(F)F)o3)ccc2CN1[C@H](c1cnccn1)[C@@H](O)c1ccccc1] | 450.1 |
| 129 | 2-[(1R*,2R*)-2-(6-chloropyridin-2-yl)-1-cyclopropyl-2-hydroxyethyl]-6-[5-(difluoromethyl)-1,3,4-oxadiazol-2-yl]-2,3-dihydro-1H-isoindol-1-one (Enantiomer 1) | 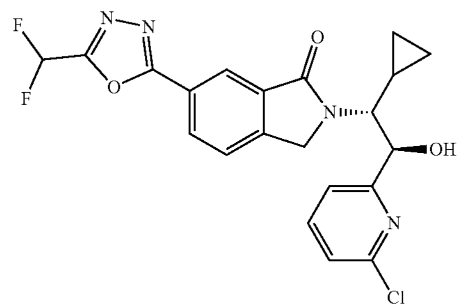 [SMILES: O=C1c2cc(-c3nnc(C(F)F)o3)ccc2CN1[C@H](C1CC1)[C@@H](O)c1cccc(Cl)n1] | 447.1 |
| 130 | 2-[(1R*,2R*)-2-(6-chloropyridin-2-yl)-1-cyclopropyl-2-hydroxyethyl]-6-[5-(difluoromethyl)-1,3,4-oxadiazol-2-yl]-2,3-dihydro-1H-isoindol-1-one (Enantiomer 2) | 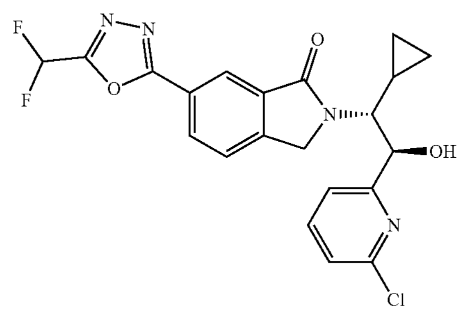 [SMILES: O=C1c2cc(-c3nnc(C(F)F)o3)ccc2CN1[C@H](C1CC1)[C@@H](O)c1cccc(Cl)n1] | 447.1 |
| 131 | 6-[5-(difluoromethyl)-1,3,4-oxadiazol-2-yl]-2-[(1R*,2S*)-1-(4-fluorophenyl)-2-(6-fluoropyridin-3-yl)-2-hydroxyethyl]-2,3-dihydro-1H-isoindol-1-one (Enantiomer 1) | 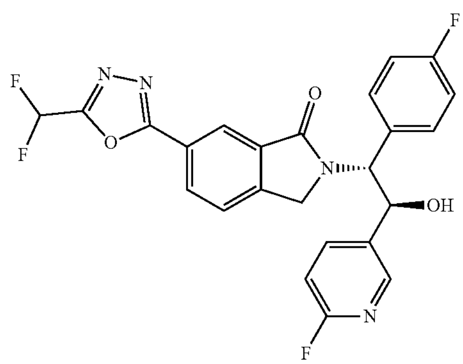 [SMILES: O=C1c2cc(-c3nnc(C(F)F)o3)ccc2CN1[C@H](c1ccc(F)cc1)[C@@H](O)c1ccc(F)nc1] | 485.1 |

TABLE 1-19-continued

| EXAMPLE | IUPAC NAME | Structure | MS |
|---|---|---|---|
| 132 | 6-[5-(difluoromethyl)-1,3,4-oxadiazol-2-yl]-2-[(1R*,2S*)-1-(4-fluorophenyl)-2-(6-fluoropyridin-3-yl)-2-hydroxyethyl]-2,3-dihydro-1H-isoindol-1-one (Enantiomer 2) | 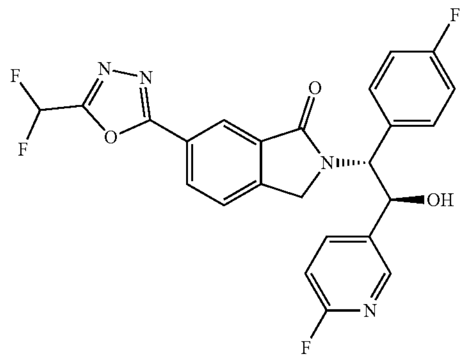 [SMILES: O=C1c2cc(-c3nnc(C(F)F)o3)ccc2CN1[C@H](c1ccc(F)cc1)[C@@H](O)c1ccc(F)nc1] | 485.1 |
| 133 | 2-[(1RS,2SR)-2-(3-chlorophenyl)-2-hydroxy-1-(pyrimidin-2-yl)ethyl]-6-[5-(difluoromethyl)-1,3,4-oxadiazol-2-yl]-2,3-dihydro-1H-isoindol-1-one | 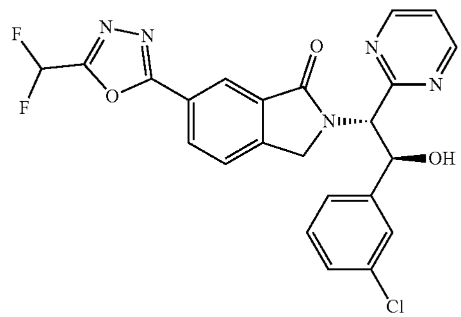 [SMILES: O=C1c2cc(-c3nnc(C(F)F)o3)ccc2CN1[C@H](c1ncccn1)[C@@H](O)c1cccc(Cl)c1] | 484.1 |

TABLE 1-20

| EXAMPLE | IUPAC NAME | Structure | MS |
|---|---|---|---|
| 134 | 6-[5-(difluoromethyl)-1,3,4-oxadiazol-2-yl]-2-[(1RS,2SR)-2-(4-fluorophenyl)-2-hydroxy-1-(pyrimidin-2-yl)ethyl]-2,3-dihydro-1H-isoindol-1-one | 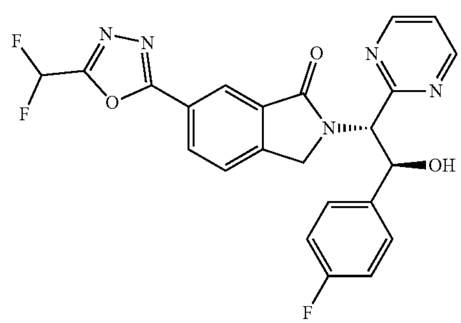 [SMILES: O=C1c2cc(-c3nnc(C(F)F)o3)ccc2CN1[C@H](c1ncccn1)[C@@H](O)c1ccc(F)cc1] | 468.2 |
| 135 | 6-[5-(difluoromethyl)-1,3,4-oxadiazol-2-yl]-2-[(1RS,2SR)-2-hydroxy-1,2-di(pyridin-2-yl)ethyl]-2,3-dihydro-1H-isoindol-1-one | 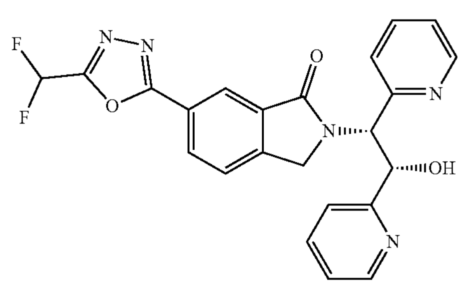 [SMILES: O=C1c2cc(-c3nnc(C(F)F)o3)ccc2CN1[C@H](c1ccccn1)[C@H](O)c1ccccn1] | 450.1 |

TABLE 1-20-continued

| EXAMPLE | IUPAC NAME | Structure | MS |
|---|---|---|---|
| 136 | 6-[5-(difluoromethyl)-1,3,4-oxadiazol-2-yl]-2-[(1RS,2RS)-2-(3-fluorophenyl)-2-hydroxy-1-(pyrimidin-2-yl)ethyl]-2,3-dihydro-1H-isoindol-1-one | 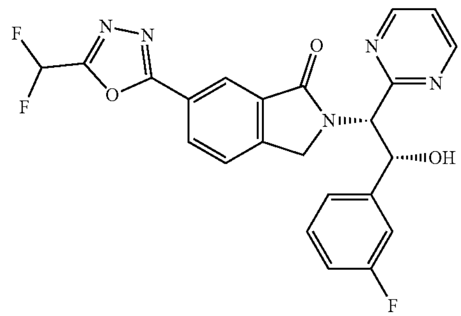 [SMILES: O=C1c2cc(-c3nnc(C(F)F)o3)ccc2CN1[C@H](c1ncccn1)[C@H](O)c1cccc(F)c1] | 468.2 |
| 137 | 2-[(1R,2R)-1-cyclopropyl-2-(4-fluorophenyl)-2-hydroxyethyl]-6-[5-(difluoromethyl)-1,3,4-oxadiazol-2-yl]-2,3-dihydro-1H-isoindol-1-one | 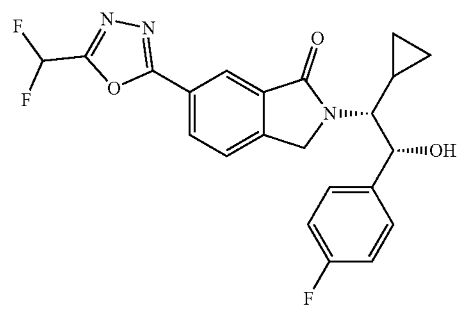 [SMILES: O=C1c2cc(-c3nnc(C(F)F)o3)ccc2CN1[C@H](C1CC1)[C@H](O)c1ccc(F)cc1] | 430.2 |
| 138 | 6-[5-(difluoromethyl)-1,3,4-oxadiazol-2-yl]-2-[(1SR,2SR)-1-(4-fluorophenyl)-2-hydroxy-2-phenylethyl]-2,3-dihydro-1H-isoindol-1-one | 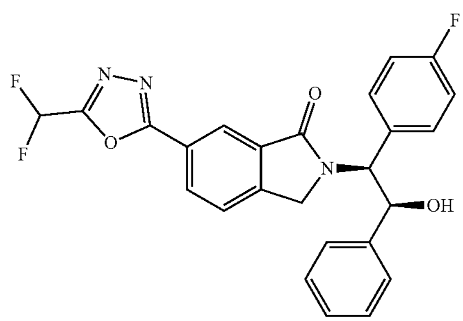 [SMILES: O=C1c2cc(-c3nnc(C(F)F)o3)ccc2CN1[C@@H](c1ccc(F)cc1)[C@@H](O)c1ccccc1] | 446.1 |
| 139 | 6-[5-(difluoromethyl)-1,3,4-oxadiazol-2-yl]-2-[(1RS,2RS)-2-(2-fluorophenyl)-2-hydroxy-1-phenylethyl]-2,3-dihydro-1H-isoindol-1-one | 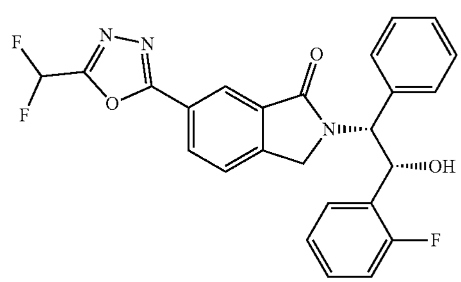 [SMILES: O=C1c2cc(-c3nnc(C(F)F)o3)ccc2CN1[C@H](c1ccccc1)[C@H](O)c1ccccc1F] | 466.1 |
| 140 | 2-[(1RS,2RS)-2-cyclopropyl-1-(4-fluorophenyl)-2-hydroxyethyl]-6-[5-(difluoromethyl)-1,3,4-oxadiazol-2-yl]-2,3-dihydro-1H-isoindol-1-one | 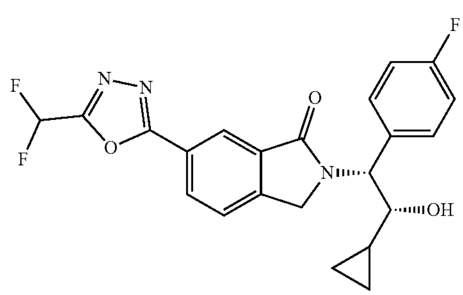 [SMILES: O=C1c2cc(-c3nnc(C(F)F)o3)ccc2CN1[C@H](c1ccc(F)cc1)[C@H](O)C1CC1] | 430.2 |

TABLE 1-21

| EXAMPLE | IUPAC NAME | Structure | MS |
|---|---|---|---|
| 141 | 6-[5-(difluoromethyl)-1,3,4-oxadiazol-2-yl]-2-[(1RS,2RS)-2-(4-fluorophenyl)-2-hydroxy-1-(pyridin-2-yl)ethyl]-2,3-dihydro-1H-isoindol-1-one | 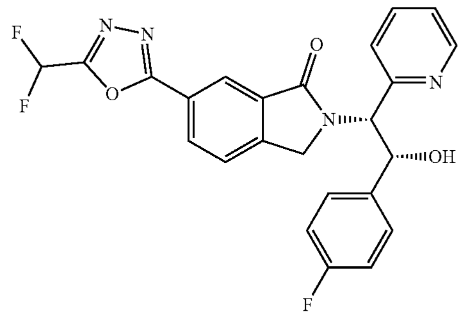 [SMILES: O=C1c2cc(-c3nnc(C(F)F)o3)ccc2CN1[C@H](c1ccccn1)[C@H](O)c1ccc(F)cc1] | 467.1 |
| 142 | 6-[5-(difluoromethyl)-1,3,4-oxadiazol-2-yl]-2-{(1RS,2RS)-1-(4-fluorophenyl)-2-hydroxy-2-[6-(trifluoromethyl)pyridin-3-yl]ethyl}-2,3-dihydro-1H-isoindol-1-one | 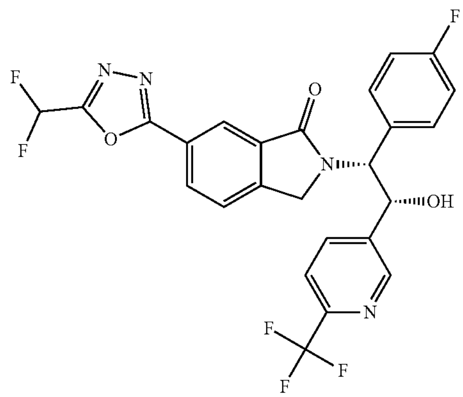 [SMILES: O=C1c2cc(-c3nnc(C(F)F)o3)ccc2CN1[C@H](c1ccc(F)cc1)[C@H](O)c1ccc(C(F)(F)F)nc1] | 533.1 |
| 143 | 6-[5-(difluoromethyl)-1,3,4-oxadiazol-2-yl]-2-[(1RS,2RS)-2-hydroxy-2-phenyl-1-(pyridin-2-yl)ethyl]-2,3-dihydro-1H-isoindol-1-one | 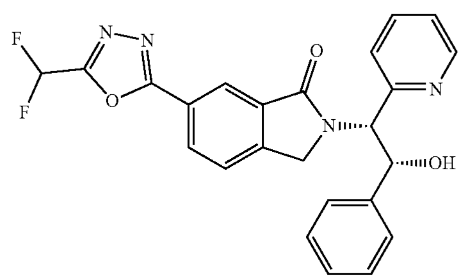 [SMILES: O=C1c2cc(-c3nnc(C(F)F)o3)ccc2CN1[C@H](c1ccccn1)[C@H](O)c1ccccc1] | 449.2 |
| 144 | 6-[5-(difluoromethyl)-1,3,4-oxadiazol-2-yl]-2-[(1RS,2SR)-1-(5-fluoropyridin-2-yl)-2-hydroxy-2-(pyridin-2-yl)ethyl]-2,3-dihydro-1H-isoindol-1-one | 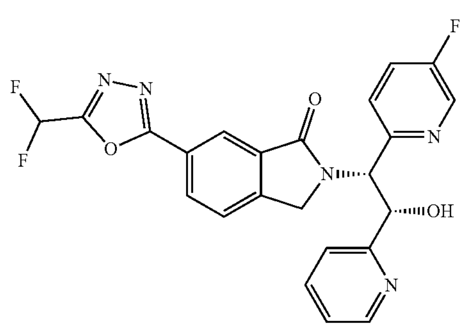 [SMILES: O=C1c2cc(-c3nnc(C(F)F)o3)ccc2CN1[C@H](c1ccc(F)cn1)[C@H](O)c1ccccn1] | 468.2 |

TABLE 1-21-continued

| EXAMPLE | IUPAC NAME | Structure | MS |
|---|---|---|---|
| 145 | 6-[5-(difluoromethyl)-1,3,4-oxadiazol-2-yl]-2-[(1SR,2SR)-2-(3-fluorophenyl)-2-hydroxy-1-(pyridin-2-yl)ethyl]-2,3-dihydro-1H-isoindol-1-one | 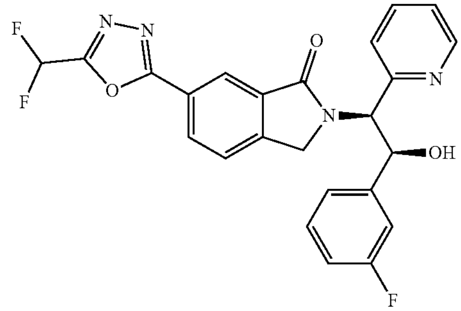 [SMILES: O=C1c2cc(-c3nnc(C(F)F)o3)ccc2CN1[C@@H](c1ccccn1)[C@@H](O)c1cccc(F)c1] | 467.1 |
| 146 | 6-[5-(difluoromethyl)-1,3,4-oxadiazol-2-yl]-2-[(1SR,2SR)-1-(2,4-difluorophenyl)-2-(4-fluorophenyl)-2-hydroxyethyl]-2,3-dihydro-1H-isoindol-1-one | 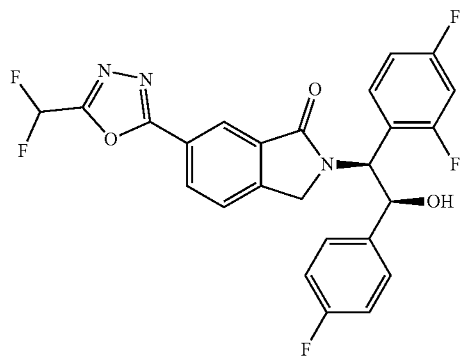 [SMILES: O=C1c2cc(-c3nnc(C(F)F)o3)ccc2CN1[C@@H](c1ccc(F)cc1F)[C@@H](O)c1ccc(F)cc1] | 500.1 |
| 147 | 6-[5-(difluoromethyl)-1,3,4-oxadiazol-2-yl]-2-[(1RS,2RS)-2-(3-fluorophenyl)-1-(4-fluorophenyl)-2-hydroxyethyl]-2,3-dihydro-1H-isoindol-1-one | 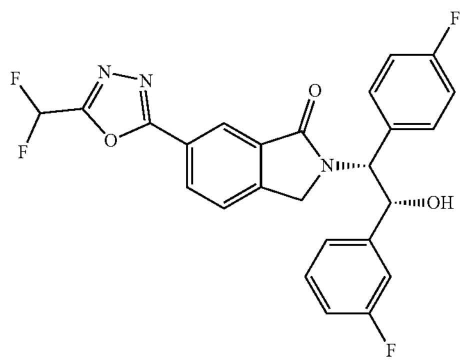 [SMILES: O=C1c2cc(-c3nnc(C(F)F)o3)ccc2CN1[C@H](c1ccc(F)cc1)[C@H](O)c1cccc(F)c1] | 484.1 |

TABLE 1-22

| EXAMPLE | IUPAC NAME | Structure | MS |
|---|---|---|---|
| 148 | 6-[5-(difluoromethyl)-1,3,4-oxadiazol-2-yl]-2-[(1R,2R)-2-(4-fluorophenyl)-2-hydroxy-1-(oxan-4-yl)ethyl]-2,3-dihydro-1H-isoindol-1-one | 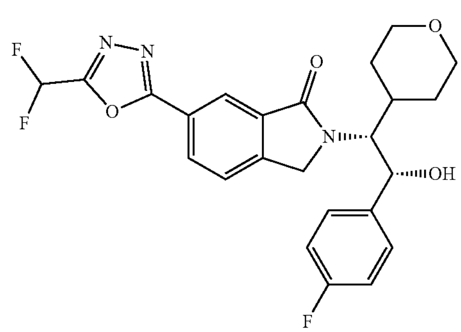 [SMILES: O=C1c2cc(-c3nnc(C(F)F)o3)ccc2CN1[C@H](C1CCOCC1)[C@H](O)c1ccc(F)cc1] | 472.2 |

TABLE 1-22-continued

| EXAMPLE | IUPAC NAME | Structure | MS |
|---|---|---|---|
| 149 | 6-[5-(difluoromethyl)-1,3,4-oxadiazol-2-yl]-2-[(1R,2R)-2-(3-fluorophenyl)-2-hydroxy-1-(oxan-4-yl)ethyl]-2,3-dihydro-1H-isoindol-1-one | 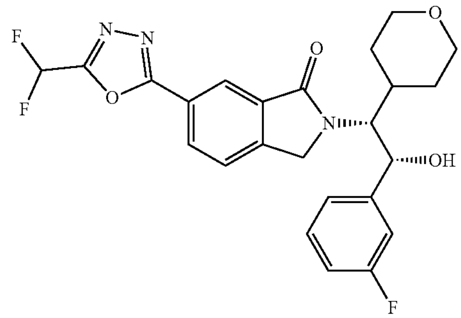 [SMILES: O=C1c2cc(-c3nnc(C(F)F)o3)ccc2CN1[C@H](C1CCOCC1)[C@H](O)c1cccc(F)c1] | 472.2 |
| 150 | 2-[(1R,2S)-1-cyclopropyl-2-(5-fluoropyridin-2-yl)-2-hydroxyethyl]-6-[5-(difluoromethyl)-1,3,4-oxadiazol-2-yl]-2,3-dihydro-1H-isoindol-1-one | 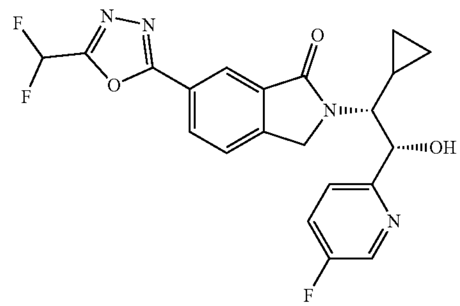 [SMILES: O=C1c2cc(-c3nnc(C(F)F)o3)ccc2CN1[C@H](C1CC1)[C@H](O)c1ccc(F)cn1] | 431.2 |

Experimental Example 1 HDAC6 Enzyme Inhibitory Assay

HDAC6 enzyme prepared by transducing full length HDAC6 gene into Sf-9 insect cells and purifying by GST affinity column were purchased from SignalChem. Using this enzyme, HDAC6 enzyme inhibitory activity of the compound of the present invention were evaluated. Enzymes were used after preserved at −70° C. HDAC6 enzyme inhibitory activity of the compound of the present invention was measured using HDAC-Glo™ I/II Assay kit (Promega) according to the following experimental method. The test compound diluted with assay buffer (24 mM Tris-HCl (pH 7.5), 1 mM $MgCl_2$, 0.35 mM KCl, 135 mM NaCl, 0.6 mM Glutathione, 0.01% Tween-20) was added to a 384-well plate by each 2 μL. Then, HDAC6 enzyme solution diluted with assay buffer was added thereto by each 4 μL, and the plate was incubated at room temperature for 60 min. After incubated, HDAC substrate-Developer solution prepared according to Promega protocol attached to the assay kit was added to the 384-well plate by each 2 μL, and the enzyme reaction was started. After reacting at room temperature for 20 min, luminescence level was measured using plate reader Envision (PerkinElmer). The inhibitory activity of each compound of Example was calculated as a relative activity value when luminescence level in wells without enzyme is considered as 100% inhibition. The results are shown in Table 2-1 and Table 2-2.

TABLE 2-1

| Ex. No. | HDAC6 inhibitory rate (%) (10 μM) |
|---|---|
| 1 | 101 |
| 2 | 100 |
| 3 | 101 |
| 4 | 100 |
| 5 | 99 |
| 6 | 100 |
| 7 | 102 |
| 8 | 99 |
| 9 | 100 |
| 10 | 100 |
| 11 | 99 |
| 12 | 100 |
| 13 | 99 |
| 14 | 100 |
| 15 | 99 |
| 16 | 99 |
| 17 | 100 |
| 18 | 99 |
| 19 | 99 |
| 20 | 100 |
| 21 | 100 |
| 22 | 99 |
| 23 | 100 |
| 24 | 99 |
| 25 | 100 |
| 26 | 99 |
| 27 | 101 |
| 28 | 99 |
| 29 | 99 |
| 30 | 99 |
| 31 | 97 |
| 32 | 99 |
| 33 | 100 |
| 34 | 100 |
| 35 | 100 |
| 36 | 101 |
| 37 | 100 |
| 38 | 100 |
| 39 | 101 |
| 40 | 100 |
| 41 | 100 |
| 42 | 100 |
| 43 | 100 |

TABLE 2-1-continued

| Ex. No. | HDAC6 inhibitory rate (%) (10 μM) |
|---|---|
| 44 | 100 |
| 45 | 100 |
| 46 | 100 |
| 47 | 99 |
| 48 | 100 |
| 49 | 99 |
| 50 | 99 |
| 51 | 99 |
| 52 | 100 |
| 53 | 100 |
| 54 | 100 |
| 55 | 98 |
| 56 | 100 |
| 57 | 100 |
| 58 | 100 |
| 59 | 100 |
| 60 | 99 |
| 61 | 100 |
| 62 | 100 |
| 63 | 100 |
| 64 | 100 |
| 65 | 98 |
| 66 | 100 |
| 67 | 99 |
| 68 | 101 |
| 69 | 100 |
| 70 | 101 |
| 71 | 101 |
| 72 | 100 |
| 73 | 100 |
| 74 | 96 |
| 75 | 99 |
| 76 | 100 |
| 77 | 100 |
| 78 | 99 |
| 79 | 99 |
| 80 | 100 |
| 81 | 100 |
| 82 | 100 |
| 83 | 101 |
| 84 | 100 |
| 85 | 100 |
| 86 | 100 |
| 87 | 100 |
| 88 | 99 |
| 89 | 100 |
| 90 | 100 |

TABLE 2-2

| Ex. No. | HDAC6 inhibitory rate (%) (10 μM) |
|---|---|
| 91 | 100 |
| 92 | 100 |
| 93 | 100 |
| 94 | 100 |
| 95 | 99 |
| 96 | 100 |
| 97 | 99 |
| 98 | 100 |
| 99 | 100 |
| 100 | 100 |
| 101 | 100 |
| 102 | 100 |
| 103 | 100 |
| 104 | 100 |
| 105 | 99 |
| 106 | 100 |
| 107 | 101 |
| 108 | 100 |
| 109 | 100 |
| 110 | 100 |
| 111 | 99 |

TABLE 2-2-continued

| Ex. No. | HDAC6 inhibitory rate (%) (10 μM) |
|---|---|
| 112 | 99 |
| 113 | 100 |
| 114 | 99 |
| 115 | 100 |
| 116 | 101 |
| 117 | 101 |
| 118 | 102 |
| 119 | 101 |
| 120 | 101 |
| 121 | 101 |
| 122 | 100 |
| 123 | 101 |
| 124 | 100 |
| 125 | 101 |
| 126 | 101 |
| 127 | 99 |
| 128 | 99 |
| 129 | 100 |
| 130 | 98 |
| 131 | 99 |
| 132 | 99 |
| 133 | 100 |
| 134 | 101 |
| 135 | 99 |
| 136 | 99 |
| 137 | 100 |
| 138 | 99 |
| 139 | 100 |
| 140 | 98 |
| 141 | 99 |
| 142 | 100 |
| 143 | 100 |
| 144 | 100 |
| 145 | 99 |
| 146 | 95 |
| 147 | 99 |
| 148 | 101 |
| 149 | 100 |
| 150 | 99 |

As is clear from Table 2-1 and Table 2-2, the compound of the present invention has an excellent HDAC6 inhibitory activity.

Experimental Example 2 Increase in Acetylated Tubulin in Brain

Figure 2:
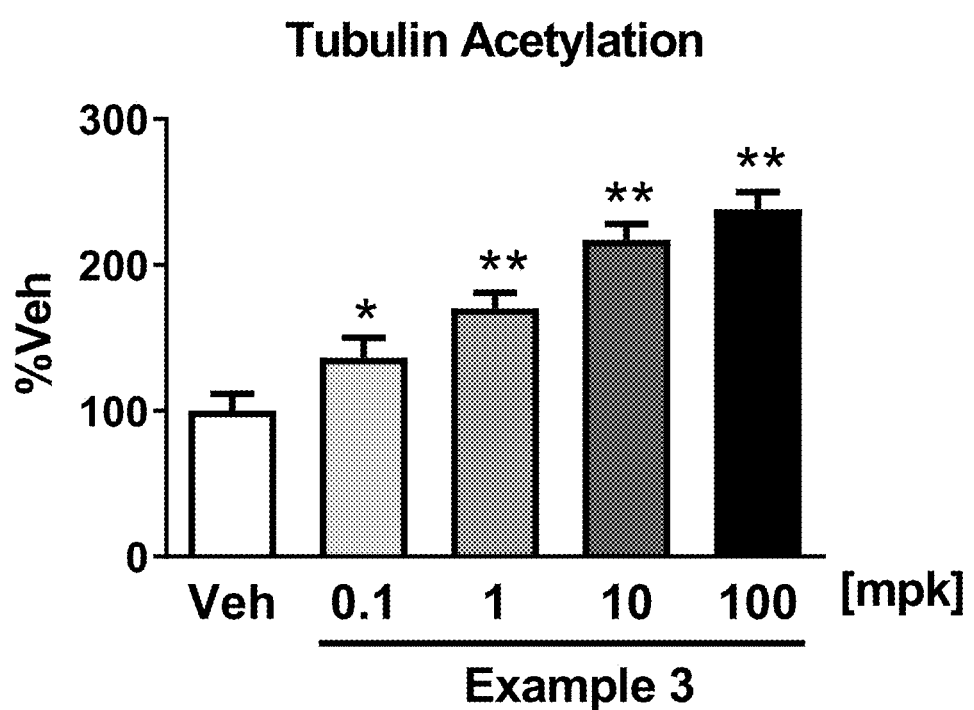
FIG. 2 is a graph showing increase in acetylated tubulin in mouse brain by the compound of Example 3. The vertical axis is relative tubulin acetylation level, and the horizontal axis is the dose (mg/kg).
Figure 3:
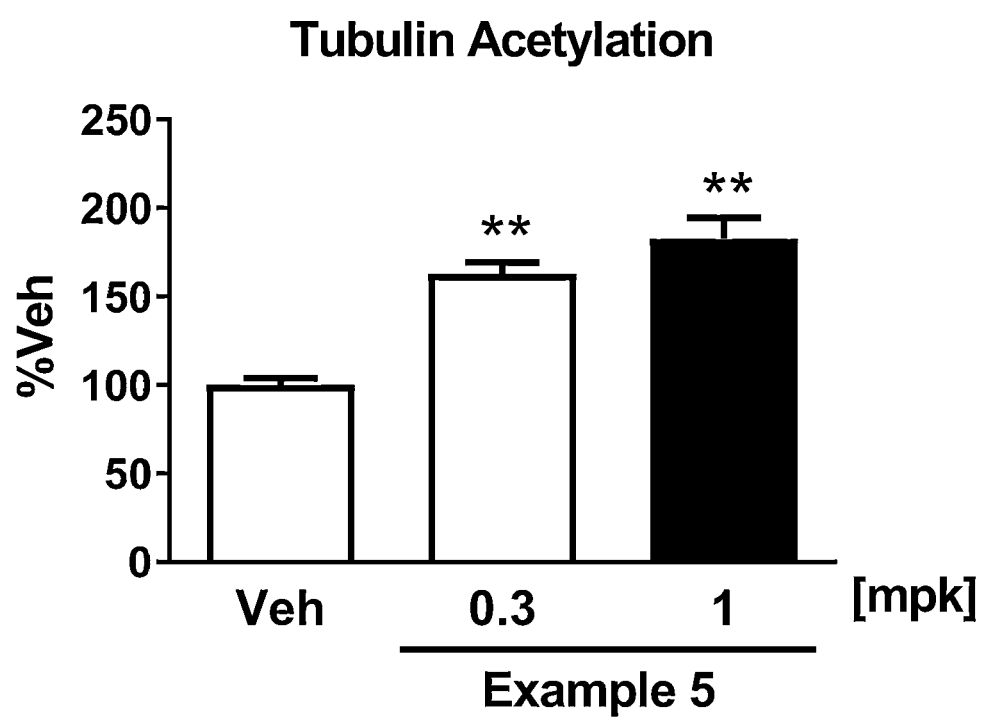
FIG. 3 is a graph showing increase in acetylated tubulin in mouse brain by the compound of Example 5. The vertical axis is relative tubulin acetylation level, and the horizontal axis is the dose (mg/kg).

A drug was suspended in 0.5% methyl cellulose to prepare a suspension for administration, having a concentration shown in Table 3. The suspension was orally administered into 8 to 10-week old male C57BL/6J mouse, and after the passage of the time shown in Table 3, the brain was taken out, and hippocampus was obtained. The hippocampus was homogenized under RIPA extract (FUJIFILM Wako Pure Chemical Corporation) to which protease inhibitor (Thermo Fisher Scientific) and phosphatase inhibitor (Thermo Fisher Scientific) were added, and centrifuged in 15,000 g for 15 min to prepare a protein extract. The acetylated tubulin and total tubulin in the extract were detected by the following ELISA method. Tubulin antibody (Sigma) was immobilized on 96-well plate (Microlite2+, Thermo Fisher Scientific), and the plate was stored at 4° C. Next day, the plate was washed four times with PBS-T, and blocking buffer (1% BSA/PBS-T) was added thereto, and the reaction was carried out at 37° C. for 2 hr. The plate was washed four times with PBS-T, and the above-mentioned protein extract was added thereto to capture the tubulin on the antibody. The plate was stored at 37° C. for 2 hr, and washed four times with PBS-T. Anti-acetylated tubulin antibody or total tubulin antibody (Cell Signaling Technology), each diluted with blocking buffer, was added thereto, and the reaction was carried out at 37° C. for 1 hr. Then, the plate was washed four times with PBS-T, and the reaction was carried out using anti-mouse HPR (Cell Signaling Technology) at 37° C. for 30 min. The plate was washed, HRP substrate was added thereto, and the luminescence was measured using a plate reader. The acetylated tubulin and total tubulin were quantified from logistics curve based on dilution series using the mouse hippocampus tissue extract, and the amount of the acetylated tubulin relative to the total tubulin was calculated, and evaluated as an relative tubulin acetylation level. The test was performed using SAS system 8. After F test for vehicle group and drug group, the significant difference between the two groups was analyzed by Student t-test or Welch test (indicated as *$p<0.05$, $p<0.01$, n.s.: not significant). The graph was indicated by the mean±standard error. The results are shown in FIGS. 1 to 3**. In the mouse into which the compound of Example 1, 3 or 5 was administered, increase in significant tubulin acetylation level was observed.

TABLE 3

| Ex. No. | concentration (mg/mL) | dose (mg/kg) | time (h) after administration of test compound | C57BL/6J old | C573L/6J number |
|---|---|---|---|---|---|
| 1 | 0.01, 0.1, 1, 10 | 0.1, 1, 10, 100 | 4 | 9 | 6 |
| 3 | 0.01, 0.1, 1, 10 | 0.1, 1, 10, 100 | 4 | 8 | 6 |
| 5 | 0.03, 0.1 | 0.3, 1 | 4 | 10 | 6 |

Figure 4:
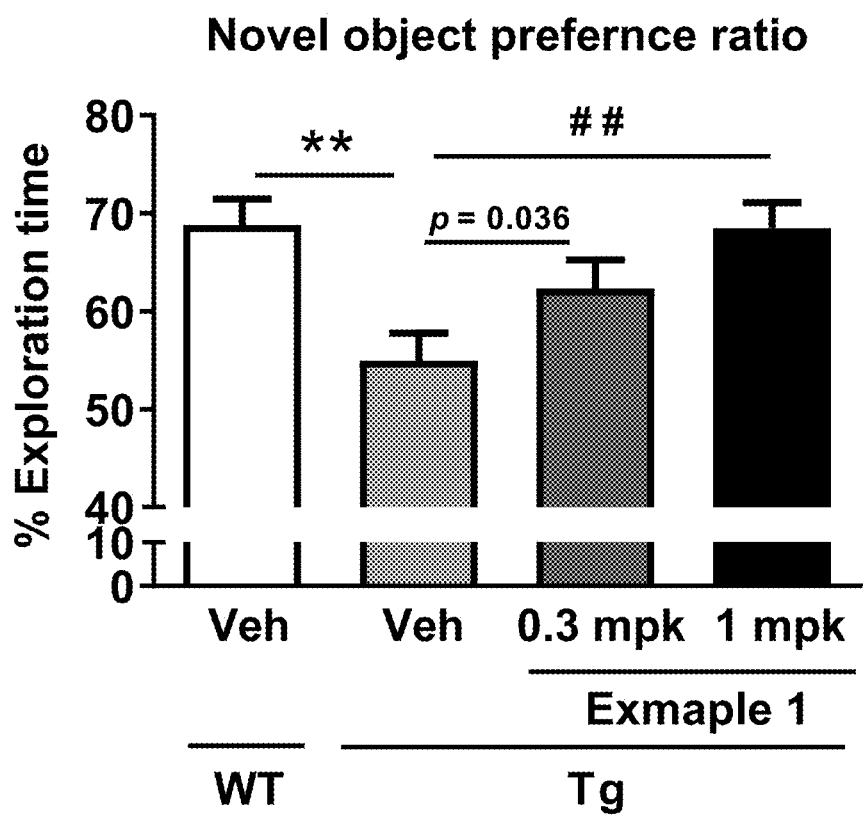
FIG. 4 is a graph showing cognitive improvement action in mouse by the compound of Example 1. The vertical axis is relative exploration time of the novelty discrimination (%), and the horizontal axis is the dose (mg/kg).
Figure 5:
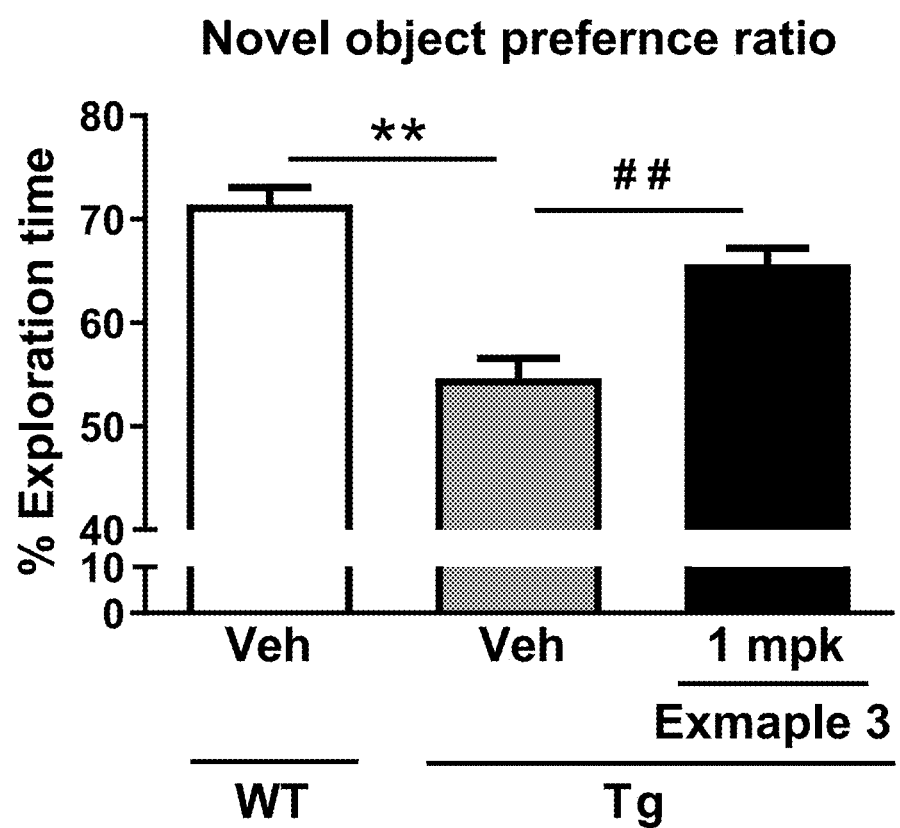
FIG. 5 is a graph showing cognitive improvement action in mouse by the compound of Example 3. The vertical axis is the novelty discrimination relative exploration time of (%), and the horizontal axis is the dose (mg/kg).

Experimental Example 3 Cognitive Improvement Action in Neurodegenerative Disease Model Mouse A drug was suspended in 0.5% methyl cellulose to prepare a suspension for administration. The suspension was repeatedly administered into six month-old male P301S mutant human tau (4R1N) Tg mouse once a day for three months, and novel object recognition test was performed by the following method. The test is comprised of memory acquisition trial of object on the first day, and memory retention trial of familiar object and novel object on the second day. Drug was administered into the mouse 1 hr before the trials on both days. For acquisition trial, The mouse was put in a test box (30 cm×30 cm×25 cm) in which two identical objects were placed, and contact frequency and contact duration with the objects for 5 min were measured under 50 lux. Herein, the contact means a behavior getting a sniff of an object (Sniffing). Next day, one of the objects was replaced with new object, and contact frequency and contact duration with each object for 5 min were measured. Novelty discrimination index (NDI) as an index of cognitive function was calculated by novel object contact frequency/(novel object contact duration+familiar object contact duration) %. The test was performed using SAS system 8. After F test for vehicle administration wild-type group and vehicle administration Tg group, the significant difference between the two groups was analyzed by Student t-test or Welch test (indicated as $p<0.01$). In addition, Bartlett test for homogeneity of variance was performed for vehicle administration or drug administration Tg group, and the significant difference was analyzed by one-tailed Williams test (indicated as ##$p<0.005$). Each group consisted of 14 or 15 mice. The graph was indicated by the mean±standard error. The results are shown in FIGS. 4 and 5**.

Experimental Example 4 Toxicity Test in Rat

A Two-week toxicity test in rats is conducted using the following test system.
Test System:
  Rat, Sprague-Dawley [Crl:CD(SD)]
Administration Method/Period:
  Oral administration, which is the scheduled route for clinical application, is selected as the administration route, and the administration period is 2 weeks. The administration frequency is once a day (7 days/week), which is generally used in repeated dose studies. For oral administration to rodents, the administration method is general oral gavage. The dose is 5 mL/kg, and it is administered by oral gavage using a flexible gastric tube (between 08:00 and 15:00). The vehicle is similarly administered to the vehicle control group. The dose of each animal is calculated based on the most recent body weight.
Vehicle and Preparation Method:
  0.5 w/v % methylcellulose solution and the required amount of methylcellulose (METOLOSE SM-100) are weighed and gradually added to an appropriate amount of warm water for injection with stirring to disperse the methylcellulose. This is cooled to dissolve the methylcellulose, and water for injection is further added thereto to give a 0.5% solution.

A hematology protocol is described below as an example of toxicity assessment.
Materials:
  At the time of planned autopsy, all animals in the test group that had been fasted overnight from the previous day (about 16 to 21 hours) are subjected to laparotomy under isoflurane inhalation anesthesia, and the blood (about 1 mL) is collected from the abdominal aorta into a blood sampling bottle containing EDTA-2K. The obtained blood is tested for the items and by the methods listed below.
Used Equipment:
  Automatic blood cell counter (ADVIA2120i, Siemens Healthcare Diagnostics)
Test Items (Measurement Method):
  Red blood cell count (2-angle laser flow cytometry method)
  Hematocrit value (calculated from red blood cell count and MCV)
  Hemoglobin concentration (modified cyanmethemoglobin method)
  Average red blood cell hemoglobin amount (calculated from MCH, red blood cell count and hemoglobin concentration)
  Average red blood cell hemoglobin concentration (calculated from MCHC, red blood cell count, MCV and hemoglobin concentration)
  Average red blood cell volume (MCV, 2-angle laser flow cytometry method)
  Red blood cell volume distribution width (RDW, 2-angle laser flow cytometry method)
  Reticulocyte count (absolute count, laser flow cytometry by RNA staining)
  Platelet count (2-angle laser flow cytometry method)
  White blood cell count (2-angle laser flow cytometry method)
  White blood cell classification (absolute count, flow cytometry by peroxidase staining+2-angle laser flow cytometry)
  Erythrocyte morphology flag (MICRO: microcytic red blood cells, MACRO: macrocytic red blood cells, HYPO: hypochromic red blood cells, HYPER: hyperchromic red blood cells, ANISO: red blood cell size difference, HCVAR: hemoglobin concentration difference, RBCF: crushed red blood cells)

Experimental Example 5 Bacterial Reversion Assay

Materials and Methods

Test Strains:
*Salmonella typhimurium* TA100 or TA98
Metabolic Activation System:
S9 mix for Ames test prepared from livers of 7-week-old male Sprague-Dawley rats treated with phenobarbital and 5,6-benzoflavone
Doses:
78.1, 156.3, 312.5, 625, 1250, 2500 or 5000 μg/plate
Test Method:
After the bacterial cells are cultured at 37° C. for 8 hours, the optical density (at 660 nm) of cell suspension is measured by spectrophotometer to determine if bacteria grows well. The cell numbers calculated from the optical density are confirmed to be within the acceptable range (cell number: $\geq 1\times 10^9$/mL). Cells are exposed to test article using the pre-incubation method (37° C., 20 minutes) in the presence or absence of S9 mix. After mixing with top agar, cells are overlaid on plates. The plates are incubated at 37° C. for 48 hours. The top agar, solvent, and the test article solution are inspected for bacterial contamination.
Criteria for Mutagenicity:
The test article is determined to be positive if the test article induced a dose-dependent increase in the number of the revertant colonies to a level equal to or greater than 2 times of the mean negative control value in any test strain either in the presence or absence of S9 mix.

Experimental Example 6 In Vitro Micronucleus Assay

Materials and Methods

Test System:
Human lymphoblastoid cells derived TK6 cells
Culture Condition:
The cells are cultured in a 6-well plastic plate at 37° C. and 5% $CO_2$ with RPMI1640 supplemented with 10 vol % heat-inactivated horse serum, 2 mmol/L sodium pyruvate, 100 unit/mL penicillin and 100 μg/mL streptomycin.
Metabolic Activation System:
Rat liver S9 mix prepared from the livers of 7-week-old male Sprague-Dawley rats treated with phenobarbital and 5,6-benzoflavone.
Treatment Conditions:
(1) 3-hour treatment with S9 mix, followed by 21-hour culture, (2) 24-hour continuous treatment without S9 mix
Doses:
450.0 μg/mL to 12.6 μg/mL
Duplicate cultures are prepared for each concentration.
Cytotoxicity:
Cell numbers are counted, and the relative population doubling (RPD) as a cytotoxic evaluation index is calculated using the following formula:

$$\text{Population doubling } (PD) = \frac{\text{Log}_{10}([\text{cell number at the end of culture}]/[\text{cell number at the start of treatment}^*])}{\text{Log}_{10} 2} \quad *: 1\times 10^5 \text{ cells/mL}$$

$$RPD\, (\%) = \frac{PD \text{ for the test article group}}{PD \text{ for the concurrent negative control group}} \times 100$$

Micronucleus Observation:
For each treatment condition, the highest concentration for micronucleus analysis is selected based on precipitation of test articles and cytotoxicity, and two lower consecutive concentrations are examined. The number of micronucleated cells among 4,000 mononuclear cells with cytoplasm is counted using a microscope.
Statistical Analysis:
Fisher's exact test is performed at upper-tailed significance levels of 5% and 1% in order to compare the incidence of micronucleated cells in the test article groups or the positive control group with that of the negative control group for each treatment condition. If Fisher's exact test shows statistically significance in the test article groups, the exact Cochran-Armitage trend test is performed.
Judgment Criteria:
The test article is judged to be positive if the incidence of micronucleated cells between any test article groups satisfied both criteria (1) and (2) shown below.
(1) A significant difference in the incidence of micronucleated cells between the negative control group is detected in the statistical analysis and dose-dependent increase is also detected in the statistical analysis.
(2) The incidence of micronucleated cells is more than the historical control range (mean+2SD). Otherwise, the test article is considered to be negative.

Formulation Example 1 (Production of Capsule)

| | |
|---|---|
| 1) compound of Example 1 | 30 mg |
| 2) fine powder cellulose | 10 mg |
| 3) lactose | 19 mg |
| 4) magnesium stearate | 1 mg |
| Total | 60 mg |

1), 2), 3) and 4) are mixed and filled in a gelatin.

| | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

INDUSTRIAL APPLICABILITY

The compound of the present invention has a HDAC inhibitory activity, and may be useful for the treatment of

The invention claimed is:

1. A compound represented by the formula (I):

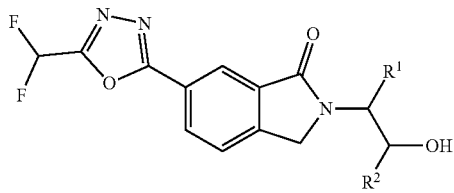

(I)

wherein
$R^1$ is
(1) a $C_{3-10}$ cycloalkyl group optionally substituted by 1 to 3 halogen atoms,
(2) a $C_{6-14}$ aryl group optionally substituted by 1 to 3 substituents selected from (i) a halogen atom, (ii) a cyano group, and (iii) a $C_{1-6}$ alkyl group optionally substituted by 1 to 3 halogen atoms,
(3) a 5- or 6-membered monocyclic aromatic heterocyclic group optionally substituted by 1 to 3 substituents selected from (i) a halogen atom, (ii) a $C_{1-6}$ alkyl group optionally substituted by 1 to 3 halogen atoms, and (iii) a $C_{1-6}$ alkoxy group, or
(4) a 3- to 8-membered monocyclic non-aromatic heterocyclic group, and
$R^2$ is
(1) a $C_{3-10}$ cycloalkyl group optionally substituted by 1 to 3 halogen atoms,
(2) a $C_{6-14}$ aryl group optionally substituted by 1 to 3 substituents selected from (i) a halogen atom, and (ii) a $C_{1-6}$ alkyl group optionally substituted by 1 to 3 halogen atoms,
(3) a 5- or 6-membered monocyclic aromatic heterocyclic group optionally substituted by 1 to 3 substituents selected from (i) a halogen atom, (ii) a $C_{1-6}$ alkyl group optionally substituted by 1 to 3 halogen atoms, and (iii) a $C_{1-6}$ alkoxy group, or
(4) a 3- to 8-membered monocyclic non-aromatic heterocyclic group,
or a salt thereof.

2. The compound or salt according to claim 1, which is represented by the formula (I'):

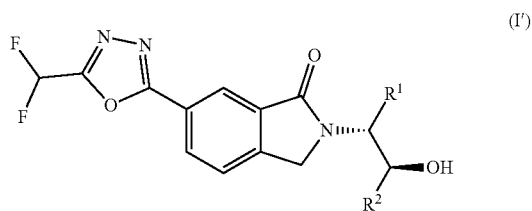

(I')

wherein each symbol is as defined in claim 1.

3. The compound or salt according to claim 1, wherein
$R^1$ is
(1) a $C_{3-10}$ cycloalkyl group optionally substituted by 1 to 3 halogen atoms, or
(2) a 5- or 6-membered monocyclic aromatic heterocyclic group optionally substituted by 1 to 3 substituents selected from (i) a halogen atom, (ii) a $C_{1-6}$ alkyl group optionally substituted by 1 to 3 halogen atoms, and (iii) a $C_{1-6}$ alkoxy group, and
$R^2$ is
(1) a $C_{6-14}$ aryl group optionally substituted by 1 to 3 substituents selected from (i) a halogen atom, and (ii) a $C_{1-6}$ alkyl group optionally substituted by 1 to 3 halogen atoms, or
(2) a 5- or 6-membered monocyclic aromatic heterocyclic group optionally substituted by 1 to 3 substituents selected from (i) a halogen atom, (ii) a $C_{1-6}$ alkyl group optionally substituted by 1 to 3 halogen atoms, and (iii) a $C_{1-6}$ alkoxy group.

4. The compound or salt according to claim 1, wherein
$R^1$ is
(1) a $C_{3-10}$ cycloalkyl group, or
(2) a 6-membered monocyclic aromatic heterocyclic group optionally substituted by 1 to 3 halogen atoms, and
$R^2$ is
(1) a $C_{6-14}$ aryl group optionally substituted by 1 to 3 halogen atoms, or
(2) a 6-membered monocyclic aromatic heterocyclic group optionally substituted by 1 to 3 halogen atoms.

5. A pharmaceutical composition comprising the compound or salt according to claim 1 and a pharmaceutically acceptable carrier.

* * * * *